US012570670B2

(12) United States Patent
Bennett et al.

(10) Patent No.: US 12,570,670 B2
(45) Date of Patent: Mar. 10, 2026

(54) COMPOUNDS, COMPOSITIONS, AND METHODS FOR TREATING FIBROSIS

(71) Applicant: YALE UNIVERSITY, New Haven, CT (US)

(72) Inventors: Anton Bennett, Wilton, CT (US); Gurulingappa Hallur, Bangalore (IN); Chandregowda Venkateshappa, Bangalore (IN); Athisayamani Jeyaraj Duraiswamy, Bangalore (IN); Rama Kishore V.P. Putta, Bangalore (IN)

(73) Assignee: Yale University, New Haven, CT (US)

( * ) Notice: Subject to any disclaimer, the term of this patent is extended or adjusted under 35 U.S.C. 154(b) by 1128 days.

(21) Appl. No.: 17/426,762

(22) PCT Filed: Jan. 30, 2020

(86) PCT No.: PCT/US2020/015955

§ 371 (c)(1),
(2) Date: Jul. 29, 2021

(87) PCT Pub. No.: WO2020/160321

PCT Pub. Date: Aug. 6, 2020

(65) Prior Publication Data

US 2022/0098214 A1 Mar. 31, 2022

Related U.S. Application Data

(60) Provisional application No. 62/798,517, filed on Jan. 30, 2019.

(51) Int. Cl.

| | |
|---|---|
| ***C07D 495/06*** | (2006.01) |
| ***A61K 31/519*** | (2006.01) |
| ***A61K 45/06*** | (2006.01) |
| ***A61P 21/00*** | (2006.01) |
| ***G01N 33/50*** | (2006.01) |

(52) U.S. Cl.

CPC .......... *C07D 495/06* (2013.01); *A61K 31/519* (2013.01); *A61K 45/06* (2013.01); *A61P 21/00* (2018.01); *G01N 33/5061* (2013.01); *G01N 2333/912* (2013.01)

(58) Field of Classification Search

CPC .. C07D 239/70; C07D 471/04; C07D 495/04; C07D 495/06; A61K 31/519; A61P 21/00; A61P 37/00

See application file for complete search history.

(56) References Cited

U.S. PATENT DOCUMENTS

| | | | | |
|---|---|---|---|---|
| 11,504,373 | B2 * | 11/2022 | Bennett | A61K 31/519 |
| 2010/0004256 | A1 | 1/2010 | Liu et al. | |
| 2012/0238542 | A1 | 9/2012 | Treu | |

FOREIGN PATENT DOCUMENTS

| | | | |
|---|---|---|---|
| EP | 1878727 | A1 | 1/2008 |
| WO | 2003083102 | A2 | 10/2003 |
| WO | 2007060198 | A1 | 5/2007 |
| WO | 2019126141 | A1 | 6/2019 |

OTHER PUBLICATIONS

Anonymous, "Map Kinase Phosphatase-5 (MKP-5) as a novel anti-fibrotic therapeutic target", OCR7100 Non-Confidential, XP055620308, 20 pages, 2017.
Bruno, O., et al., "Antiinflammatory agents: new series of N-substituted amino acids with complex pyrimidine structures endowed with antiphlogistic activity", Il Farmaco, 54(1-2):95-100, 1999.
Supplementary European Search Report issued Oct. 18, 2022 in European Application No. 20749685.2.
International Search Report and Written issued in International Application No. PCT/US2020/015955, mailing date of Jun. 29, 2020, 11 pages.
Pubchem, "3,3-dimethyl-1-[(9-methylsulfanyl-5,6-dihydrothieno[3,4-h]quinazolin-2-yl)sulfanyl]butan-2-one", Substance Record for SID 111457484, Available Date: Mar. 7, 2011 [retrieved on May 4, 2020], Retrieved from the Internet: <url:https://pubchem.ncbi.nlm.nih.gov/substance/111457484>.

* cited by examiner

*Primary Examiner* — Sarah Pihonak
(74) *Attorney, Agent, or Firm* — Saul Ewing LLP; Domingos Silva; Kathryn Doyle

(57) ABSTRACT

The present invention provides compounds and methods for treating MKP5 modulated disease. In certain embodiments, the MKP5 modulated disease is a fibrotic disease.

27 Claims, 30 Drawing Sheets

Specification includes a Sequence Listing.

1

$K_d = 1.01 \pm 0.19\ \mu M$ $IC_{50} = 3.86 \pm 0.62\ \mu M$

IC50 = 1.23 μM (98.7%)

Mol Wt: 655.83
tPSA: 86.57
CLogP: 4.36

IC50 = 0.85 μM (98.7%)

Mol.Wt: 572.85
tPSA: 65.34
CLogP: 4.57

IC50 = 1.05 μM (93.5%)

Mol.Wt: 600.86
tPSA: 82.41
CLogP: 3.34

IC50 = 1.97 μM (74.5%)

Mol.Wt: 547.75
tPSA: 88.4
CLogP: 4.54

IC50 = 2.71 μM (98.7%)

Mol. Wt: 555.73
tPSA: 99.4
CLogP: 5.12

IC50 = 2.95 μM (78% Max inhibition)

M.Wt: 364.54
tPSA: 41.79
CLogP: 4.37

IC50 = 2.46 μM (99%)

M.Wt: 408.54
tPSA: 79.09
CLogP: 4.23

IC50 = 5.49 μM (100%)

M.Wt: 479.64
tPSA: 99.4
CLogP: 3.1

IC50 = 4.56 μM (98%)

M.Wt: 476.69
tPSA: 74.1
CLogP: 3.1

IC50 = 4.15 μM (98%)

M.Wt: 465.66
tPSA: 82.3
CLogP: 3.6

IC50 = 2.96 μM (97%)

M.Wt: 490.67
tPSA: 91.2
CLogP: 2.9

IC50 = 2.73 μM (96%)

M. Wt: 507.68
tPSA: 88.4
CLogP: 3.83158

IC50 = No fit
Mol.Wt: 392.48
tPSA: 88.32
CLogP: 3.71

IC50 = 3.47 μM (100%)
Mol.Wt: 601.84
tPSA: 85.65
CLogP: 2.61

IC50 = 2.3 μM (33.5%)
Mol.Wt: 505.66
tPSA: 88.17
CLogP: 3.7

IC50 = 3.04 μM (100%)
Mol.Wt: 587.86
tPSA: 68.58
CLogP: 4.09

IC50 = 1.23 μM (98.7%)
Mol Wt: 655.83
tPSA: 86.57
CLogP: 4.36

IC50 = 0.85 μM
(98.7%)
Mol.Wt: 572.85
tPSA: 65.34
CLogP: 4.57

IC50 = 1.05 μM
(93.5%)
Mol.Wt: 600.86
tPSA: 82.41
CLogP: 3.34

IC50 = 2.34 μM
(79.2%)
Mol.Wt: 552.77
tPSA: 74.46
CLogP: 4.08

IC50 = 18.4 μM
(59.58%)
Mol.Wt: 571.86
tPSA: 62.1
CLogP: 7.03

IC50 = Nofit
Mol.Wt: 551.78
tPSA: 62.1
CLogP: 5.57

IC50 = Nofit
Mol.Wt: 567.78
tPSA: 82.33
CLogP: 3.94

IC50 = 3.47 μM (100%)
Mol.Wt: 601.84
tPSA: 85.65
CLogP: 2.61

IC50 = 3.04 μM (100%)
Mol.Wt: 587.86
tPSA: 68.58
CLogP: 4.09

IC50 = 5.52 µM (71%)

Mol.Wt: 519.69
tPSA: 88.4
CLogP: 3.83

IC50 = 2.73 µM (95.9%)

Mol.Wt: 507.68
tPSA: 88.4
CLogP: 3.83

IC50 = 1.79 µM (75%)

Mol.Wt: 533.72
tPSA: 88.4
CLogP: 4.39

IC50 = 1.97 µM (74.5%)

Mol.Wt: 547.75
tPSA: 88.4
CLogP: 4.54

IC50 = No fit

Mol.Wt: 583.78
tPSA: 88.4
CLogP: 5.82

IC50 = 2.71 µM (98.7%)

Mol. Wt: 555.73
tPSA: 99.4
CLogP: 5.12

IC50 = 2.18 µM (99.4%)

Mol.Wt: 493.66
tPSA: 88.4
CLogP: 3.30

IC50 = 1.89 µM (99.9%)

Mol.Wt: 519.69
tPSA: 99.4
CLogP: 4.09

IC50 = 3.12 µM (88.8%)

Mol.Wt: 432.59
tPSA: 90.9
CLogP: 4.07

IC50 = 2.3 µM (33.5%)

Mol.Wt: 505.66
tPSA: 88.17
CLogP: 3.7

IC50 = 2.96 µM (97.4%)
Mol.Wt: 490.66
tPSA: 91.2
CLogP: 2.93

IC50 = 4.43 µM
(96.6%)
Mol.Wt: 504.68
tPSA: 82.41
CLogP: 3.47

MKP-5 inhibitor
IC50 = 7.7 μM
YUI-0000001
IC50 = 3.56 μM (71%)
Mol.Wt:
tPSA: 41.79
CLogP:

A ring SAR

COMPOUNDS, COMPOSITIONS, AND METHODS FOR TREATING FIBROSIS

CROSS-REFERENCE TO RELATED APPLICATIONS

The present application is a 35 U.S.C. § 371 national phase application from, and claims priority to, International Application No. PCT/US2020/015955 filed Jan. 30, 2020, which claims priority under 35 U.S.C. § 119(e) to U.S. Provisional Application No. 62/798,517 filed Jan. 30, 2019, all of which application are incorporated herein by reference in their entireties.

STATEMENT REGARDING FEDERALLY SPONSORED RESEARCH OR DEVELOPMENT

This invention was made with government support under AR066003 awarded by National Institutes of Health. The government has certain rights in the invention.

SEQUENCE LISTING

The ASCII text file named "047162-7193US1_Seq_Listing_ST25" created on Apr. 15, 2025, comprising 8,008 bytes, is hereby incorporated by reference in its entirety.

BACKGROUND OF THE INVENTION

Protein phosphorylation is a critical post-translational modification controlled by the actions of both protein kinases and protein phosphatases. The mitogen-activated protein kinases (MAPKs), which are a family of serine/threonine kinases, play indispensable roles in signal transduction pathways that control a plethora of physiological responses. Dysregulation of MAPK activity is causal to the pathogenesis of many human diseases, including cancer, obesity, and diabetes, and diseases of the immune, cardiac and musculoskeletal systems. Therefore, exquisite regulation of this activity is crucial to maintaining health.

One major regulator of the MAPKs is the family of MAPK phosphatases (MKPs), which are a subset of the dual-specificity phosphatases (DUSPs). By direct dephosphorylation of the regulatory tyrosine and threonine residues on the activation loop of MAPKs, the MKPs can inactivate these kinases. While MKPs share a common fold with the DUSPs and the larger family of protein tyrosine phosphatases (PTPs), they have a kinase interaction motif (KIM) distal to the catalytic domain and this allows them to bind directly and discriminate amongst MAPK substrates. This binding often triggers a conformational shift in the catalytic domain to facilitate dephosphorylation.

The MKPs are divided into three subfamilies based on their MAPK substrate selectivity and subcellular localization, with one group, including MKP5, MKP7, and DUSP8/VH5, that specifically dephosphorylates the stress-activated MAPKs, p38 MAPK, and c-Jun $NH_2$-terminal kinase (JNK). These mechanisms allow the MKPs to exhibit tight control over MAPK activity.

There is a need in the art for novel compounds and compositions that can be used to specifically inhibit MKPs. Such compounds can be used to treat, ameliorate, and/or prevent a MKP-mediated disease, such as but not limited to a fibrotic disease or disorder. The present disclosure addresses this need.

BRIEF SUMMARY OF THE INVENTION

The invention provides a compound, or a salt, solvate, enantiomer, diastereomer, or tautomer thereof, as described elsewhere herein. The invention further provides a pharmaceutical composition comprising at least one compound contemplated herein and at least one pharmaceutically acceptable carrier. The invention further provides a method of treating or preventing a MKP5 modulated disease or disorder in a subject. In certain embodiments, the method comprises administering to the subject a therapeutically effective amount of at least one compound contemplated herein. The invention further provides a method of determining if a test compound is a MKP5 inhibitor. In certain embodiments, the method comprises contacting a test compound with a peptide comprising the amino acid sequence pThr-Gly-pTyr and the catalytic domain of MKP5, or an active fragment thereof, thus forming a composition, measuring MKP5 activity in the composition, and comparing the MKP5 activity in the composition to a control.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIG. 1A depicts a schematic of the high-throughput screen of MKP5 inhibitors. Using a malachite green to quantify phosphate release, 1 μM of the MKP5 catalytic domain (MKP5-CD), 25 μM substrate phosphopeptide (SEQ ID NO: 15), and 20 μM of each compound were combined. FIG. 1B depicts a summary of screen results. The dotted line represents 30% threshold for hit identification. The dark circle indicates Compound (Cpmd) 1. FIG. 1C depicts the chemical structure of 1 and the calculated $K_d$ and $IC_{50}$ assayed against MKP5-CD. FIG. 1D depicts a microscale thermophoresis assay of MKP5-CD:1 binding. Curve-fit to hyperbolic binding-equation; $F_{norm}$—Normalized fluorescence. FIGS. 1E-1F depict a malachite green assay of MKP5-CD (FIG. 1E) and MKP1-CD (FIG. 1F) inhibition. Data are normalized against DMSO control and fit to hyperbolic inhibition equation. FIG. 1G depicts Lineweaver-Burk plot of phosphate sensor kinetic assay of Cmpd 1 inhibition. Data were fit to straight line. Nonlinear regression of the same data is shown in FIG. 17. For FIGS. 1D-1F, data are presented as mean±SD or G, mean and are the product of three independent experiments.

FIG. 2A depicts a $2F_o$-$F_c$ map surrounding 1 in chain A. Map displayed at $\sigma$=1.5. FIG. 2B depicts the location of 1 binding pocket on MKP5-CD in relation to catalytic site. Surface representation of MKP5-CD (A) in complex with 1 (B) bound to allosteric site. Cys408 is highlighted (C). FIG. 2C depicts key interactions between 1 and MKP5-CD, including hydrogen bond with Asn448 backbone and π-stacking with Tyr435. Other residues involved in hydrophobic interactions also shown (SEQ ID NO: 16). Relevant secondary structure features labeled in drawing. FIGS. 2D-2E depict the allosteric site (SEQ ID NO: 16) (FIG. 2D) and catalytic sites (SEQ ID NO: 17) (FIG. 2E) of MKP5-CD. MKP5-CD:1 (gray) overlaid with apo-MKP5-CD Chain A (PDB: 1ZZW, white). Residues with large shifts or involved in catalysis are labeled without a * or with a *, respectively. 1 has been removed for visibility. FIG. 2F depicts a surface representation of catalytic site of MKP5-CD. Molecules are colored as before. FIG. 2G depicts the quantification of active site volumes in apo-MKP5-CD and MKP5-CD:1 as determined with CAVER Analyst. Data are presented as mean±SD. Significance determined by two-tailed one-sample t-test (t=9.61, d.f.=5).

FIG. 3A depicts a multiple sequence alignment of DUSP catalytic domains. Sequences were aligned using Geneious and sorted by similarity to MKP5/DUSP10. Secondary structure elements of MKP5 indicated above the aligned sequence. Residues that are identical through all DUSPs are highlighted in underlined while those showing 60% similarity or greater (as determined by BLOSUM62 score of 3 or greater) are highlighted in bold. Catalytically active residues are indicated with !and residues forming interactions with 1 are indicated as follows: #—π-stacking, S—hydrogen bonding, @—hydrophobic interactions). Sequences are SEQ ID NOs:1-13, top to bottom. FIGS. 3B-3C depict activity (FIG. 3B) and inhibitor binding/potency (FIG. 3C) of mutant MKP5 constructs. Activity was measured using pNPP-based assay and normalized against wild-type MKP5-CD. Binding affinity and inhibitor potency determined as in FIGS. 1E-1F. Data presented as mean±SD and are the product of three independent experiments.

FIG. 4A depicts JNK1 (A, surface and ribbon) clashes with 1 (B, space-filling) bound to MKP5-CD (C, ribbon). FIG. 4B depicts activation loop phosphopeptide clashes with α4-α5 and β5-α3 loops in MKP5-CD (SEQ ID NO: 16) (D, surface and ribbon). The catalytic Cys408 of MKP5-CD clashes with the activation loop phosphopeptide, while other clashing residues from both MKP5-CD and the phosphopeptide are highlighted. Labeled residues are numbered for corresponding residues in p38a MAPK. Models were generated using PyMOL.align.

FIG. 5A depicts the activity of 1 on ERK1/2 (upper panel), JNK (middle panel) and p38a MAPK (lower panel) in C2C12 myoblasts. Representative immunoblots of the indicated phosphorylated MAPK (pMAPK) and total MAPK are shown at the left of each graph. Graphs represent the ratio of pMAPK/MAPK as determined by quantitative fluorescent imaging. Normalized data represent means±SEM of three to eight independent experiments. FIG. 5B depicts Gastrocnemius muscle from either uninjured or injured mkp5$^{+/+}$ and mkp5$^{-/-}$ mice at 4 and 10 days after cardiotoxin-induced injury were harvested and lysates immunoblotted for pSmad2 and Smad2. Each lane represents results of an animal of the indicated genotype. Graphs represent quantitation of pSmad2 and Smad2 shown as a ratio. Data are means±SEM and n=5 mice per genotype. FIG. 5C depicts MEFs derived from mkp5$^{+/+}$ and mkp5$^{-/-}$ mice were treated with TGF-β1 (1 ng/ml) for 10 minutes or MEFs from mkp5$^{+/+}$ mice were treated with 1 followed by 10 minutes TGF-β1 (1 ng/ml) stimulation. Representative immunoblots for the indicated antibodies are shown. Corresponding graphs represent the ratio of pSmad2/Smad2 and pMAPK/MAPK as indicated. Data represent the means±SEM from three independent experiments. Statistical significances were determined by an unpaired t-test.

FIG. 15A depicts the activity of MKP5-CD and STEP-46 versus 1 concentration measured by pNPP. FIG. 15B depicts the activity of MKP5-CD and PTP1B versus 1 concentration measured by malachite green. Data are normalized against DMSO control and fit to hyperbolic inhibition equation.

FIG. 20A depicts microscale Thermophoresis assay of mutant MKP5-CD:1 binding. Curves fit to hyperbolic binding-equation; Fnorm—Normalized Fluorescence. FIG. 20B depicts a malachite green assay of wild-type and mutant MKP5-CD inhibition. Data are normalized against DMSO control and fit to hyperbolic inhibition equation.

DETAILED DESCRIPTION OF THE INVENTION

Figure 1A:
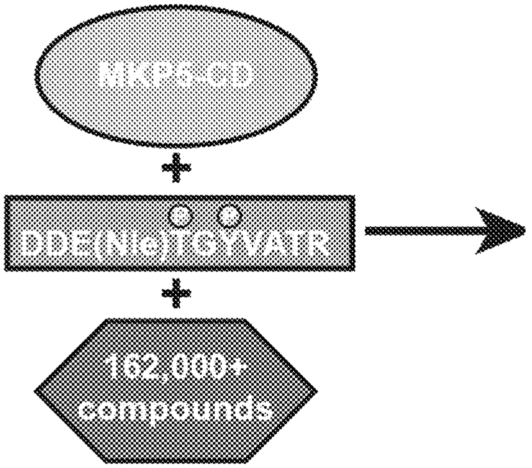
FIGS. 1A-1G show that a high-throughput screen yields micromolar inhibitor of MKP5.

The present invention relates in part to the identification of certain compounds as described herein that are MKP5 inhibitors. In other embodiments, these compounds can be used in treating and/or preventing fibrosis. In yet other embodiments, the present invention discloses compounds, as well as compositions comprising the same, and their use in treating and/or preventing fibrosis. In certain embodiments, compounds of the invention inhibit MKP5 through an allosteric mode of inhibition.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Generally, the nomenclature used herein and the laboratory procedures in cell culture, molecular genetics, pharmacology, and organic chemistry are those well-known and commonly employed in the art.

Standard techniques are used for biochemical and/or biological manipulations. The techniques and procedures are generally performed according to conventional methods in the art and various general references (e.g., Sambrook & Russell, 2012, Molecular Cloning, A Laboratory Approach, Cold Spring Harbor Press, Cold Spring Harbor, NY, and Ausubel et al., 2002, Current Protocols in Molecular Biology, John Wiley & Sons, NY), which are provided throughout this document.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity or frequency of at least one sign or symptom of the disease or disorder experienced by a patient is reduced.

As used herein, the terms "analog," "analogue," or "derivative" are meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or "therapeutically effective amount" of a compound is that amount of compound sufficient to provide a beneficial effect to the subject to which the compound is administered. An "effective amount" of a delivery vehicle is that amount sufficient to effectively bind or deliver a compound.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "MKP5 inhibitor" or "inhibitor of MKP5" as used herein refers to a composition or compound that inhibits at least in part, as compared to the control system that lacks the inhibitor, MKP5 activity, MKP5 expression and/or both, either directly or indirectly, using any method known to the skilled artisan. A MKP5 inhibitor may be any type of compound, including but not limited to, a nucleic acid, peptide, antibody, small molecule, antagonist, aptamer, or peptidomimetic. "MKP5" is used interchangeably with "MKP-5" herein.

As used herein, an "MKP5 modulated disease" or "MKP5 modulated disorder" refers to a disease associated with pathological accumulation of excessive extracellular matrix proteins in an organ or tissue. Non-limiting examples of such diseases encompass, but are not limited to, fibrosis, such as but not limited to cystic fibrosis or idiopathic pulmonary fibrosis.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" or "therapeutically acceptable salt" refers to a salt of the administered compounds prepared from pharmaceutically acceptable non-toxic acids, including inorganic acids or bases, organic acids or bases, solvates, hydrates, or clathrates thereof.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein, the terms "polypeptide," "protein," and "peptide" are used interchangeably and refer to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

By the term "specifically binds," as used herein, is meant a molecule, such as an antibody, which recognizes and binds to another molecule or feature, but does not substantially recognize or bind other molecules or features in a sample.

A "therapeutic" treatment is a treatment administered to a subject who exhibits signs of pathology, for the purpose of diminishing or eliminating those signs.

As used herein, the term "therapeutically effective amount" is an amount of a compound of the invention, that when administered to a patient, ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, "treating a disease or disorder" means reducing the frequency with which a symptom of the disease or disorder is experienced by a patient. Disease and disorder are used interchangeably herein. As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) delaying or minimizing the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

As used herein, the term "wild-type" refers to the genotype and phenotype that is characteristic of most of the members of a species occurring naturally and contrasting with the genotype and phenotype of a mutant.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl.

Certain specific examples include ($C_1$-$C_6$)alkyl, such as, but not limited to, ethyl, methyl, isopropyl, isobutyl, n-pentyl, n-hexyl and cyclopropylmethyl. As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$) cycloalkyl, such as, but not limited to, cyclopropyl, cyclobutyl, cyclopentyl and cyclohexyl.

As used herein, the term "substituted alkyl" or "substituted cycloalkyl" means alkyl or cycloalkyl, as defined above, substituted by one, two or three substituents selected from the group consisting of halogen, —OH, alkoxy, tetrahydro-2-H-pyranyl, $—NH_2$, $—N(CH_3)_2$, (1-methyl-imidazol-2-yl), pyridin-2-yl, pyridin-3-yl, pyridin-4-yl, —C(═O)OH, trifluoromethyl, —C≡N, —C(═O)O($C_1$-$C_4$)alkyl, $—C(═O)NH_2$, —C(═O)NH($C_1$-$C_4$)alkyl, —C(═O)N(($C_1$-$C_4$)alkyl)Z—$SO_2NH_2$, $—C(═NH)NH_2$, and $—NO_2$, advantageously containing one or two substituents selected from halogen, —OH, alkoxy, —$NH_2$, trifluoromethyl, —$N(CH_3)_2$, and —C(═O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(═O)—$CH_3$. Up to two heteroatoms may be consecutive, such as, for example, —$CH_2$—NH—$OCH_3$, or —$CH_2$—$CH_2$—S—S—$CH_3$.

As used herein, the term "aromatic" refers to a carbocycle or heterocycle with one or more polyunsaturated rings and having aromatic character, i.e. having (4n+2) delocalized a (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet another embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, in particular, straight.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds and Compositions

In one aspect, the invention provides a compound of formula (1), or a salt, solvate, enantiomer, diastereomer, or tautomer thereof:

(1)

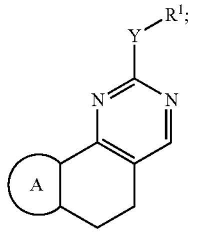

wherein:

Y is selected from the group consisting of S and NH;

A ring is selected from the group consisting of

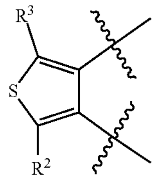 and 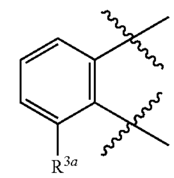;

$R^1$ is —C(R')(R")—C(═O)—R", wherein:

R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl;

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of —CN, 1H-tetrazol-5-yl (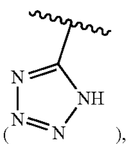), —C(═O)NH—S(═O)$_2$($C_1$-$C_6$ alkyl or $C_3$-$C_8$ cycloalkyl), and —C(═O)N$R^{2a}R^{2b}$, wherein $R^{2a}$ and $R^{2b}$ are independently selected from the group consisting of optionally substituted $C_1$-$C_6$ alkyl, optionally substituted $C_3$-$C_8$ cycloalkyl, optionally substituted phenyl, optionally substituted heteroaryl, —S(═O)$_2$($C_1$-$C_6$ alkyl), and —S(═O)$_2$($C_3$-$C_8$ cycloalkyl), or $R^{2a}$ and $R^{2b}$ combine with the N atom to which they are bound to form optionally substituted 3- to 8-membered heterocyclyl or heteroaryl;

$R^3$ is selected from the group consisting of H, $C_1$-$C_6$ alkyl, and $C_1$-$C_6$ thioether;

$R^{3a}$ is selected from the group consisting of —COOH, —CN, and —C(═O)N$R^{3b}R^{3c}$, wherein $R^{3b}$ and $R^{3c}$ are independently selected from the group consisting of H, optionally substituted $C_1$-$C_6$ alkyl, optionally substituted $C_3$-$C_8$ cycloalkyl, optionally substituted phenyl, and optionally substituted heteroaryl, or $R^{3b}$ and $R^{3c}$ combine with the N atom to which they are bound to form optionally substituted 3- to 8-membered heterocyclyl.

In certain embodiments, $R^1$ is —C(R')(R")—C(═O)—R". In other embodiments, $R^1$ is —C(R')(R")—C(═O)-(optionally substituted $C_1$-$C_6$ alkyl). In yet other embodiments, $R^1$ is —C(R')(R")—C(═O)-(optionally substituted tBu).

In certain embodiments, R' and R" are independently selected from the group consisting of H, Me, and Et. In other embodiments, R' is H. In yet other embodiments, R" is H.

In certain embodiments, $R^1$ is selected from the group consisting of:

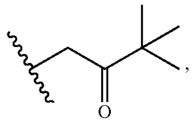 [SMILES: *CC(=O)C(C)(C)C], 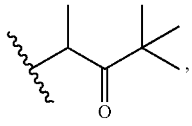, and 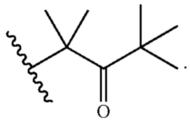.

In other embodiments, $R^1$ is

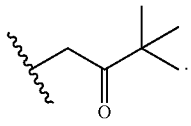 [SMILES: *CC(=O)C(C)(C)C].

In yet other embodiments, $R^1$ is

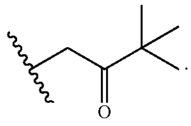 [SMILES: *CC(=O)C(C)(C)C].

In yet other embodiments, $R^1$ is

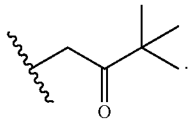.

In certain embodiments, $R^2$ is —CN. In other embodiments, $R^2$ is 1H-tetrazol-5-yl. In yet other embodiments, $R^2$ is

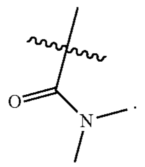
nyet other embodiments, $R^2$ is
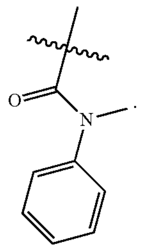 [SMILES: *C(=O)N(C)c1ccccc1]
In yet other embodiments, $R^2$ is
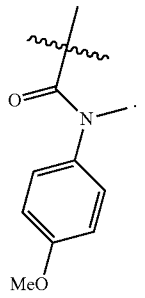 [SMILES: *C(=O)N(C)c1ccc(OC)cc1]
In yet other embodiments, $R^2$ is
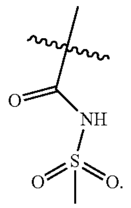 [SMILES: *C(=O)NS(C)(=O)=O]
In yet other embodiments, $R^2$ is
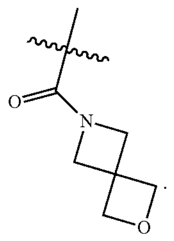 [SMILES: *C(=O)N1CC2(COC2)C1]
In yet other embodiments, $R^2$ is
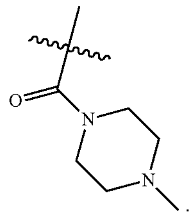 [SMILES: *C(=O)N1CCN(C)CC1]
In yet other embodiments, $R^2$ is
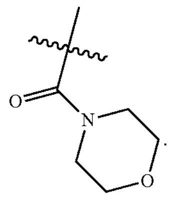 [SMILES: *C(=O)N1CCOCC1]
In yet other embodiments, $R^2$ is
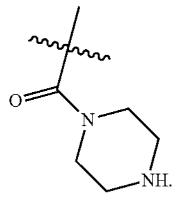 [SMILES: *C(=O)N1CCNCC1]
In yet other embodiments, $R^2$ is
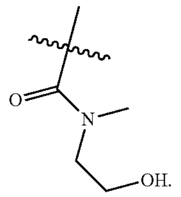 [SMILES: *C(=O)N(C)CCO]
In yet other embodiments, $R^2$ is
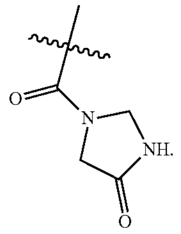 [SMILES: *C(=O)N1CNC(=O)C1]

In yet other embodiments, $R^2$ is
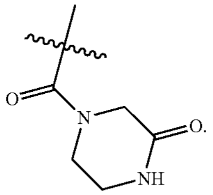 [SMILES: *C(=O)N1CCNC(=O)C1]
In yet other embodiments, $R^2$ is
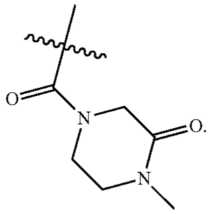 [SMILES: *C(=O)N1CCN(C)C(=O)C1]
In yet other embodiments, $R^2$ is
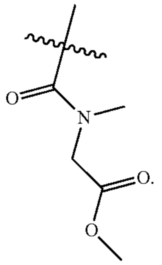 [SMILES: *C(=O)N(C)CC(=O)OC]
In yet other embodiments, $R^2$ is
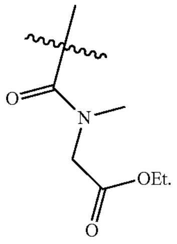 [SMILES: *C(=O)N(C)CC(=O)OCC]
In yet other embodiments, $R^2$ is
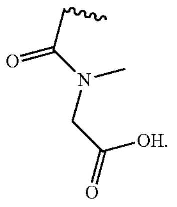
In yet other embodiments, $R^2$ is
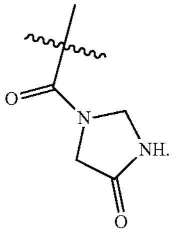 [SMILES: *C(=O)N1CNC(=O)C1]
In yet other embodiments, $R^2$ is
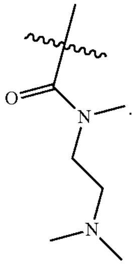 [SMILES: *C(=O)N(C)CCN(C)C]
In yet other embodiments, $R^2$ is NH
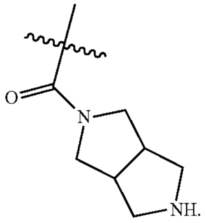 [SMILES: *C(=O)N1CC2CNCC2C1]
In yet other embodiments, $R^2$ is
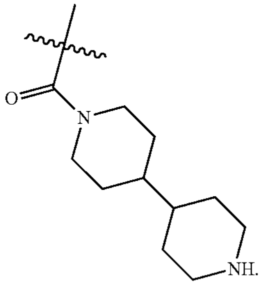 [SMILES: *C(=O)N1CCC(C2CCNCC2)CC1]
In yet other embodiments, $R^2$ is
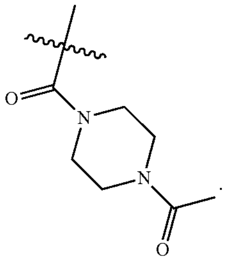 [SMILES: *C(=O)N1CCN(C(C)=O)CC1]

In yet other embodiments, $R^2$ is
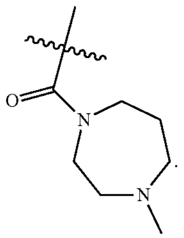 [SMILES: *C(=O)N1CCCN(C)CC1]
In yet other embodiments, $R^2$ is
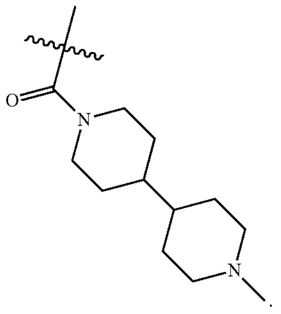 [SMILES: *C(=O)N1CCC(C2CCN(C)CC2)CC1]
In yet other embodiments, $R^2$ is
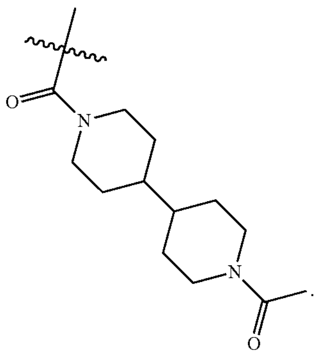 [SMILES: *C(=O)N1CCC(C2CCN(C(C)=O)CC2)CC1]
In yet other embodiments, $R^2$ is
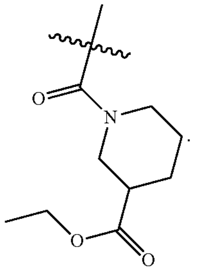 [SMILES: *C(=O)N1CCCC(C(=O)OCC)C1]
In yet other embodiments, $R^2$ is
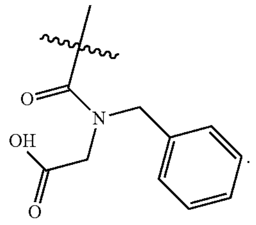 [SMILES: *C(=O)N(CC(=O)O)Cc1ccccc1]
In yet other embodiments, $R^2$ is
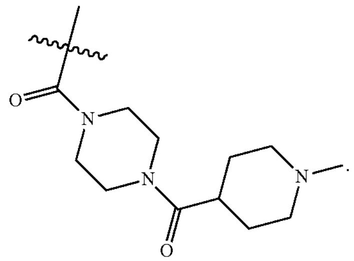 [SMILES: *C(=O)N1CCN(C(=O)C2CCN(C)CC2)CC1]
In yet other embodiments, $R^2$ is
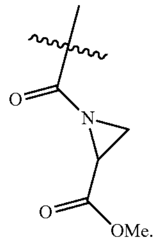 [SMILES: *C(=O)N1CC1C(=O)OC]
In yet other embodiments, $R^2$ is
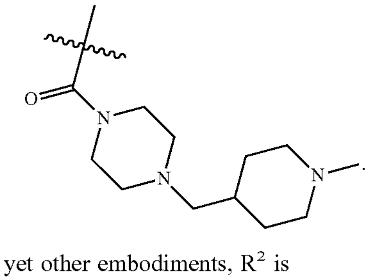
In yet other embodiments, $R^2$ is
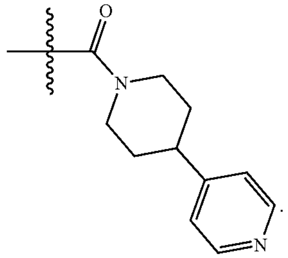 [SMILES: *C(=O)N1CCC(c2ccncc2)CC1]

In yet other embodiments, $R^2$ is
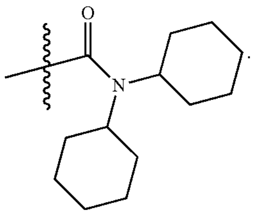 [SMILES: *C(=O)N(C1CCCCC1)C1CCCCC1]
In yet other embodiments, $R^2$ is
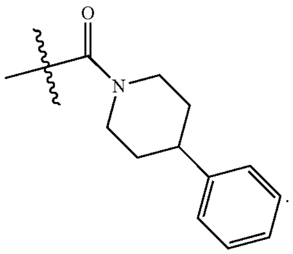 [SMILES: *C(=O)N1CCC(c2ccccc2)CC1]
In yet other embodiments, $R^2$ is
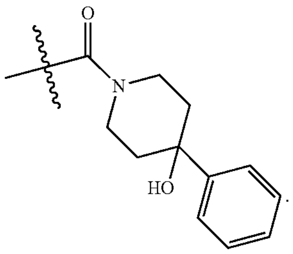 [SMILES: *C(=O)N1CCC(O)(c2ccccc2)CC1]
In yet other embodiments, $R^2$ is
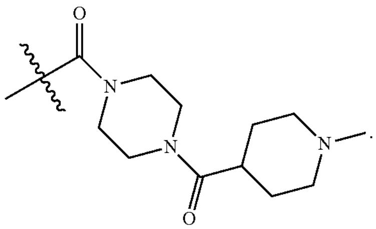 [SMILES: *C(=O)N1CCN(C(=O)C2CCN(C)CC2)CC1]
In yet other embodiments, $R^2$ is
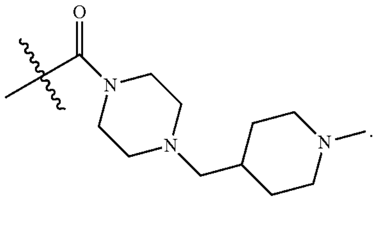 [SMILES: *C(=O)N1CCN(CC2CCN(C)CC2)CC1]
In yet other embodiments, $R^2$ is
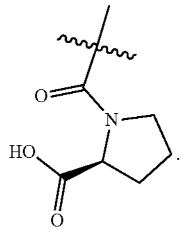 [SMILES: *C(=O)N1CCC[C@H]1C(=O)O]
In yet other embodiments, $R^2$ is
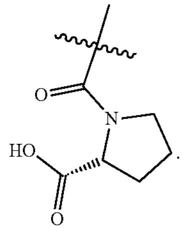
In yet other embodiments, $R^2$ is
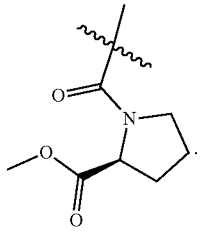 [SMILES: *C(=O)N1CCC[C@H]1C(=O)OC]
In yet other embodiments, $R^2$ is
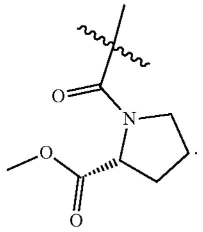
In yet other embodiments, $R^2$ is
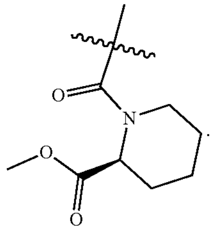 [SMILES: *C(=O)N1CCCC[C@H]1C(=O)OC]

In yet other embodiments, $R^2$ is

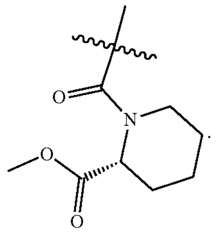 [SMILES: *C(=O)N1CCCC[C@@H]1C(=O)OC]

In yet other embodiments, $R^2$ is

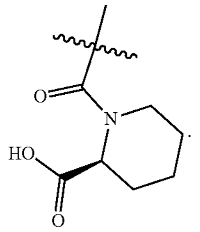 [SMILES: *C(=O)N1CCCC[C@H]1C(=O)O]

In yet other embodiments, $R^2$ is

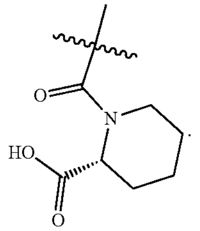 [SMILES: *C(=O)N1CCCC[C@@H]1C(=O)O]

In yet other embodiments, $R^2$ is

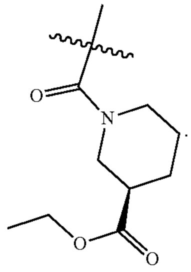 [SMILES: *C(=O)N1CCC[C@@H](C(=O)OCC)C1]

In yet other embodiments, $R^2$ is

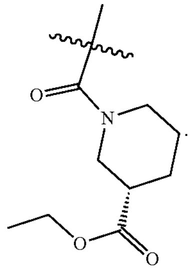 [SMILES: *C(=O)N1CCC[C@H](C(=O)OCC)C1]

In yet other embodiments, $R^2$ is

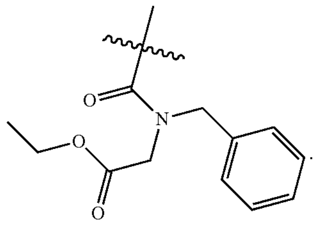 [SMILES: *C(=O)N(CC(=O)OCC)Cc1ccccc1]

In yet other embodiments, $R^2$ is

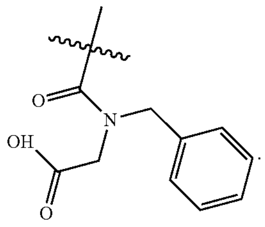 [SMILES: *C(=O)N(CC(=O)O)Cc1ccccc1]

In yet other embodiments, $R^2$ is

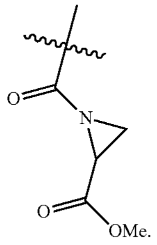 [SMILES: *C(=O)N1CC1C(=O)OC]

In certain embodiments, $R^3$ is $C_1$-$C_6$ thioether. In other embodiments, $R^3$ is —SMe. In yet other embodiments, $R^3$ is —SEt. In yet other embodiments, $R^3$ is —S(nPr). In yet other embodiments, $R^3$ is —S(iPr). In yet other embodiments, $R^3$ is —S(nBu). In yet other embodiments, $R^3$ is —S(secBu). In yet other embodiments, $R^3$ is —S(iBu). In yet other embodiments, $R^3$ is —S(tBu).

In certain embodiments, $R^{3a}$ is

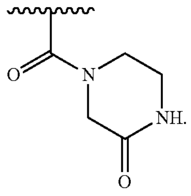 [SMILES: *C(=O)N1CCNC(=O)C1]

In other embodiments, $R^3$ is

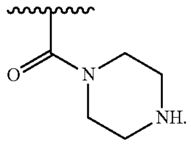 [SMILES: *C(=O)N1CCNCC1]

In yet other embodiments, $R^{3a}$ is

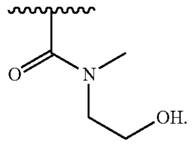 [SMILES: *C(=O)N(C)CCO]

In certain embodiments, the compound is

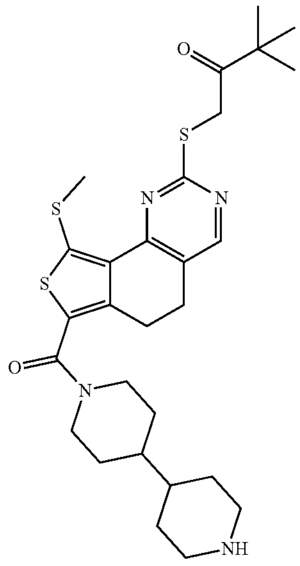 [SMILES: CSc1sc(C(=O)N2CCC(C3CCNCC3)CC2)c2c1-c1nc(SCC(=O)C(C)(C)C)ncc1CC2]

or a salt, solvate, or tautomer thereof.

In certain embodiments, the compound is

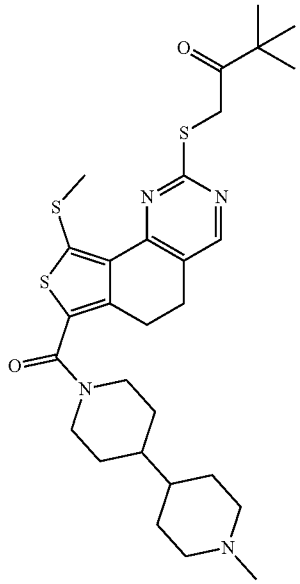 [SMILES: CSc1sc(C(=O)N2CCC(C3CCN(C)CC3)CC2)c2c1-c1nc(SCC(=O)C(C)(C)C)ncc1CC2]

or a salt, solvate, or tautomer thereof.

In certain embodiments, the compound is

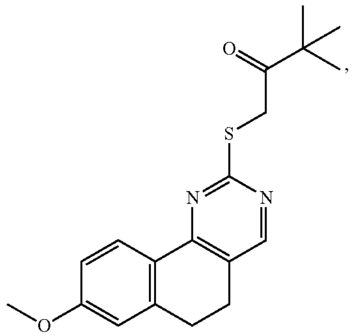 [SMILES: COc1ccc2c(c1)CCc1cnc(SCC(=O)C(C)(C)C)nc1-2]

or a salt, solvate, enantiomer, diastereomer, or tautomer thereof. In certain embodiments, the compound is

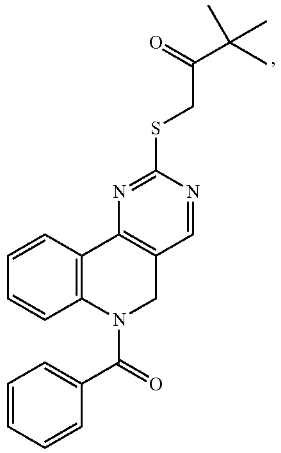 [SMILES: CC(C)(C)C(=O)CSc1ncc2c(n1)-c1ccccc1N(C(=O)c1ccccc1)C2]

or a salt, solvate, enantiomer, diastereomer, or tautomer thereof. In certain embodiments, the compound is

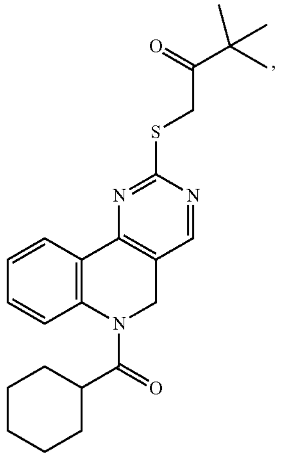 [SMILES: CC(C)(C)C(=O)CSc1ncc2c(n1)-c1ccccc1N(C(=O)C1CCCCC1)C2]

or a salt, solvate, enantiomer, diastereomer, or tautomer thereof. In certain embodiments, the compound is

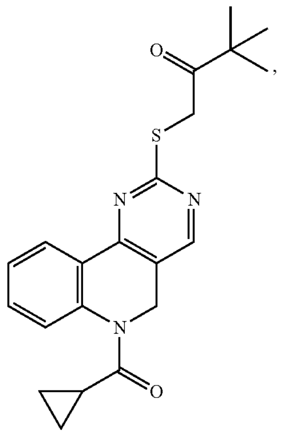 [SMILES: CC(C)(C)C(=O)CSc1ncc2c(n1)-c1ccccc1N(C(=O)C1CC1)C2]

or a salt, solvate, enantiomer, diastereomer, or tautomer thereof. In certain embodiments, the compound is

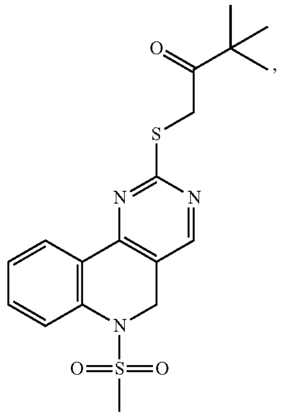 [SMILES: CC(C)(C)C(=O)CSc1ncc2c(n1)-c1ccccc1N(S(C)(=O)=O)C2]

or a salt, solvate, enantiomer, diastereomer, or tautomer thereof. In certain embodiments, the compound is

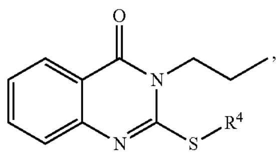

or a salt, solvate, enantiomer, diastereomer, or tautomer thereof. In certain embodiments, the compound is

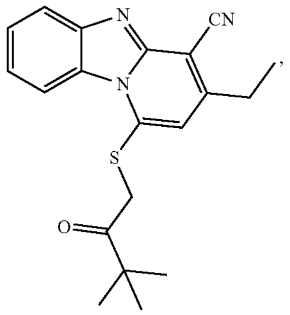 [SMILES: CCc1cc(SCC(=O)C(C)(C)C)n2c(nc3ccccc32)c1C#N]

or a salt, solvate, enantiomer, diastereomer, or tautomer thereof. In certain embodiments, the compound is

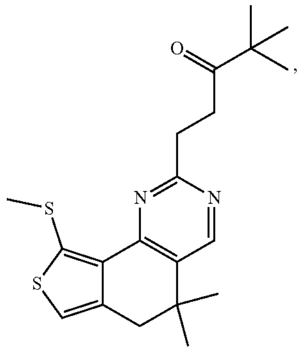 [SMILES: CSc1scc2c1-c1nc(CCC(=O)C(C)(C)C)ncc1C(C)(C)C2]

or a salt, solvate, enantiomer, diastereomer, or tautomer thereof. In certain embodiments, the compound is

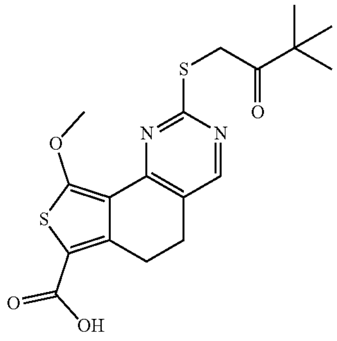 [SMILES: COc1sc(C(=O)O)c2c1-c1nc(SCC(=O)C(C)(C)C)ncc1CC2]

or a salt, solvate, enantiomer, diastereomer, or tautomer thereof. In certain embodiments, $R^4$ is selected from the group consisting of

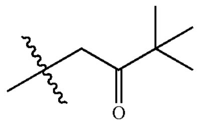 and 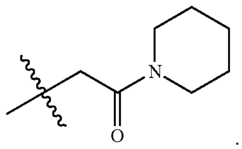 .

In certain embodiments, each occurrence of alkyl, cycloalkyl, or heterocyclyl is independently optionally substituted with at least one substituent selected from the group consisting of $C_1$-$C_6$ alkyl, $C_3$-$C_8$ cycloalkyl, halo, cyano (—CN), —$OR^a$, optionally substituted phenyl (thus yielding, in non-limiting examples, optionally substituted phenyl-($C_1$-$C_3$ alkyl), such as, but not limited to, benzyl or substituted benzyl), optionally substituted heteroaryl, optionally substituted heterocyclyl, —C(=O)$OR^a$, —OC(=O)$R^a$, —$SR^a$, —S(=O)$R^a$, —S(=O)$_2R^a$, —S(=O)$_2NR^aR^a$, —N($R^a$)S(=O)$_2R^a$, —N($R^a$)C(=O)$R^a$, —C(=O)$NR^aR^a$, and —N($R^a$)($R^a$), wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

In certain embodiments, each occurrence of aryl or heteroaryl is independently optionally substituted with at least one substituent selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, —CN, —$OR^b$, —N($R^b$)($R^b$), —$NO_2$, —C(=O)N($R^b$)($R^b$), —C(=O)$OR^b$, —OC(=O)$R^b$, —$SR^b$, —S(=O)$R^b$, —S(=O)$_2R^b$, —N(R)S(=O)$_2R^b$, —S(=O)$_2$N($R^b$)($R^b$), acyl, and $C_1$-$C_6$ alkoxycarbonyl, wherein each occurrence of $R^b$ is independently H, $C_1$-$C_6$ alkyl, or $C_3$-$C_8$ cycloalkyl, wherein in $R^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —O($CH_2$)$_{1-3}$O—.

In certain embodiments, each occurrence of aryl or heteroaryl is independently optionally substituted with at least one substituent selected from the group consisting of $C_1$-$C_6$ alkyl, $C_3$-$C_8$ cycloalkyl, phenyl, $C_1$-$C_6$ hydroxyalkyl, ($C_1$-$C_6$ alkoxy)-$C_1$-$C_6$ alkyl, $C_1$-$C_6$ haloalkyl, $C_1$-$C_6$ haloalkoxy, halogen, —$OR^b$, —C(=O)N($R^b$)($R^b$), —C(=O)$OR^b$, —OC(=O)$R^b$, —$SR^b$, —S(=O)$R^b$, —S(=O)$_2R^b$, and —N($R^b$)S(=O)$_2R^b$, wherein each occurrence of $R^b$ is independently H, $C_1$-$C_6$ alkyl, or $C_3$-$C_8$ cycloalkyl, wherein in $R^b$ the alkyl or cycloalkyl is optionally substituted with at least one selected from the group consisting of halogen, —OH, $C_1$-$C_6$ alkoxy, and heteroaryl; or substituents on two adjacent carbon atoms combine to form —O($CH_2$)$_{1-3}$O—.

In certain embodiments, the alkyl, cycloalkyl, heteroaryl, heterocyclyl, aryl, or benzyl group is optionally independently substituted with at least one group selected from the group consisting of $C_1$-$C_6$ alkyl; $C_1$-$C_6$ alkoxy; $C_1$-$C_6$ haloalkyl; $C_1$-$C_6$haloalkoxy; —$NH_2$, —NH($C_1$-$C_6$ alkyl), —N($C_1$-$C_6$ alkyl)($C_1$-$C_6$ alkyl), halogen, —OH; —CN; phenoxy, —NHC(=O)H, —NHC(=O)$C_1$-$C_6$ alkyl, —C(=O)$NH_2$, —C(=O)NH$C_1$-$C_6$ alkyl, —C(=O)N($C_1$-$C_6$ alkyl)($C_1$-$C_6$ alkyl), tetrahydropyranyl, morpholinyl, —C(=O)$CH_3$, —C(=O)$CH_2$OH, —C(=O)$NHCH_3$, —C(=O)$CH_2$OMe, or an N-oxide thereof.

In certain embodiments, each occurrence of the heteroaryl is independently selected from the group consisting of pyridyl, pyrimidyl, pyrazinyl, imidazolyl, thiazolyl, pyrazolyl, isoxazolyl, oxadiazolyl (including 1,2,3-, 1,2,4-, 1,2,5-, and 1,3,4-oxadiazole), diazolyl (including 1,3-diazolyl and 1,2-diazolyl), and triazolyl (such as 1,2,3-triazolyl and 1,2,4-triazolyl).

In certain embodiments, each occurrence of the heterocyclyl group is independently selected from the group consisting of tetrahydrofuranyl, tetrahydropyranyl, piperidinyl, piperazinyl, pyrrolidinyl, morpholinyl, thiomorpholinyl, 1-oxido-thiomorpholinyl, 1,1-dioxido-thiomorpholinyl, oxazolidinyl, azetidinyl, imidazolidinyl, and the corresponding oxo analogues (where a methylene ring group is replaced with a carbonyl) thereof.

In certain embodiments, $R^2$ is

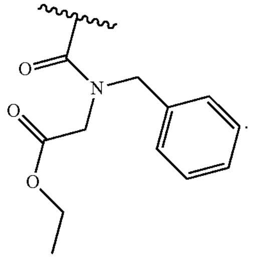 [SMILES: *C(=O)N(CC(=O)OCC)Cc1ccccc1]

In certain embodiments, $R^2$ is not

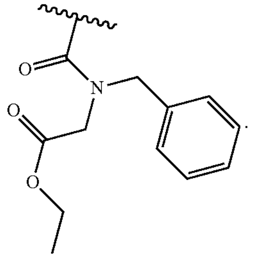 [SMILES: *C(=O)N(CC(=O)OCC)Cc1ccccc1]

In certain embodiments, $R^2$ is

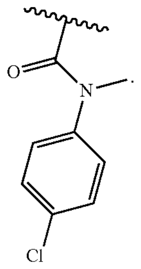 [SMILES: *C(=O)N(C)c1ccc(Cl)cc1]

In certain embodiments, $R^2$ is not

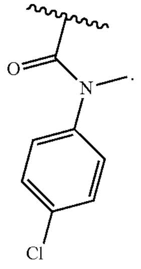 [SMILES: *C(=O)N(C)c1ccc(Cl)cc1]

In certain embodiments, $R^2$ is

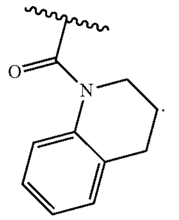 [SMILES: *C(=O)N1CCCc2ccccc21]

In certain embodiments, $R^2$ is not

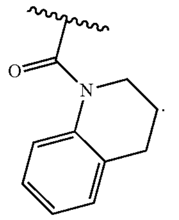 [SMILES: *C(=O)N1CCCc2ccccc21]

In certain embodiments, $R^2$ is

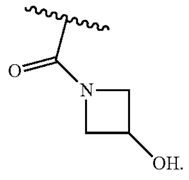 [SMILES: *C(=O)N1CC(O)C1]

In certain embodiments, $R^2$ is not

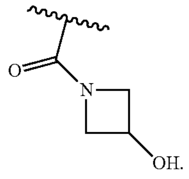 [SMILES: *C(=O)N1CC(O)C1]

In certain embodiments, $R^2$ is

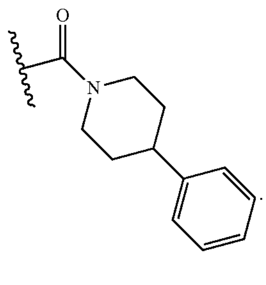 [SMILES: *C(=O)N1CCC(c2ccccc2)CC1]

In certain embodiments, $R^2$ is not

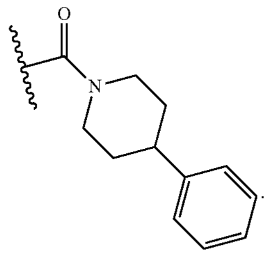 [SMILES: *C(=O)N1CCC(c2ccccc2)CC1]

In certain embodiments, $R^2$ is

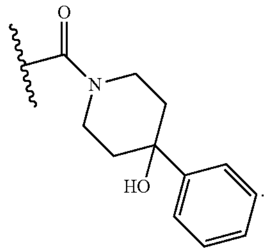 [SMILES: *C(=O)N1CCC(O)(c2ccccc2)CC1]

In certain embodiments, $R^2$ is not

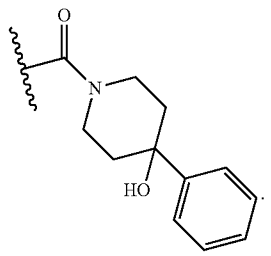 [SMILES: *C(=O)N1CCC(O)(c2ccccc2)CC1]

In certain embodiments, the invention provides a pharmaceutical composition comprising a compound of the invention and at least one pharmaceutically acceptable carrier.

Methods

In one aspect, the invention provides a method of treating, ameliorating, and/or preventing a MKP5 modulated disease in a subject. In certain embodiments, the method comprises administrating a compound of the invention to the subject. In other embodiments, the MKP5 modulated disease is any disease that can be treated or prevented by inhibition of MKP5. In yet other embodiments, the invention provides a method of treating, ameliorating, and/or preventing fibrotic disease in a subject.

In certain embodiments, the MKP5 modulated disease or disorder is a fibrotic disease or disorder. In other embodiments, the MKP5 modulated disease is dystrophic muscle disease. In yet other embodiments, the MKP5 modulated disease is dystrophic muscle disease. In yet other embodiments, the MKP5 modulated disease is a cardiac or vascular disease. In yet other embodiments, the MKP5 modulated disease is idiopathic pulmonary fibrosis.

The methods of the invention should not be construed to be limited to the compounds of the invention. Rather, any MKP5 inhibitor should be useful within the methods of the invention.

In certain embodiments, the compound useful within the methods of the invention is any compound of formula (1), or a salt, solvate, enantiomer, diastereomer, or tautomer thereof, as recited elsewhere herein.
In certain embodiments, the compound useful within the methods of the invention is selected from the group consisting of:
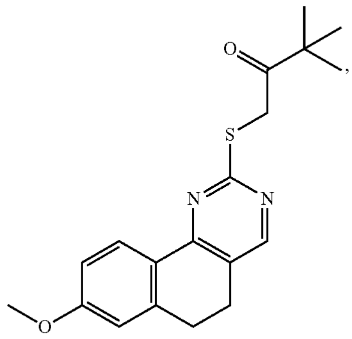
,
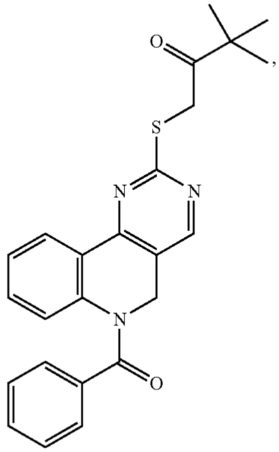
,
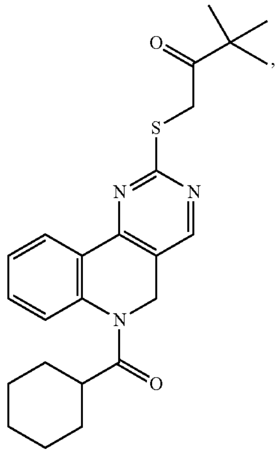
,
-continued
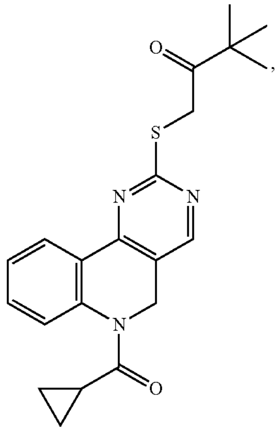
,
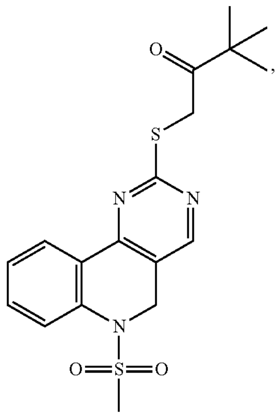
,
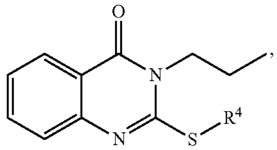
,
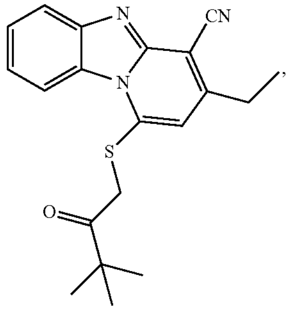
,
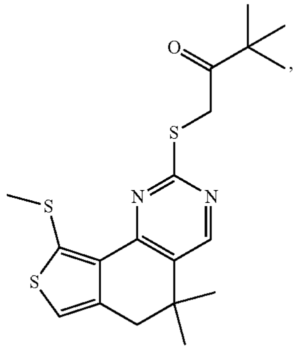
, and -continued

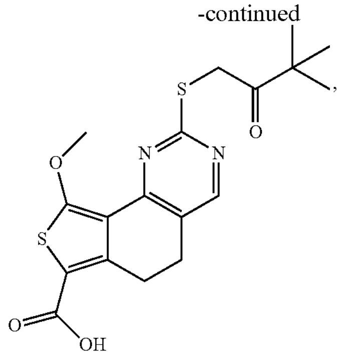

wherein $R^4$ is selected from the group consisting of

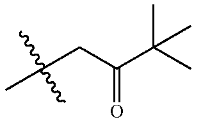 and 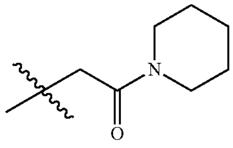 ;

or a salt, solvate, enantiomer, diastereomer, or tautomer thereof.

In certain embodiments, the subject is a mammal. In other embodiments, the mammal is human.

In certain embodiments, the MKP5 inhibitor is administered to the subject by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes. In other embodiments, the method further comprises administering to the subject at least one additional agent that treats, ameliorates, or prevents the MKP5 modulated disease or disorder in the mammal. In yet other embodiments, the inhibitor and at least one additional agent are coformulated. In yet other embodiments, the inhibitor and at least one additional agent are co-administered.

Method of Screening Compounds as MKP5 Inhibitors

In one aspect, the invention provides a method of identifying a compound that inhibits MKP5. In certain embodiments, the method comprises contacting a putative inhibitor compound with (i) a peptide comprising the sequence pThr-Gly-pTyr and (ii) the catalytic domain of MKP5 or an active fragment thereof, thus forming a composition. In other embodiments, the method comprises measuring MKP5 activity in the composition. In yet other embodiments, the method comprises comparing the MKP5 activity in the composition to a control; thereby identifying the putative inhibitor compound as a compound that inhibits MKP5.

In certain embodiments, the method is practiced as a high-throughput screen by which a plurality of compounds (putative inhibitors) are contacted with a peptide comprising pThr-Gly-pTyr and the catalytic domain of MKP5 or an active fragment thereof, and inhibitors are identified from among the plurality of compounds by comparing their individual activities to a control.

Without wishing to be limited by theory, including a peptide encompassing the pThr180-Gly-pTyr182 motif of p38α MAPK (which is present on the activation loop of p38α MAPK and represents the primary MKP5 substrate) in the assay uncovers more selective and thus more useful inhibitor compounds. In various embodiments, the peptide comprises Asp-Asp-Glu-Nle-pThr-Gly-pTyr-Val-Ala-Thr-Arg (SEQ ID NO: 15), wherein Nle is norleucine.

A person of skill in the art will recognize that activity can be measured by combining the substrate and MKP or any catalytically active fragment therefore, i.e. the MKP5 catalytic domain or an active fragment thereof. A person of skill in the art will appreciate that a variety of methods of measuring MKP5 activity and controls are possible and will be familiar with the same by analogy to activity assays. The control can be, by way of non-limiting example, a predetermined reference or may be a reaction performed without a MKP5 inhibitor.

Kits

The invention includes a kit comprising at least one compound contemplated within the invention, optionally an applicator, and instructional material for use thereof.

The instructional material included in the kit comprises instructions for preventing or treating a MKP5 modulated disease in a subject. The instructional material recites the amount of, and frequency with which, the compound should be administered to the mammal. In certain embodiments, the kit further comprises at least one additional agent that prevents or treats an MKP5 modulated disease in a subject. In other embodiments, the kit further comprises at least one additional agent that improves and/or prevents further loss of cognition in a subject.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, and any and all whole or partial increments therebetween. In some embodiments, the dose of a compound of the invention is from about 1 mg and about 2,500 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-fibrotic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using anon-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. The data obtained from cell culture assays and animal studies are optionally used in formulating a range of dosage for use in human. The dosage of such compounds lies preferably within a range of circulating concentrations that include the ED50 with minimal toxicity. The dosage optionally varies within this range depending upon the dosage form employed and the route of administration utilized.

Those skilled in the art will recognize or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

The materials and methods employed in the following Example are here described:

Protein Expression and Purification

The catalytic domain of MKP5 (MKP5-CD, residues 320-467) was inserted into a pET-28a vector for expression. Mutant constructs were generated according to the QuikChange II (Agilent) site directed mutagenesis protocol. Constructs were transformed into BL21 (DE3) cells and grown in LB containing 100 μg/mL kanamycin to an OD of 0.8. Protein expression was induced with 1 mM IPTG, and cells were harvested after overnight incubation at 22° C.

Cell pellets were resuspended in lysis buffer containing 20 mM Tris (pH 7.4), 200 mM NaCl, 10% glycerol, 5 mM imidazole, 2 mM β-mercaptoethanol, DNase1, and a complete EDTA-free protease inhibitor. Cells were lysed with a cell disruptor and cellular debris were pelleted by centrifugation. The supernatant was loaded by gravity flow onto a TALON resin column equilibrated in 20 mM Tris (pH 7.4), 200 mM NaCl, 10% glycerol, 5 mM imidazole, 2 mM β-mercaptoethanol and protein was eluted with the addition of 200 mM imidazole. MKP5-CD containing fractions were exchanged into thrombin cleavage buffer (50 mM Tris pH 8.4, 150 mM NaCl, 2.5 mM $CaCl_2$)). The N-terminal His-tag was removed by overnight incubation with thrombin at 4° C. After cleavage, the protein was reapplied to a TALON resin column and collected in the flow-through. The protein was concentrated to 12 mg/mL, exchanged into storage buffer and stored at −80° C. Full-length p38α MAPK was expressed and purified as previously described (Zhang, et al., 2008, J. Biol. Chem. 283:26591-26601). MKP1-CD (human aa 172-314) was expressed and purified by ARVYS Proteins (Trumbull, CT).

High-Throughput MKP5 Inhibitor Screen

A small molecule collection was screened for activity against MKP5-CD using a malachite green assay in 384-well format. MKP5-CD and p38α MAPK phosphopeptide (DDE(Nle)(pT)G(pY)VATR) substrate were diluted into PTP buffer (50 mM Tris pH 7.2, 1 mM EDTA, 0.1% β-mercaptoethanol, 0.01% Triton X-100). The screen was performed in two distinct phases. An initial screen against a subset of the compound library was carried out in the following conditions: 1.5 μM MKP5-CD, 25 μM phosphopeptide, 30 min at 37° C. A second follow-up screen was performed with the following modifications: 0.5 μM MKP5-CD, 50 μM phosphopeptide, 15 min at 30° C. Test compounds (20 nL) were dispensed with either an Aquarius (Tecan) pintool system (initial phase) or Echo 550 (Labcyte) acoustic dispenser (follow-up phase). In both phases, the test compound concentration was 20 μM in the 10 μL reaction and the final DMSO was 0.2%. The reaction was stopped by addition of 40 μL 1.6 N HCl containing 0.027% malachite green and 1.68% ammonium molybdate. The plate was incubated for 10-15 min at room temperature to allow color development and absorbance at 620 nm measured. The signal-to-background (S/B) ratio was calculated from the mean absorbance of vehicle-treated wells with and without enzyme (negative and positive controls; n=32 per condition). Percent inhibition of test wells was calculated from the mean positive and negative controls on each plate. The average S/B and Z' across 449 plates were 4.1 and 0.81, respectively. Plates with Z' less than 0.5 were excluded from further analysis. Wells with percent inhibition≥30% were considered active. Based on this cutoff, the overall hit rate for the screen was 0.2%.

Microscale Thermophoresis and Circular Dichroism

Binding interactions between MKP5-CD and 1 were carried out using microscale thermophoresis (MST) on a Monolith NT.115Pico instrument. MKP5-CD was labeled for MST using NanoTemper Monolith NTTM Protein Labeling Kit RED-NHS 2nd Generation (#MO-L011). Briefly, MKP5-CD was transferred into the provided labeling buffer and diluted to 20 μM. Dye was added in a 2-fold molar excess and allowed to incubate 30 minutes at room temperature. Excess dye was removed using the provided column equilibrated in 50 mM Tris pH 8.0, 150 mM NaCl, 0.05% Tween-20. A fixed amount of labeled wild-type or mutant MKP5-CD was combined with up to 200 μM 1 and loaded into premium capillaries. MST experiments were carried out at 40% IR power for 20 seconds. Normalized fluorescence ($F_{norm}$) values at a given time were plotted against inhibitor concentration, and the $K_d$ was determined by fitting with a hyperbolic binding curve. Experiments were performed in triplicate and data are presented as means±SD.

MKP5-CD constructs were diluted to a final volume of 400 μL in storage buffer were analyzed for CD absorption by an Applied Photophysics CHIRASCAN™ Circular Dichroism spectrophotometer Model 215 (AVIV Instruments, Inc.). Curves for each construct were normalized so that the minimum ellipticity is equal.

Phosphatase Activity Assays

Compound 1 selected from the screen was tested for activity against MKP1 and MKP5 using the malachite green assay. For MKP5-CD, the same conditions for the screening assay were used. For MKP1-CD, the following conditions were used: 1 μM MKP1-CD, 50 μM pTpY, 120 min at 30° C.

For para-nitrophenol phosphate (pNPP) activity assays against MKP5-CD and the MKP5-CD mutants, proteins were diluted to a working concentration and reactions were initiated with 40 μl pNPP in reaction buffer to a final concentration of 10 mM pNPP, 24 mM HEPES (pH 7.4), 120 mM NaCl, and 5 mM DTT. Reactions were incubated at 37° C. for 10 minutes, followed by quench with 1.450 ml of 200 mM NaOH. Reaction progress was assessed by measuring absorbance at 405 nm using a Beckman DU 530 UV/Vis Spectrophotometer and converted to turnover using an extinction coefficient of 17,800 $M^{-1}$ $cm^{-1}$.

Phosphate Sensor Kinetic Assay

The phosphate sensor protein (PS) was purchased from Life Technologies (Lot #1962036B). To characterize the activity of MKP5-CD against full length p38α MAPK, 5 nM MKP5-CD and 0.5 μM PS were combined in 50 mM Tris (pH 7.6), 25 mM NaCl, 0.01% Triton X100 and 0.5 μM DTT and added to a Corning #4511 384-well plate. Using an Echo 550 liquid handler (LabCyte Inc.), either 25 μM compound 1 or neat DMSO were added to a final DMSO concentration of 0.2%. Reactions were initiated with up to 300 μM p38α MAPK, a concentration approximately 5 times the $K_M$ of MKP5-CD39, and allowed to proceed at ambient temperature for 20 minutes. Fluorescence was continuously monitored by Tecan Infinite M1000 with excitation at 425 f 5 nm and emission at 454 f 5 nm. Raw fluorescence was converted to phosphate release using a standard curve generated the same day as kinetic experiments. The initial velocity was determined for each well based on reaction progress in the first 120 seconds. These velocities were then plotted against substrate concentration and fit to a mixed-mechanism inhibition curve.

Crystallization and Structure Determination

In order to co-crystallize wild-type MKP5-CD with 1, the compound was added to a concentration of 5 mM and allowed to bind overnight at 4° C. with shaking. Initial screening was carried out with Hampton Research Crystal Screen 1, Crystal Screen 2, and Index Screen. Subsequent rounds of optimization yielded the following crystallization conditions. Hanging drop vapor diffusion was used with the well solution 100 mM HEPES pH 7.5, 200 mM ammoniam acetate, 25% (w/v) PEG 3350 and a drop with a 4:1 volume of MKP5-CD:1 and well solution. Crystallization experiments were dispensed using a Mosquito (TTP Labtech) liquid handler and crystal growth was monitored using the RockImager R-1000 (Formulatrix). Thin plates formed within two days, were transferred to cryoprotectant of well solution plus 3% PEG 3350, and flash frozen in liquid nitrogen. Diffraction data were collected on the ADSC Q315r CCD detector at the NE-CAT 24-ID-E beamline at the Advanced Photon Source at Argonne National Laboratories. The data were collected to a resolution of 2.7 Å from a single crystal at a wavelength of 0.97918 Å. The data were indexed, integrated, and scaled using XDS41. The data was phased by molecular replacement with chain A of the MKP5-CD apo structure31 (PDB accession 1ZZW) with all waters and heteroatoms removed using Phaser. The structure was improved through rounds of refinement and model building using Phenix.Refine and Coot, respectively. Finally, the structure was validated with MolProbity. 99.9% of phi and psi angles are found in the favored or allowed regions of the Ramachandran plot. Contacts between 1 and MKP5-CD were identified with LigPlot+. Crystallographic data and refinement statistics are shown in Table 1.

The volume of the active site of MKP5 (i.e., the pocket containing Cys408) was determined using CAVER Analyst47 Cavity Computation tool. Cavities were defined by an inner probe of 1.05 Å, an outer probe of 5 Å and clipped by the sphere of radius 5 Å centered on the sulfur atom of Cys408. Active site volumes for wild-type MKP5-CD:1 and the apo structure of MKP531 were compared by two-tailed one-sample t-test.

Multiple Sequence Alignment and Structural Modeling

The primary sequences of twelve human DUSP PTP domains were obtained from Uniprot and aligned with Geneious (v10.2.2). Similarity to MKP5 was determined by BLOSUM62 score.

The structures of p38α MAPK (PDB accession 1R39) and MKP5-CD:1 were superposed on the structure of the complex of JNK1 and MKP7-CD34 (PDB accession 4YR8) or VHR (PDB accession 1J4X) using PyMOL. The root-mean-square deviations for these alignments were 1.903, 0.921, and 1.033 Å, respectively.

Cell Culture and Immunoblotting

C2C12 myoblasts were cultured as described previously. Substantively, wild type (mkp-$5^{+/+}$) and MKP5-deficient (mkp-$5^{-/-}$) mouse embryo fibroblasts (MEFs) were generated from female mice at days 13-14 of pregnancy and established by spontaneous immortalization. C2C12 myoblasts and MEFs were treated with 1 at the indicated concentrations for 24 h. For immunoblotting, C2C12 myoblasts or MKP5 wild type and MKP5-deficient fibroblasts were lysed on ice in lysis buffer and clarified by centrifugation at 20,800×g at 4° C. for 20 min. Protein concentration was determined using BCA reagent according to the manufacturer's instructions (Pierce). Recombinant human TGF-β1 (240-B-002) was purchased from R&D Systems. For phospho-MAPK and MAPK immunoblotting, lysates were resolved by SDS-PAGE and transferred onto nitrocellulose membranes (Bio-Rad). Membranes were blocked with 5% nonfat dry milk or 5% BSA in Tris-buffered saline/Tween 20 (TBS-T) for 1 h at room temperature or overnight at 4° C. Primary antibodies were diluted in 5% BSA or 5% nonfat dry milk in TBS-T. MAPK and Smad2 activation were calculated as the ratio of the indicated phosphorylated MAPK or phosphorylated Smad2 to total MAPK or Smad2, respectively by direct fluorescence quantitation using the Odyssey CLx Imaging System. Images were processed with the LI-COR Image Studio Software.

Animal Studies

MKP5 knockout mice were generated. Skeletal muscle injury was induced by intramuscular injection of 300 μl cardiotoxin (Sigma-Aldrich, 0.1 mg/ml in PBS) into the gastrocnemius/soleus muscles, after anesthesia by administration of 10 mg/kg ketamine and 1 mg/kg xylazine. Soleus muscle from uninjured and at 4 and 10 days after injury was removed and rapidly frozen in liquid nitrogen and stored at −80° C. for subsequent biochemical analyses. For immunoblotting, soleus muscles were homogenized and lysed on ice in lysis buffer containing 100 mM Tris HCl (pH 7.4) and 25 mM EDTA. C2C12 myoblasts were lysed on ice in lysis buffer. Tissue or cell lysates were incubated at 4° C. for 30 min and clarified by centrifugation at 14,000 rpm at 4° C. for 10 min. Lysates were resolved by SDS-PAGE, transferred to nitrocellulose membranes and immunoblotted with either antibodies to either Smad2 or phospho-Smad2. Differences between genotypes were assessed by a Student's t test or analysis of variance (ANOVA) with Tukey's multiple comparisons test using Prism software (GraphPad Software).

STEP-46 and PTP1B Counterscreens

To test for 1 activity on STEP-46, a pNPP assay was employed with 1.5 μM STEP46 and 10 mM pNPP. After 30 min at room temperature, absorbance at 405 nm was measured. For comparison, MKP5-CD was tested in the pNPP assay under identical conditions. For PTP1B, the Millipore PTP1B assay kit (#539736) was performed as recommended by the manufacturer except that malachite green was used for detection.

Scheme 1: Synthesis of 1

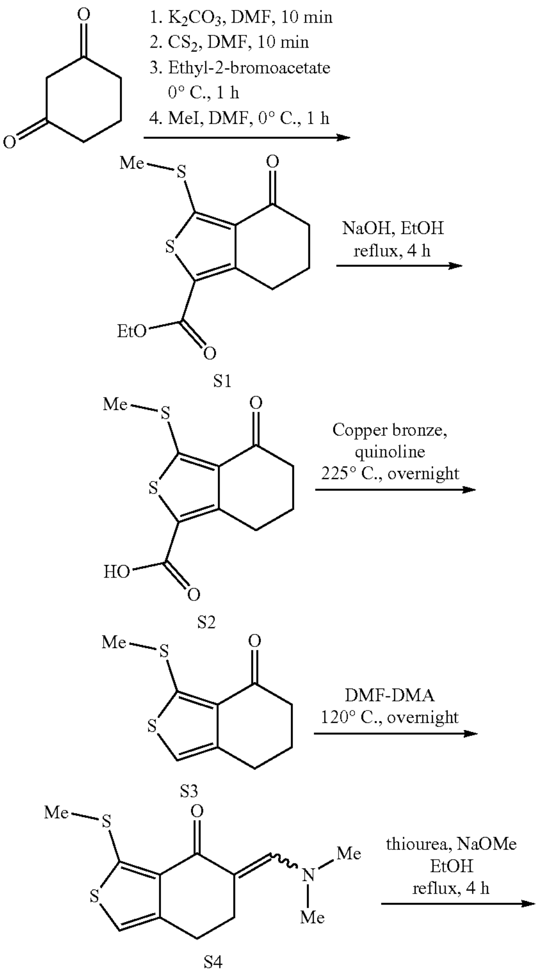

S1

S2

S3

S4

-continued

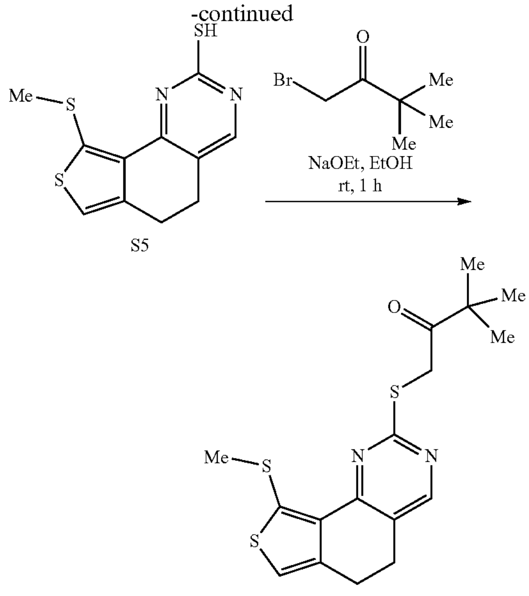

S5

1

Intermediate S1: Intermediate S1 was synthesized as described in the literature. Briefly, a 250-mL round bottomed flask was equipped with a stir bar and charged with $K_2CO_3$ (20.7 g, 150 mmol, 3.00 equiv) and DMF (45 mL). Next, 1,3-cyclohexane dione (5.60 g, 50.0 mmol, 1.00 equiv) was added to the flask, and the slurry was stirred at room temperature for 10 min. Next, carbon disulfide (5.70 g, 4.53 mL, 75.0 mmol, 1.50 equiv) was added to the flask at once and the resulting mixture was stirred at room temperature for 10 additional min. The mixture was cooled to 0° C. and subsequently ethyl-2-bromoacetate (8.34 g, 5.53 mL, 50.0 mmol, 1.00 equiv) was added in DMF (50 mL) dropwise via addition funnel. The reaction mixture stirred at 0° C. for 1 h. Finally, methyl iodide (7.80 g, 3.42 mL, 55.0 mmol, 1.10 equiv) in DMF (20 mL) was added dropwise via addition funnel. The reaction mixture was stirred at 0° C. for an additional 30 min. The reaction mixture was next poured into water (900 mL) and vigorously stirred overnight. The crude product was collected by filtration, and the residue was purified by normal phase chromatography (0-70% ethyl acetate in hexanes) to yield dark orange oil (8.50 g, 63% yield) that was used without further purification. $^1$H-NMR (400 MHz, $CDCl_3$): δ 4.26 (q, J=7.1 Hz, 2H), 3.11 (t, J=6.2 Hz, 2H), 2.53 (s, 3H), 2.47 (t, J=6.7 Hz, 2H), 1.98 (pent, J=6.2 Hz, 2H), 1.31 (t, J=7.1 Hz, 3H). $^{13}$C-NMR (101 MHz, $CDCl_3$): δ 194.0, 161.5, 159.5, 151.2, 131.2, 121.9, 60.9, 38.5, 26.2, 22.9, 18.0, 14.4. HRMS (For $C_{12}H_{15}O_3S_2$, MH+): Calc'd 271.0463, found 271.0465.

Intermediate S3: A 250-mL round-bottomed flask was charged with compound S1 (7.00 g, 26.0 mmol, 1.00 equiv.), which was subsequently dissolved in ethanol (175 mL). Sodium hydroxide (1.29 g, 32.4 mmol, 1.25 equiv) was added to the flask, and the reaction mixture was heated to reflux for 4 h. At this time, the solvent was removed under vacuum, and the crude residue was acidified with cold 3M HCl (60 mL). This aqueous solution was stirred at room temperature for 1 h. At this time, the product was collected by filtration, which was placed under vacuum for 2 h. The resulting beige solid S2 (5.60 g, 89% yield) was used without further purification. The subsequent procedure for the synthesis of S3 was adapted from the literature. A 15-mL high-pressure tube was equipped with a stir bar and charged with compound S2 (2.00 g, 6.20 mmol, 1.00 equiv) and copper bronze (3.30 g). The reaction vessel was sealed with a rubber stopper and subsequently evacuated and back-filled with nitrogen three times by a needle inlet. Freshly distilled and degassed quinoline (5 mL) was added, and the rubber stopper was quickly replaced by the high-pressure tube cap. The reaction vessel was heated to 225° C. in a pre-equilibrated sand bath and stirred at this temperature overnight. At this time, the reaction mixture was cooled to room temperature and filtered through Celite, washing 2× with $CH_2Cl_2$ (20 mL). The mixture was diluted with an additional 150 mL of $CH_2Cl_2$ and subsequently washed with 3M HCl (4×, 40 mL) and brine (2×, 40 mL). The organic layer was collected, dried over $Na_2SO_4$, and concentrated. Product S3 was subsequently purified by normal-phase chromatography (0-30% diethyl ether in hexanes) to yield an orange liquid (550 mg, 45% yield) that was used without further purification. $^1$H-NMR (400 MHz, $CDCl_3$): δ 6.74 (s, 1H), 2.79 (t, J=6.0 Hz, 2H), 2.56 (s, 3H), 2.62 (t, J=6.2 Hz, 2H), 2.00 (pent, J=6.0 Hz, 2H). 13C-NMR (101 MHz, $CDCl_3$): δ 194.0, 153.1, 143.5, 130.6, 115.1, 39.1, 26.5, 23.6, 18.0. HRMS (For $C_9H_{11}OS_2$, MH+): Calc'd 199.0253, found 199.0253.

Intermediate S4: A round-bottomed flask was equipped with a stir bar and charged with compound S3 (500 mg, 2.51 mmol, 1.00 equiv). Dimethylformamide dimethyl acetal (3.59 g, 4.00 mL, 30.1 mmol, 12.0 equiv) was added to the flask. The reaction flask was then equipped with a reflux condenser and the mixture was heated at 120° C. overnight. At this time, the reaction mixture was allowed to cool to room temperature and concentrated under vacuum. The crude residue was purified by normal phase chromatography (0-15% MeOH in $CH_2Cl_2$) to yield a dark brown oil (439 mg, 69% yield), which was used without further purification. The product was isolated as a mixture of two inseparable diastereomers in a 3:1 ratio. $^1$H-NMR (400 MHz, $CDCl_3$): Major diastereomer: (400 MHz, $CDCl_3$): δ 7.54 (s, 1H), 6.66 (s, 1H), 3.05 (s, 6H), 2.81 (t, J=5.7 Hz, 2H), 2.70 (t, J=6.0 Hz, 2H), 2.52 (s, 3H). Minor diastereomer: δ 7.54 (s, 1H), 6.66 (s, 1H), 3.07 (s, 6H), 2.84 (t, J=6.8 Hz, 2H), 2.70 (t, J=6.0 Hz, 2H), 2.54 (s, 3H). 13C-NMR (101 MHz, $CDCl_3$): Major diastereomer: δ 183.8, 162.1, 149.7, 142.4, 132.1, 114.1, 104.1, 43.6, 26.4, 24.7, 18.2. Minor diastereomer: δ 183.4, 156.2, 150.3, 149.0, 133.1, 120.1, 130.0, 60.7, 25.7, 23.9, 14.5. HRMS (For $C_{12}H_{16}NOS_2$, MH+): Calc'd 254.0673, found 254.0674.

Intermediate S5: A three-necked round bottomed flask was equipped with a stir bar and subsequently evacuated and refilled with nitrogen three times. Under positive $N_2$ pressure, the flask was charged with S4 (1.00 g, 3.95 mmol, 1.00 equiv) and thiourea (451 mg, 5.92 mmol, 1.50 equiv). Freshly degassed EtOH (15 mL) was added via syringe to the reaction flask. Finally, under positive $N_2$ pressure, NaOMe (426 mg, 7.89 mmol, 2.00 equiv) was added, and the reaction flask was sealed and heated to 80° C. until TLC analysis showed disappearance of the starting materials (4 h). At this time, the reaction mixture was cooled and glacial acetic acid (2 mL) was added to prevent dimerization of the resulting thiol product, resulting in precipitation of a brown solid. The product (458 mg, 44% yield) was collected by filtration, washing with EtOH, and was used without further purification. $^1$H-NMR (400 MHz, DMSO-$d_6$): δ 13.20 (bs, 1H), 7.82 (s, 1H), 7.20 (s, 1H), 2.78 (t, J=7.3 Hz, 2H), 2.67 (t, J=7.4 Hz, 2H), 2.58 (s, 3H). $^{13}$C-NMR (101 MHz, DMSO-$d_6$): δ 179.1, 160.4, 149.1, 142.1, 140.9, 127.1, 116.7, 116.5, 24.2, 24.0, 18.0. HRMS (For $C_{11}H_{11}N_2S_3$, MH+): Calc'd 267.0084, found 267.0081.

Inhibitor 1: A round bottomed flask was equipped with a stir bar, charged with S5 (24.0 mg, 0.0900 mmol, 1.00 equiv), and subsequently evacuated and refilled with nitrogen three times. Freshly degassed EtOH (1 mL) and 1-bromopinacolone (17.7 mg, 13.3 μL, 0.0990 mmol, 1.10 equiv) were added via syringe. Finally NaOEt (21% in EtOH, 12.3 mg, 58.2 μL, 2.00 equiv) was added to the reaction mixture, which was stirred at room temperature for 1 h. The reaction mixture was concentrated and purified by normal phase chromatography (0-30% ethyl acetate in hexanes) to yield an off-white solid (24.0 mg, 73% yield). $^{1}$H-NMR (400 MHz, $CDCl_3$): δ 8.28 (s, 1H), 6.86 (s, 1H), 4.59 (s, 2H), 2.89-2.83 (m, 2H), 2.83-2.77 (m, 2H), 2.63 (s, 3H), 1.27 (s, 9H). $^{13}$C-NMR (101 MHz, $CDCl_3$): δ 209.7, 169.2, 158.3, 155.5, 144.5, 140.8, 128.6, 122.9, 116.2, 44.6, 38.8, 26.9, 25.5, 25.0, 18.6. HRMS (For $C_{17}H_{21}N_2OS_3$, MH+): Calc'd 365.0816, found 365.0824.

Example 1: High-Throughput Screen Identifies an Inhibitor of MKP5

When MKP5-deficient mice were intercrossed with a mouse model of Duchenne muscular dystrophy (mdx), these mice were protected from the development of dystrophic muscle disease accompanied by a marked diminution in skeletal muscle fibrosis. These results show that inactivation of MKP5 can serve as a therapeutic strategy for the treatment of dystrophic muscle disease. Thus, potential MKP5 inhibitors were sought. Previous efforts to identify inhibitors of PTPs and DUSPs have utilized small molecule mimics of phosphotyrosine (e.g., para-nitrophenyl phosphate, pNPP) as substrates. Accordingly, hits from these screens were predominantly negatively charged compounds that exhibited poor specificity and lacked drug-like characteristics.

Figure 1B:
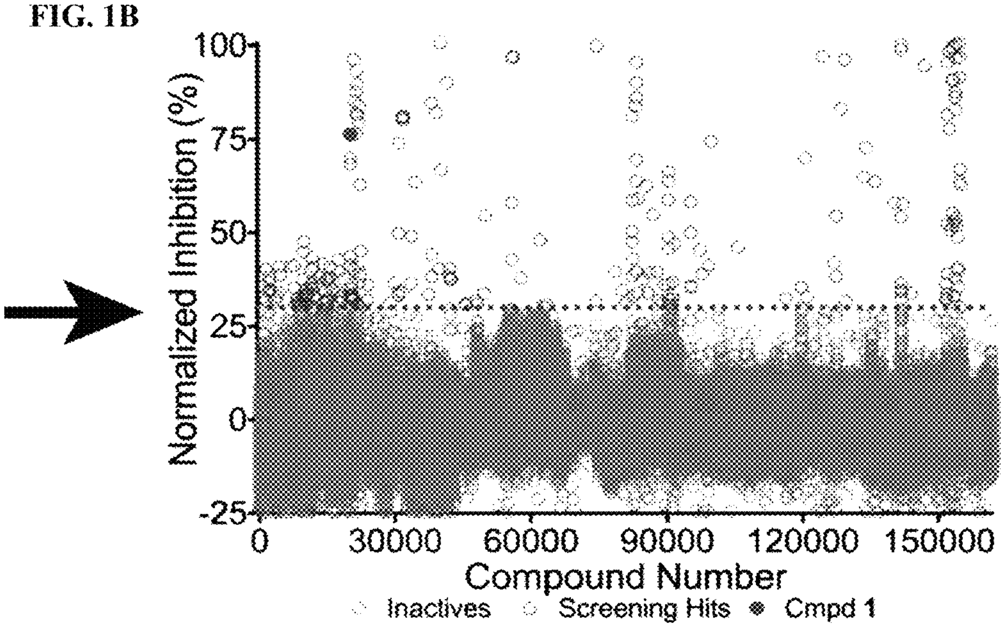
Figure 14:
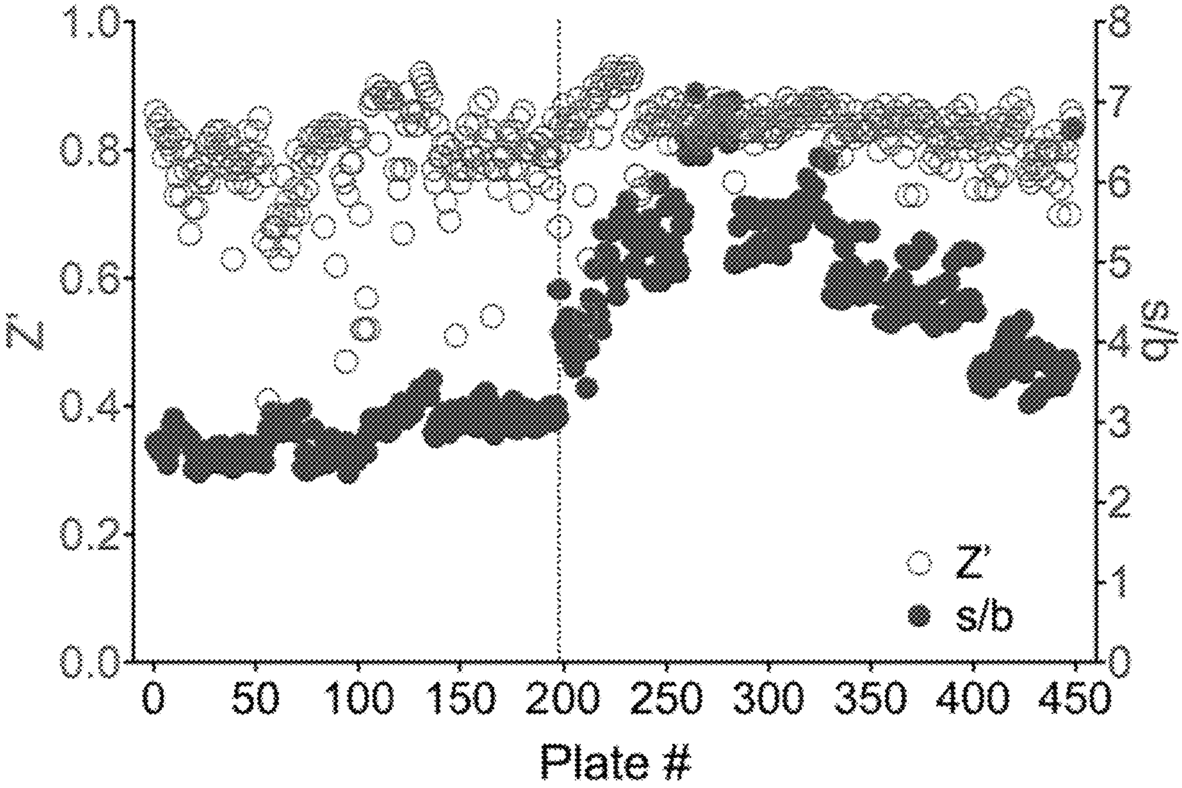
FIG. 14 depicts statistics for high-throughput screen of small molecules. Z' (light grey) and signal-to-background ratio (s/b, dark grey) are plotted for each plate in the high throughput screen. Screen was carried out in two phases, separated by the dotted vertical line at plate #199.

In order to increase the likelihood of identifying compounds that bind at sites distinct from the MKP5 catalytic pocket, a modified 11 amino acid dually-phosphorylated peptide was chosen (Asp-Asp-Glu-Nle-pThr-Gly-pTyr-Val-Ala-Thr-Arg) (SEQ ID NO: 15) encompassing the pThr180-Gly-pTyr182 motif of p38α MAPK present on the activation loop of p38α MAPK, which represents the primary MKP5 substrate. An optimized high-throughput malachite green phosphatase assay was developed. The effect of compounds from commercial and proprietary libraries on the phosphatase activity of the catalytic domain of MKP5 (MKP5-CD, residues 320-467) were quantified against the p38α MAPK phosphopeptide substrate (FIG. 1A). The resultant screen yielded a Z' value of 0.7-0.8 (FIG. 14) and identified 391 compounds that inhibited MKP5-CD by more than 30% (FIG. 1B).

Figure 1C:
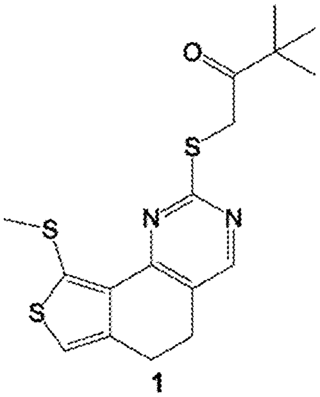
Figure 15A:
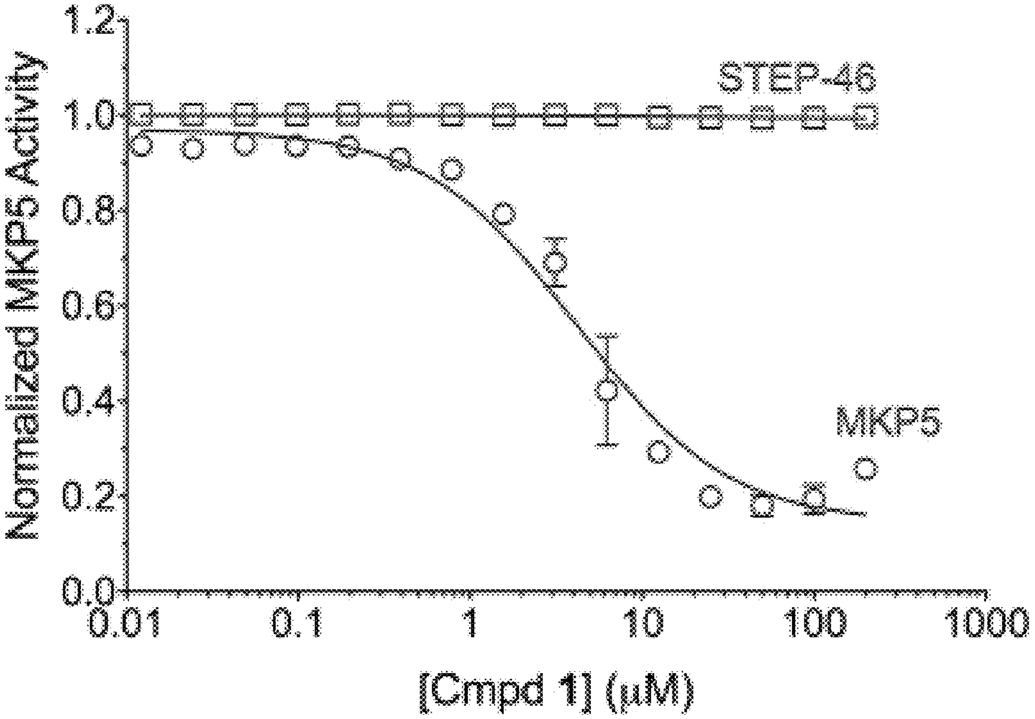
FIGS. 15A-15B show that 1 does not inhibit STEP-46 or PTP1B.
Figure 15B:
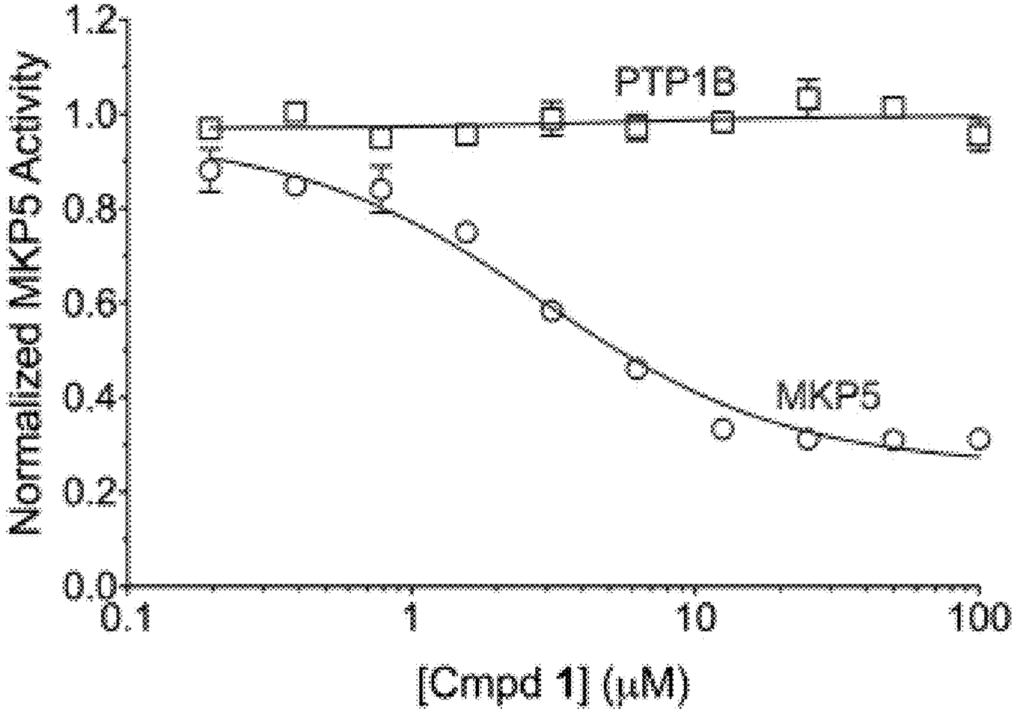

The 391 compounds were retested, analyzed for assay interference and checked for historical promiscuity in high throughput screens. Following this triage, 27 compounds were assayed for selectivity for DUSPs as compared with PTPs. The compounds were tested for inhibition of the 46 kDa isoform of the striatal-enriched PTP (STEP-46) and PTP-1B. 3,3-Dimethyl-1-((9-(methylthio)-5,6-dihydrothieno[3,4-h]quinazolin-2-yl)thio)butan-2-one (Compound 1, FIG. 1C), displayed differential activity between MKP5-CD (half-maximal inhibitory concentration, $IC_{50}$~4.2 μM), STEP-46 ($IC_{50}$>200 μM), and PTP-1B ($IC_{50}$>100 μM) (FIG. 15). As such, 1 was designated as the lead hit. In order to carry out all further studies, 1 was resynthesized according to Scheme 1.

Figure 1E:
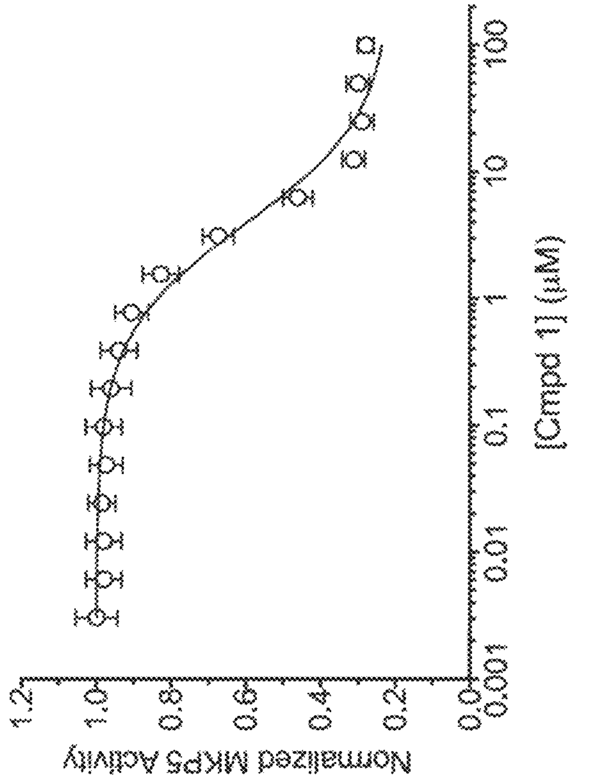
Figure 1D:
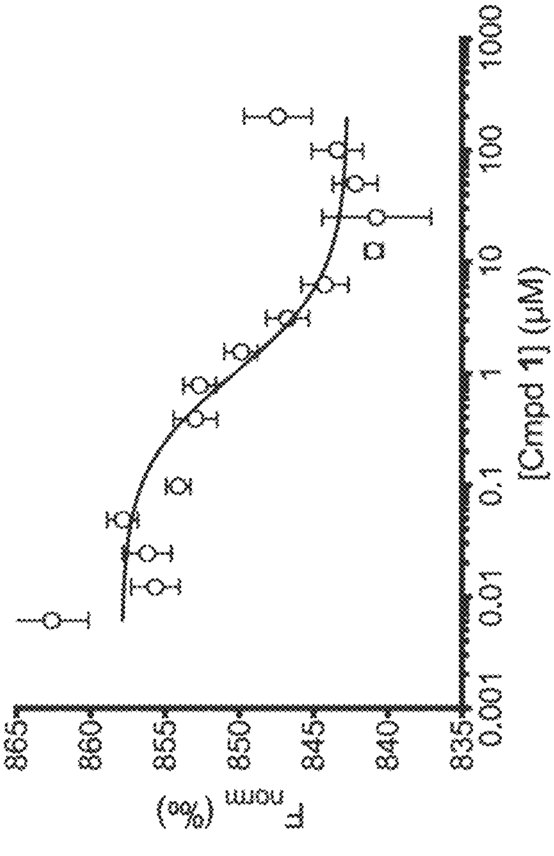
Figure 1G:
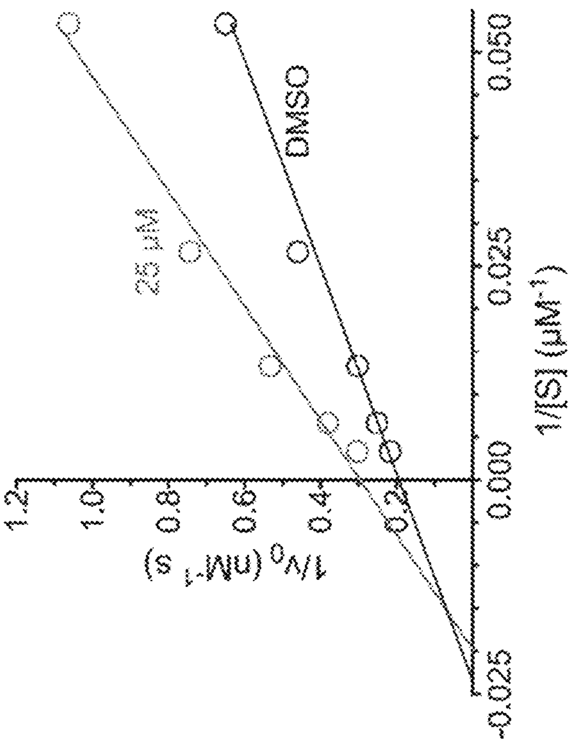
Figure 1F:
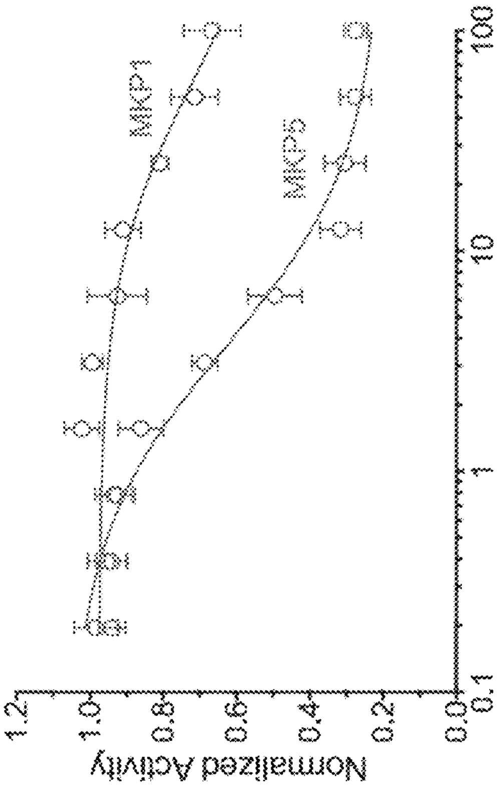
Figure 16:
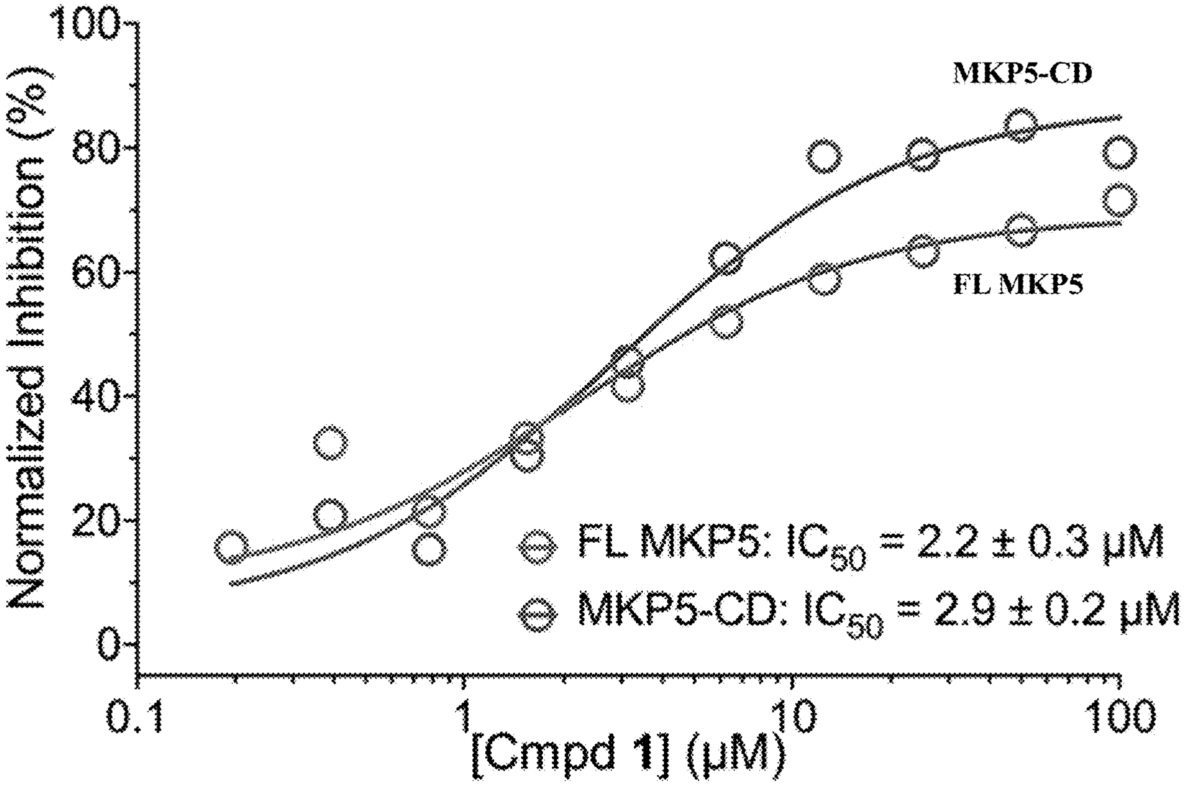
FIG. 16 shows that 1 inhibits full-length MKP5. Inhibition of full length MKP5 (blue) and MKP5-CD (red) depicted as percentage loss of activity relative to DMSO control. $IC_{50}$ was determined by fitting to a hyperbolic inhibition curve. Data are represented as mean±SD and are the product of three independent experiments.
Figure 17:
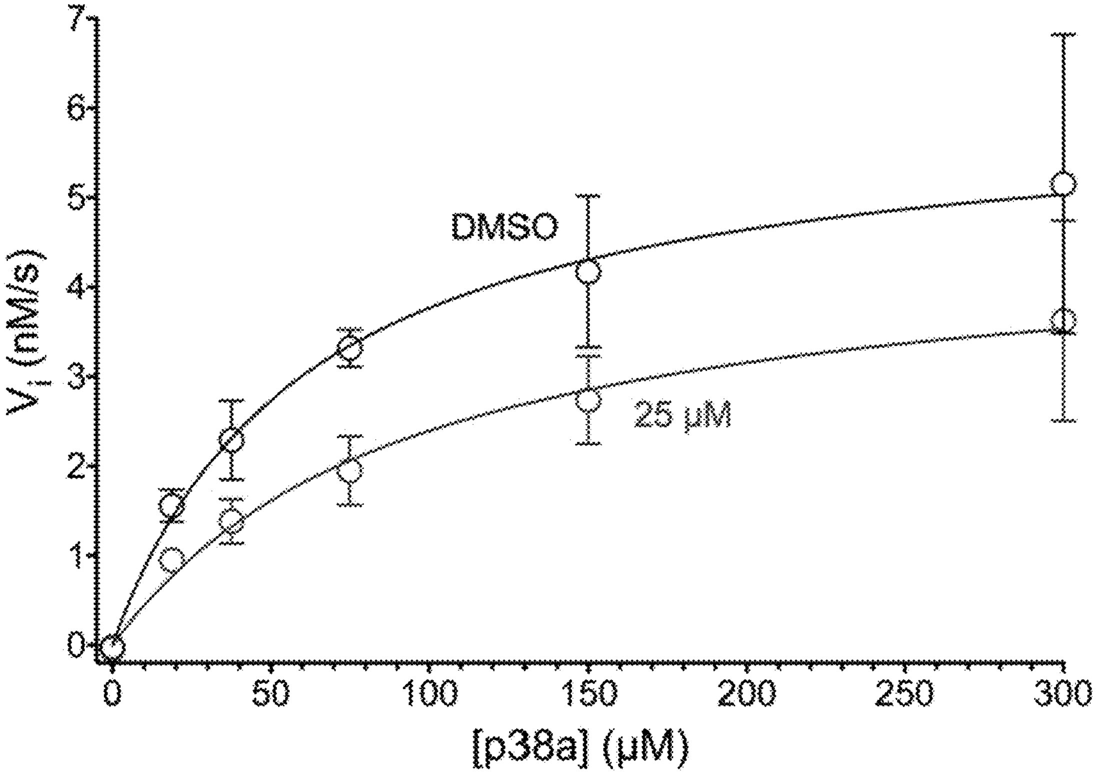
FIG. 17 depicts a non-linear regression for the inhibition of MKP5-CD by 1. Data are fitted to a mixed-mechanism inhibition equation to determine the effect of 1 on apparent $K_M$ and $V_{max}$. Data are presented as mean±SD and are the product of three independent experiments.

To further characterize 1, a microscale thermophoresis assay using MKP5-CD was carried out to determine the binding affinity of 1 for MKP5. Using fluorescently-labeled MKP5-CD, a dissociation constant ($K_d$) of 1.0±0.2 μM was found (FIG. 1D). The potency of 1 was determined by malachite green assay using the p38α MAPK phosphopeptide as a substrate, which yielded an $IC_{50}$ of 3.9±0.6 μM (FIG. 1E). 1 was also found to inhibit the full-length MKP5 with similar potency to the catalytic domain (FIG. 16). In order to demonstrate the selectivity of 1, its ability to inhibit MKP5 was directly compared to that of MKP1, which has a highly similar PTP domain. The $IC_{50}$ of 1 towards the catalytic domain of MKP1 was found to be above 60 μM, displaying a 16-fold reduction in potency relative to that of MKP5 (FIG. 1F). Taken together, these results identify 1 as a highly selective inhibitor of MKP5 likely due to direct binding to MKP5-CD. To determine the mode of inhibition of 1 against MKP5, a kinetic assay based on the fluorescence of tagged phosphate-sensing protein using purified recombinant full-length dually-phosphorylated p38α MAPK as a substrate was used (FIG. 1G, FIG. 17). By measuring the initial velocities of phosphatase activity of MKP5-CD in the presence of a concentration of inhibitor shown to display maximal inhibition in the potency assays (25 μM) and varying concentrations of p38α MAPK, it was possible to determine the effect of 1 on the kinetics of catalysis. When these data were fit to a mixed-mechanism inhibition curve, it was found that 1 displays a mixed competitive mode of inhibition (α≈4.6), whereby the Michaelis constant ($K_M$) is increased and maximal velocity ($V_{max}$) is decreased.

Crystal Structure of MKP5-CD in Complex with 1

Figure 18:
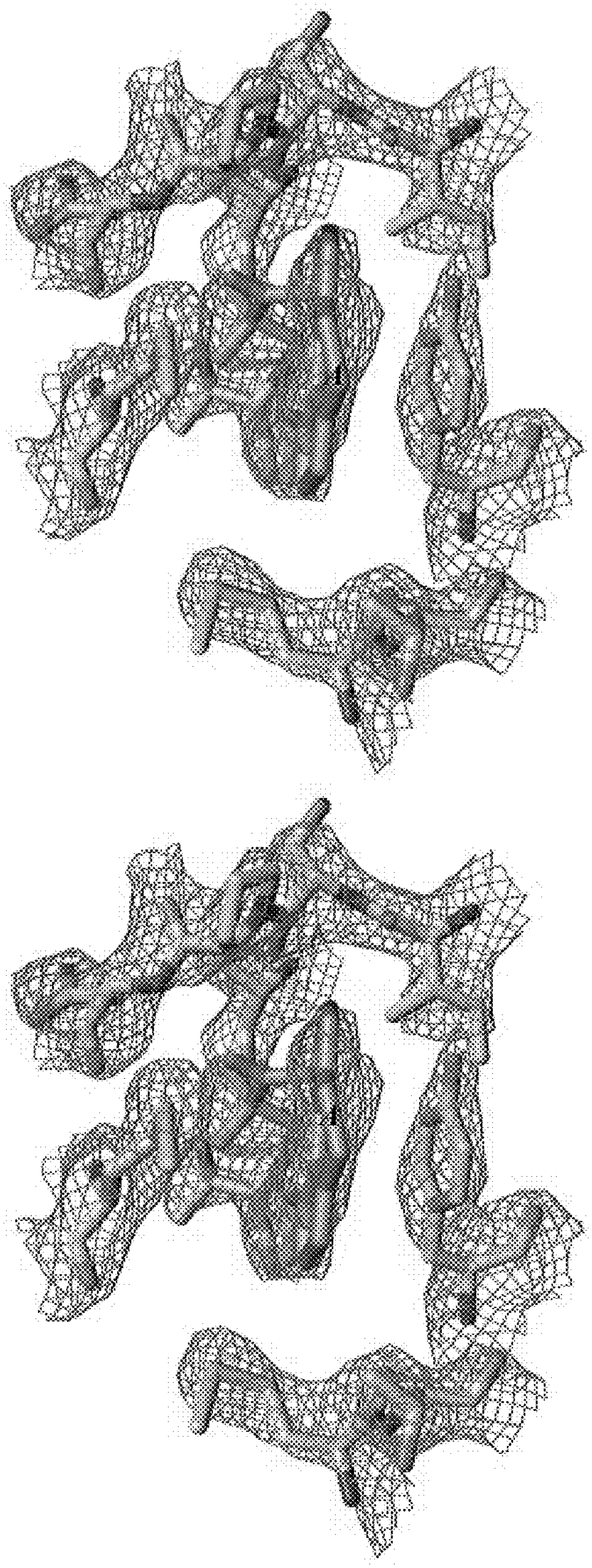
FIG. 18 depicts a stereoview of MKP5-CD in complex with 1 (A) in omit map (s=1.0).

The apo structure of MKP5-CD has been solved previously. Therefore, to further shed light on the mechanism of inhibition of 1, the structure of MKP5-CD bound to 1 was solved at 2.7 Å resolution with an $R_{free}$ of 0.227 (Table 1, FIG. 18).

TABLE 1

Crystallographic Data.

| | MKP5-CD:1 |
|---|---|
| Data collection | |
| Space. group | P 1 $2_1$ 1 |
| Cell dimensions | 66.1, 129.4, 83.3 |
| a, b, c (Å) | 90.0, 91.8, 90.0 |
| α, β, γ (°) | |
| Resolution (Å) | 47.4-2.7 (2.797-2.70) |
| $R_{sym}$ | 0.2009 (1.77) |
| $CC_{1/2}$ | 0.982 (0.504) |
| I/σI | 7.91 (1.51) |
| Completeness (%) | 99.7 (99.7) |
| Redundancy | 3.7 (3.7) |
| Refinement | |
| Resolution | 47.4-2.7 (2.797-2.70) |
| No. Reflections | 38344 (3819) |
| $R_{work}/R_{free}$ | 0.1881/0.2273 (0.3291/0.3682) |
| No. atoms | 7294 |
| Protein | 7112 |
| Ligand | 182 |
| B-factors ($Å^2$) | 50.3 |
| Protein | 49.9 |
| Ligand | 66.1 |
| R.m.s. deviations | |
| Bond lengths (Å) | 0.006 |
| Bond angles (°) | 0.87 |

Figure 2A:
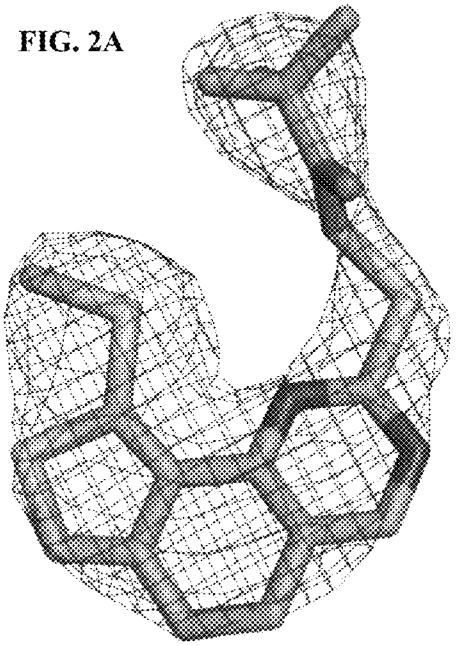
FIGS. 2A-2G show aspects of the X-ray crystal structure of MKP5-CD in complex with 1.
Figure 2B:
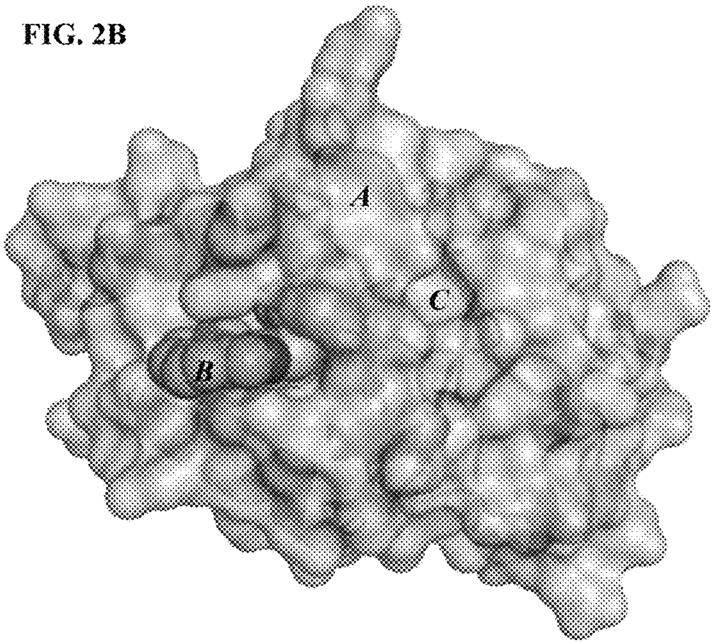
Figure 2C:
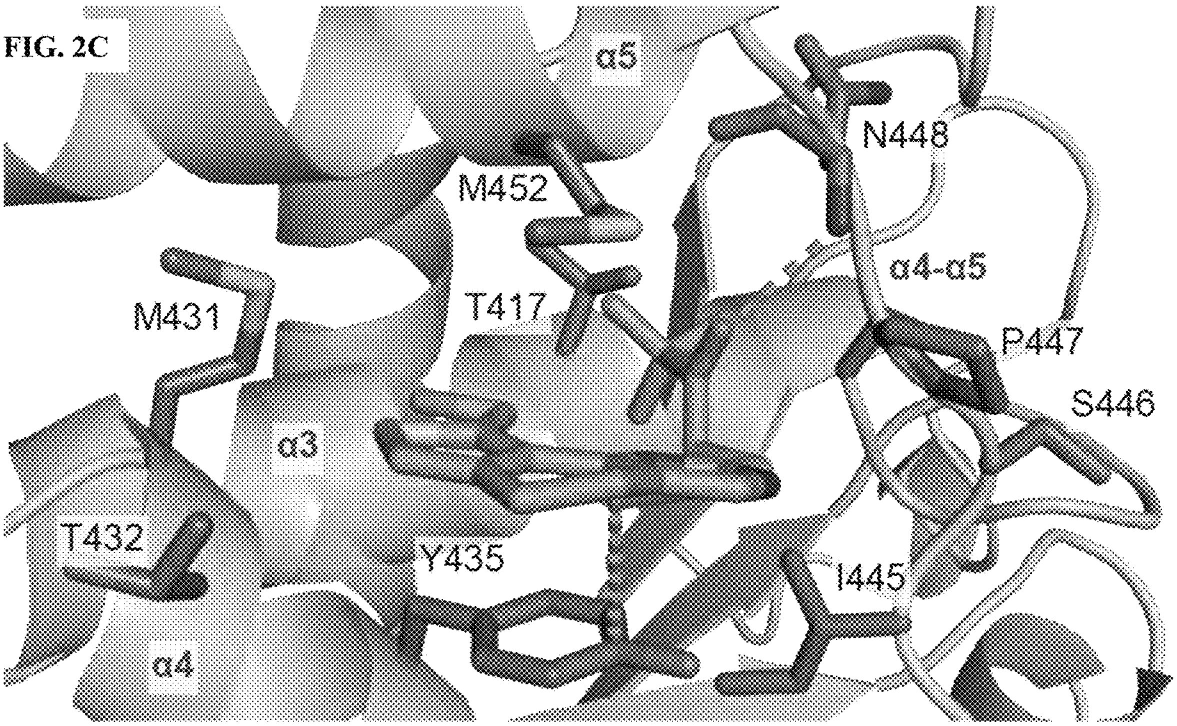
Figure 2D:
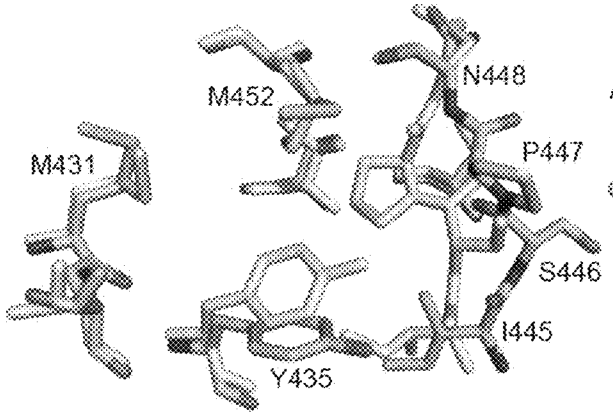
Figure 2E:
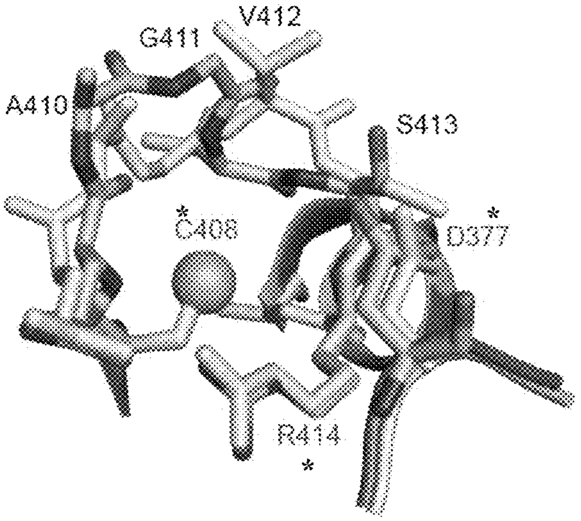
Figure 2F:
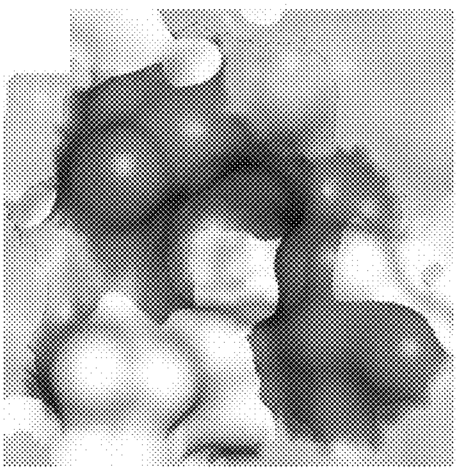
Figure 2G:
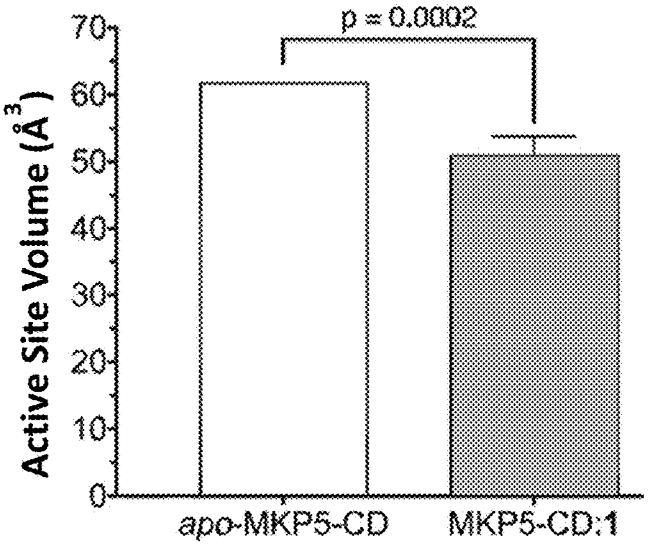

The asymmetric unit contains six monomers with nearly identical conformations. Electron density for the inhibitor molecule was well-defined and found in all six polypeptide chains (FIG. 2A). Remarkably, it was found that 1 binds an allosteric site formed by the alpha helices α3, α4, and α5, as well as the α4-α5 loop (FIG. 2B). This pocket, located approximately 8 Å from the catalytic sulfhydryl of Cys408, has not previously been described, though residues on helices α4 and α5 have been demonstrated to be important for JNK binding. Key interactions between 1 and MKP5 include a parallel-displaced π-stacking interaction with Tyr435 and a hydrogen bond with the backbone amide of Asn448 (FIG. 2C). The compound also makes extensive hydrophobic interactions with many residues, including Tyr435, Pro447, and Met452. Despite binding in an allosteric site, 1 forms hydrophobic interactions with Ser413 of the β35-α3 loop, which forms part of the catalytic pocket. In the highest-resolution crystal structure of apo-MKP5-CD available, two polypeptide chains adopt similar, but not identical conformations. The first chain is described as taking an active conformation similar to that seen in other DUSPs. There are multiple differences between the structure of the MKP5-CD-1 complex and the apo active conformation. The most striking of these differences is the movement of the residues 445ISP447 in the α4-α5 loop, where the peptide backbone shifts 3.7 Å to accommodate the incoming inhibitor (FIG. 2D). As part of this movement, the sidechain of Pro447 flips out of the pocket, moving ~6.5 Å. Other residues in the allosteric site move to better interact with 1, including Tyr435, which rotates and shifts to allow its ring-stacking interaction with the compound. The shift in the α4-α5 loop forces the β5-α3 loop, which forms the catalytic site, to compensate and change conformation as well (FIG. 2E). While the positions of the catalytic residues Cys408, Asp377, and Arg414 are not significantly affected, there is a major reorganization in the backbone leading to the displacement of residues 410AGVS413 (SEQ ID NO: 17). As a result of this shift in conformation, the volume of the active site pocket decreases by nearly 18% (FIG. 2F-2G, Table 2). Molecular dynamics simulations of MKP5-CD performed previously indicate that these shifts are unlikely to occur in solution in the absence of inhibitor.

TABLE 2

Active site volumes in MKP5-CD:1 and apo-MKP5-CD. Active site volumes determined using CAVER Analyst. Mean ± SD given for MKP5-CD:1 along with individual values.

| Structure | Resolution (Å) | Active Site Volume ($Å^3$) | |
|---|---|---|---|
| MKP5-CD:1 | 21 | 51.0 ± 2.8 | |
| Chain A | | | 51.0 |
| B | | | 47.7 |
| C | | | 53.8 |
| D | | | 53.9 |
| E | | | 52.0 |
| F | | | 47.8 |
| 1ZZW Chain A | 1.6 | 61.9† | |

†refers to single value

Figure 3A:
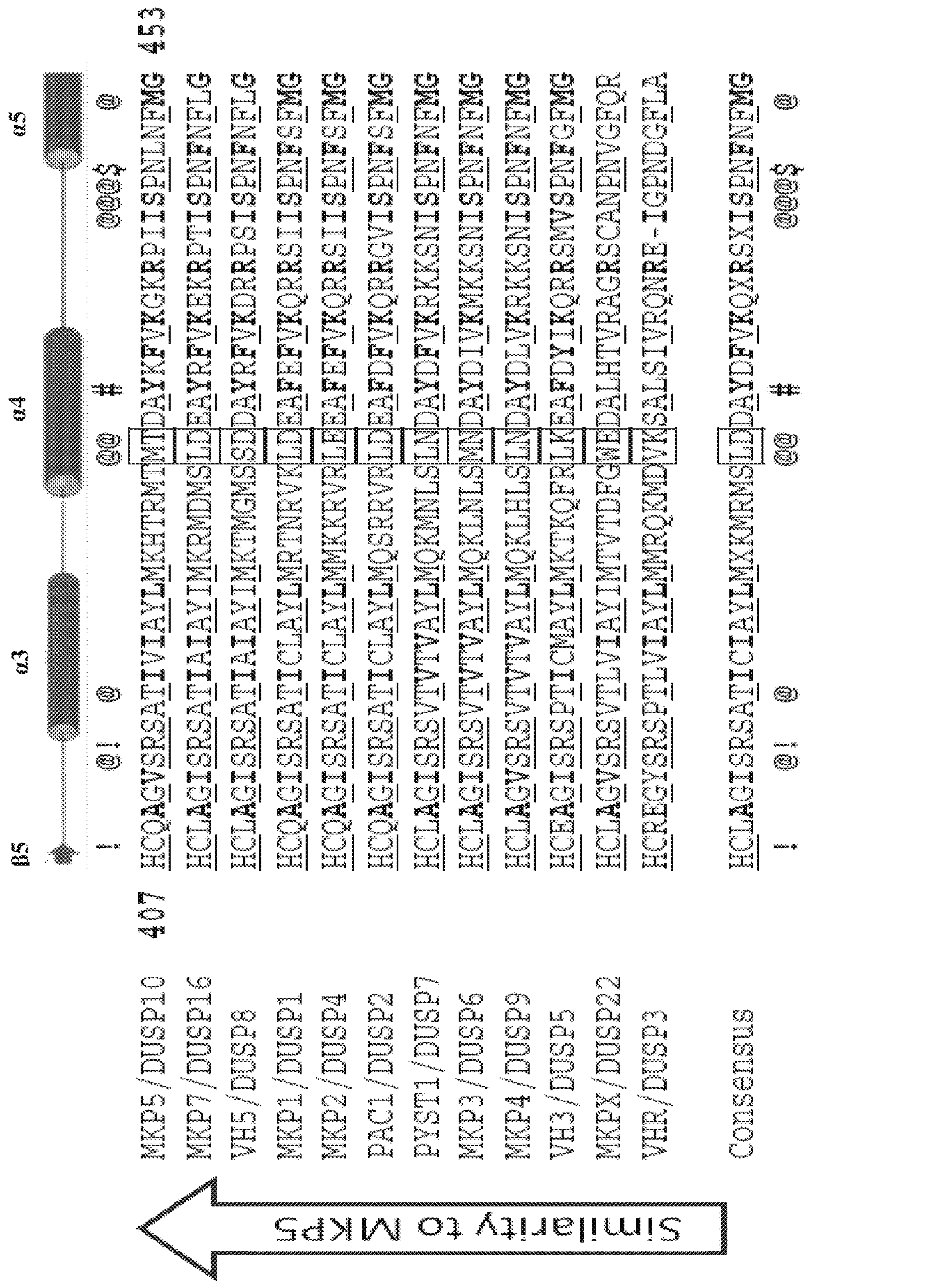
FIGS. 3A-3C show that the allosteric pocket of MKP5-CD contains residues critical for catalysis and inhibitor binding.

MKP5 Allosteric Site Contains Unique Residues Amongst an Otherwise Conserved Region While the data demonstrating a 16-fold difference in the potency of 1 between MKP5 and MKP1 likely due to targeting this allosteric site, specificity among DUSPs remains a concern. In order to determine whether 1 inhibits other DUSPs a sequence alignment of the catalytic domains of twelve such enzymes was performed (FIG. 3A). The other DUSP PTP domains are between 36 and 57% identical to that of MKP5, with the other stress-activated MAPK-specific MKPs (MKP7 and DUSP8) displaying the highest degree of similarity. Many of the residues in MKP5 that interact with 1 are well-conserved through the DUSPs, with 8 of 10 residues bearing significant similarity, including Tyr435. An aromatic residue is nearly always found at this position, suggesting in a non-limiting embodiment that this residue can play a role in either MKP5 enzymatic activity and/or inhibitor binding.

Figure 3B:
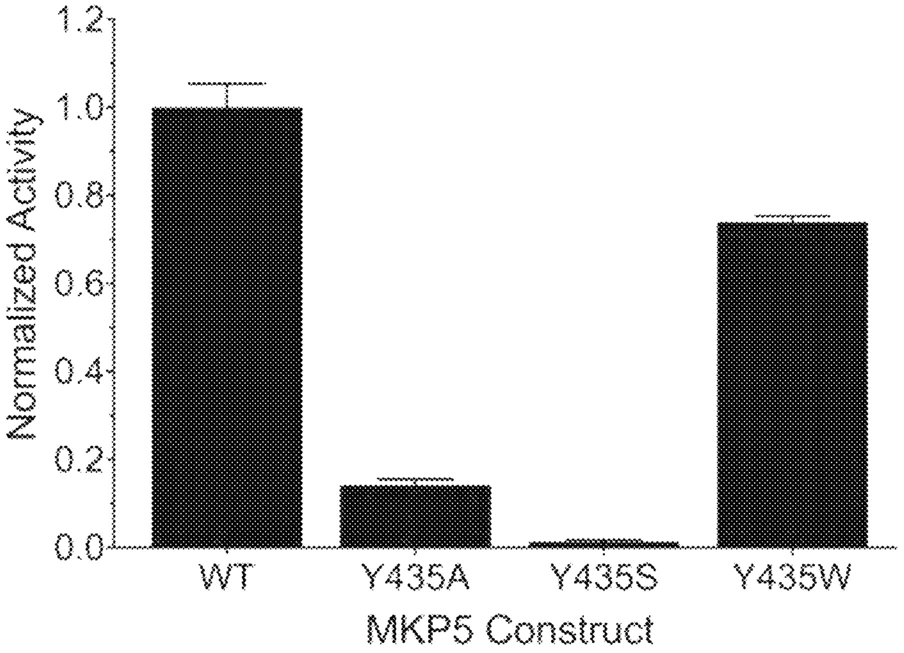
Figure 3C:
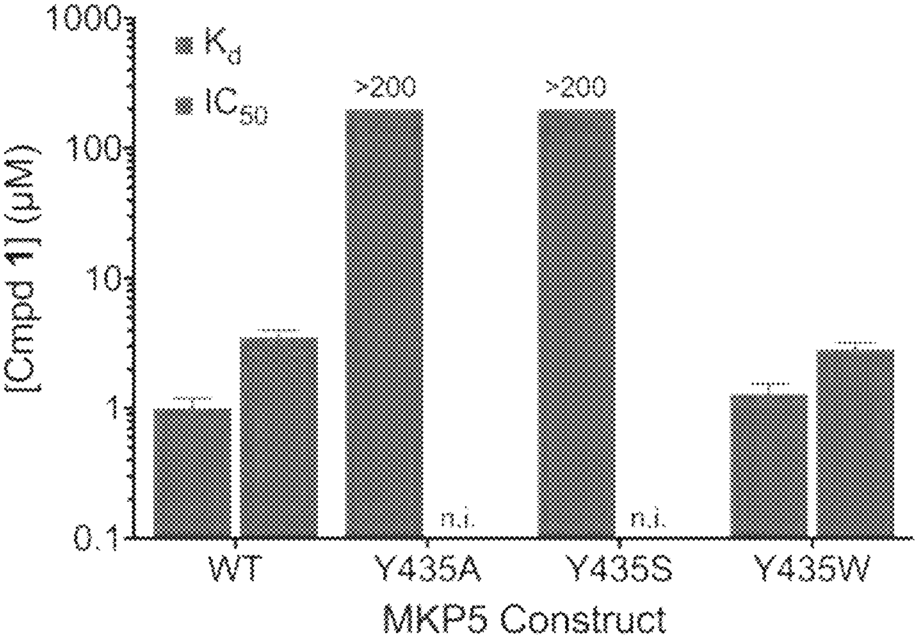
Figure 19:
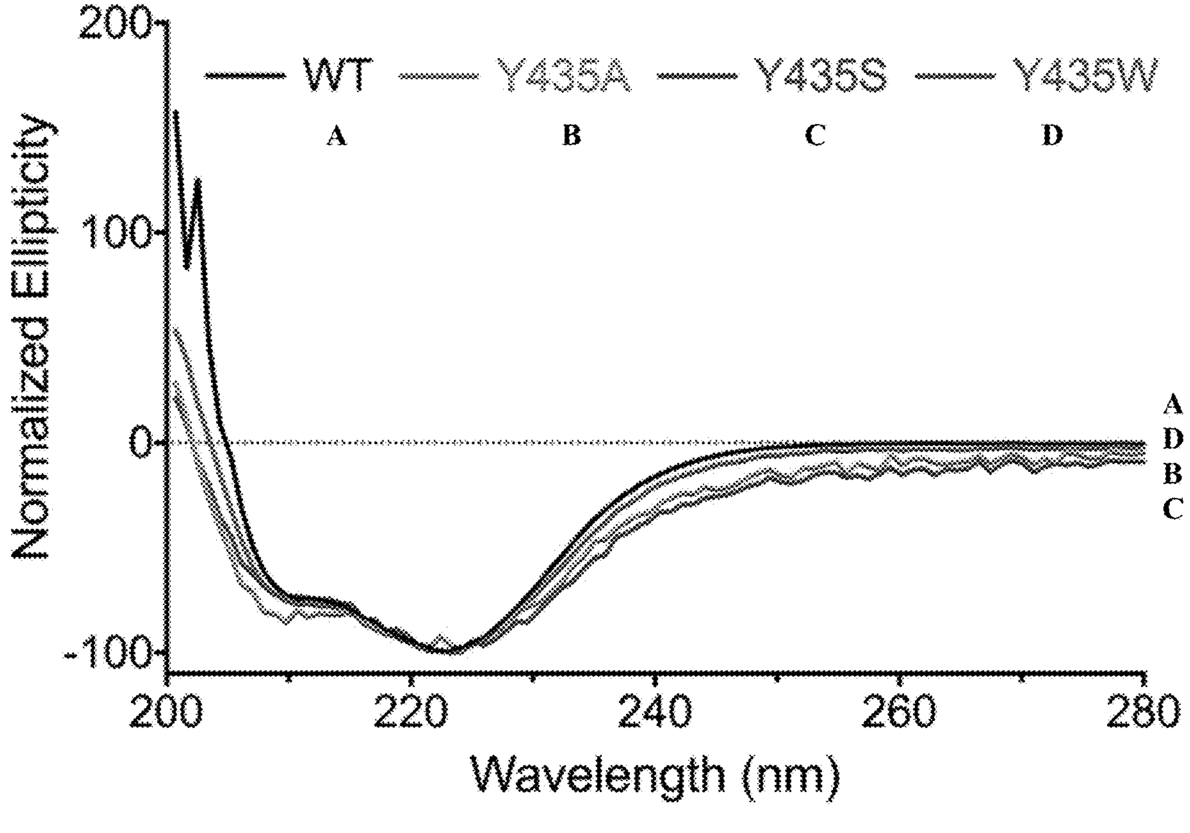
FIG. 19 shows that the Y435 Mutant MKP5-CD constructs fold properly. The folding state of wild-type, Y435A, Y435S, and Y435W MKP5-CD were determined by circular dichroism. Data are normalized so as to be on the same scale.

To investigate the importance of the allosteric pocket for the specific inhibition of MKP5, mutants of Tyr435, a potential key residue that contributes to the binding of 1 were generated and their enzymatic activity and capacity for inhibition by 1 was characterized. Tyr435 is well-conserved as an aromatic residue in nearly all DUSPs and as indicated contributes to a n-stacking interaction with 1. Tyr435 was replaced with either alanine, serine, or tryptophan. While all three mutant constructs fold properly (FIG. 19), only the Y435W mutant maintains significant activity against both pNPP and p38α MAPK phosphopeptide (FIG. 3B). In addition, binding and inhibition experiments demonstrate that 1 is only capable of binding to and inhibiting the activity of the Y435W mutant (FIG. 3C). These data identify Tyr435 as important for MKP5 phosphatase activity and compound 1 binding.

Comparative Modeling Suggests Complex Mechanism of Inhibition by 1

Figure 4A:
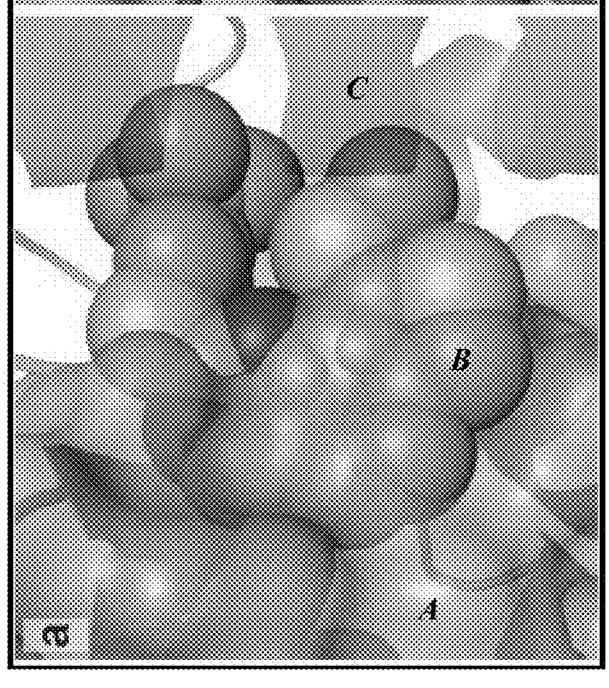
FIGS. 4A-4B show predicted clashes caused by 1 binding.
Figure 20A:
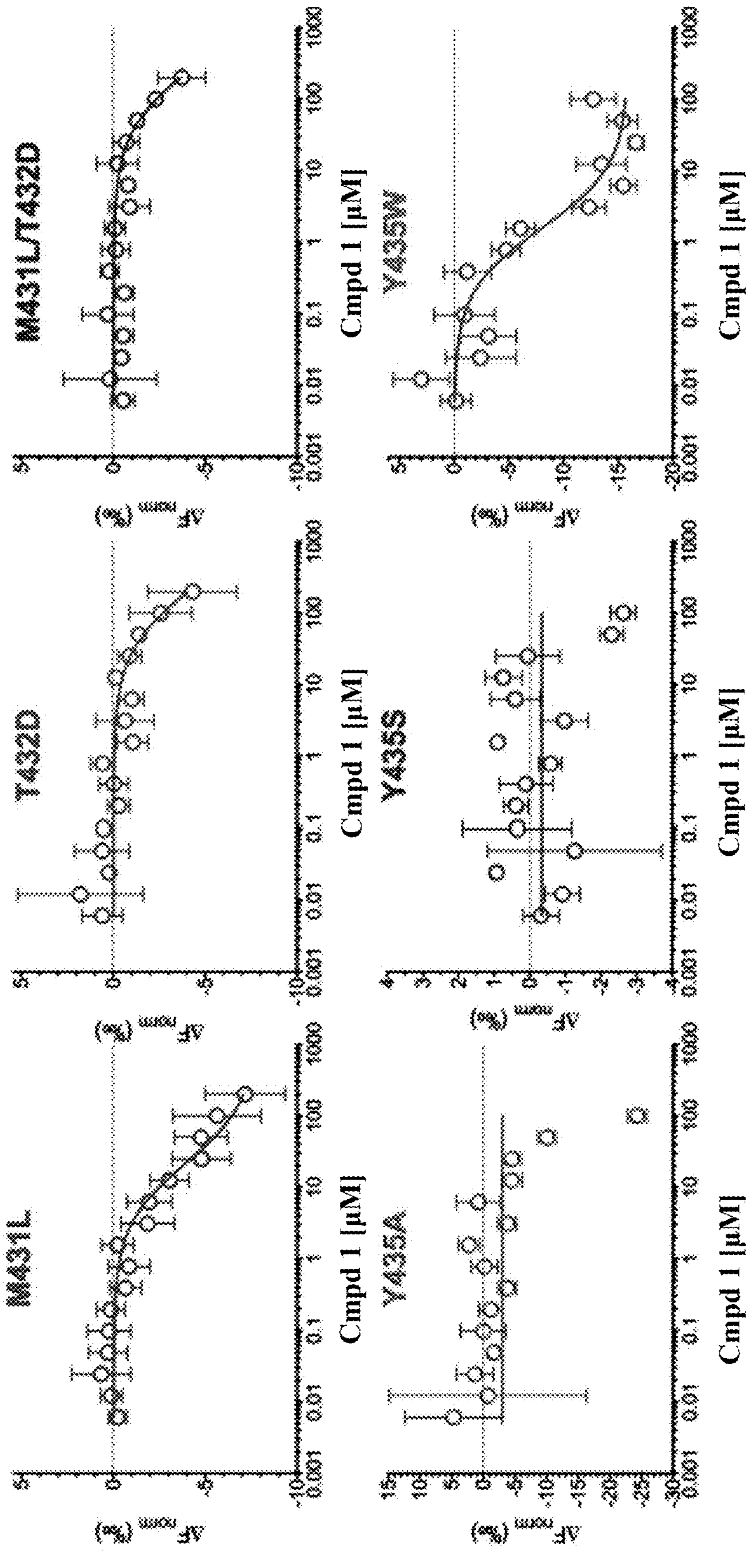
FIGS. 20A-20B show that mutations to M431, T432, and Y435 have drastic effects on inhibitor binding and enzyme inhibition.
Figure 20B:
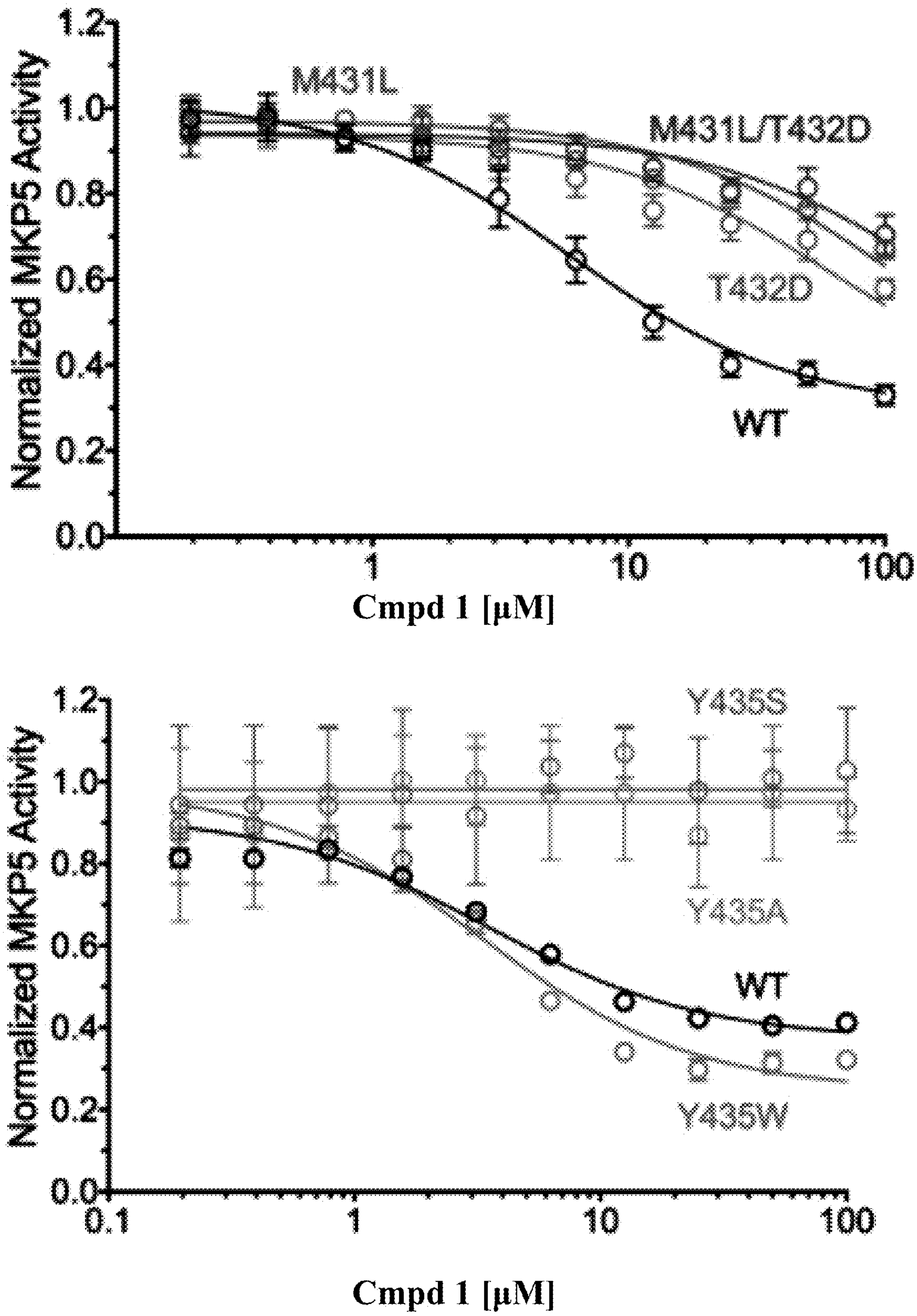
Figure 21:
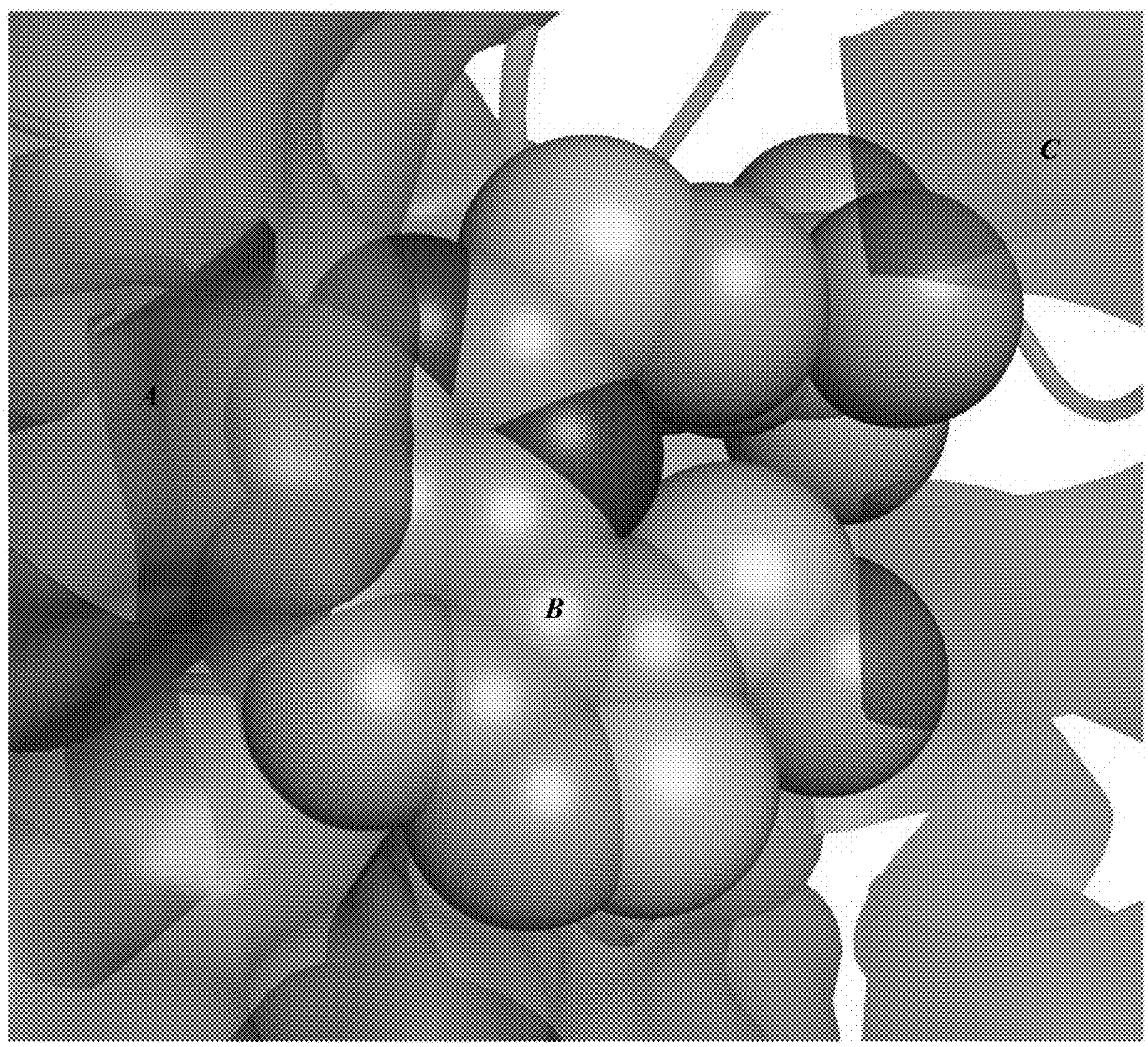
FIG. 21 shows a predicted clash with p38a MAPK. p38α MAPK (A, surface and ribbon) clashes with 1 (B, space-filling) bound to MKP5-CD (C, ribbon).
Figure 22:
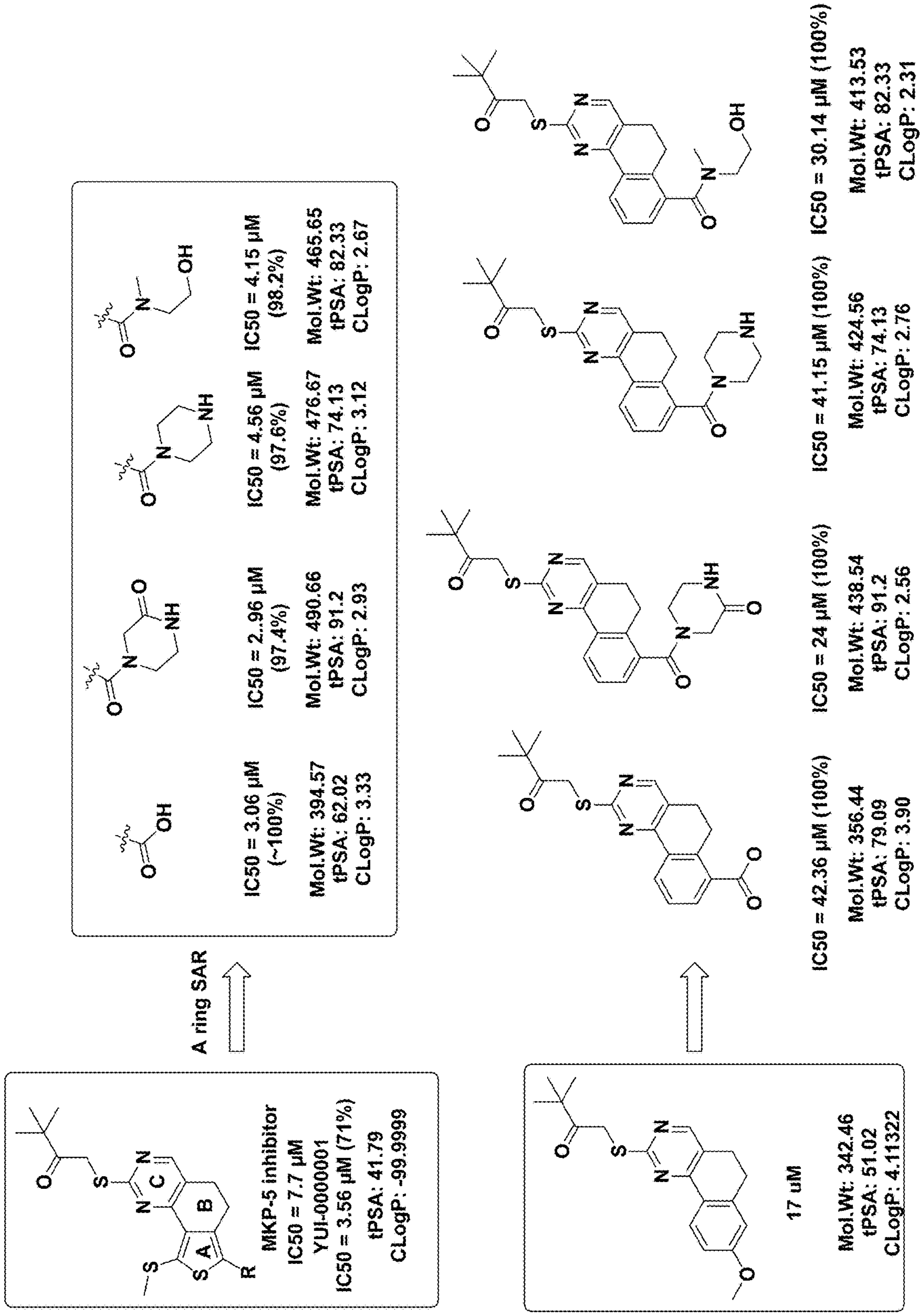
FIGS. 22-23 depict certain compounds of the invention.
Figure 23:
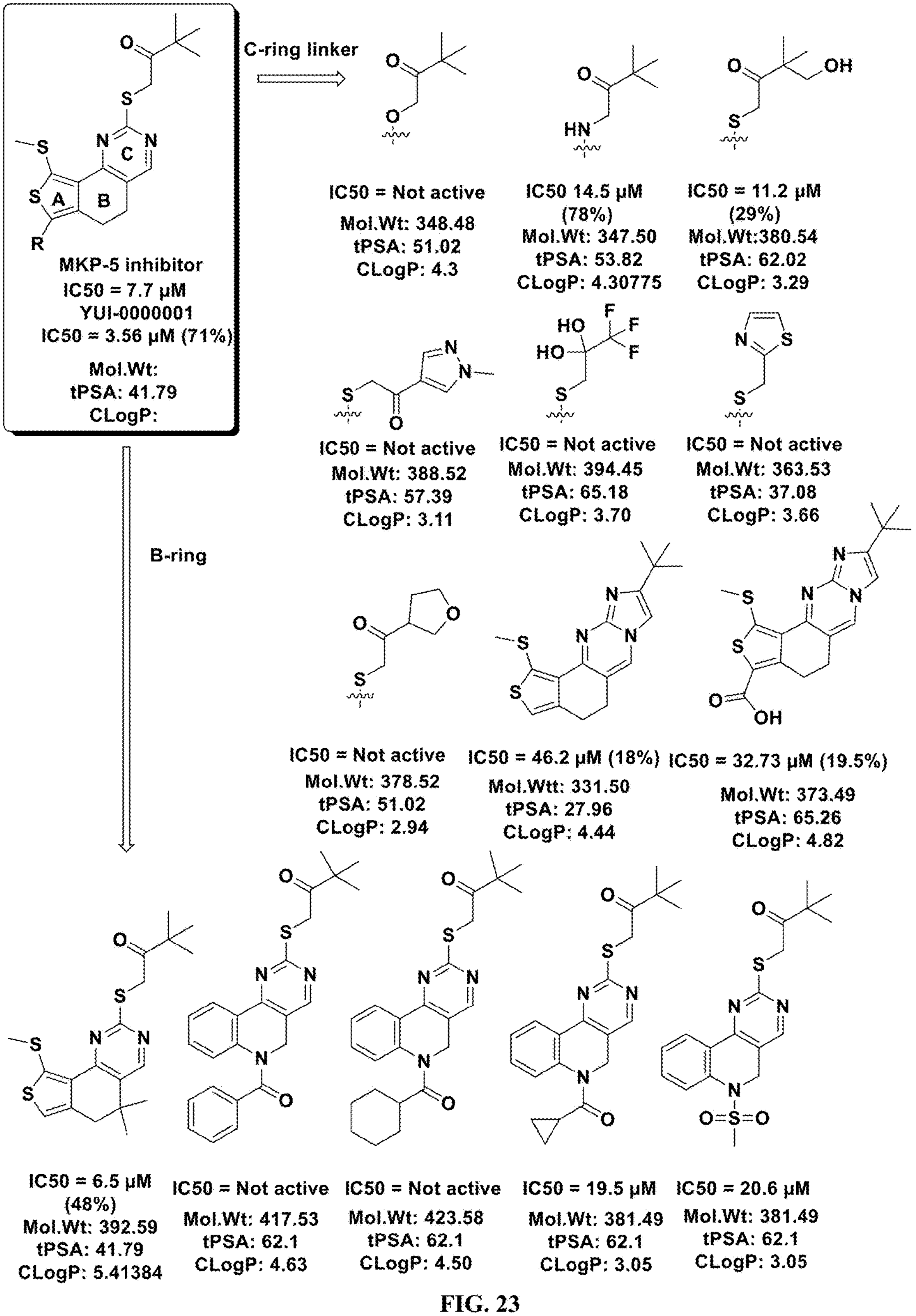

To explain the mixed mechanism of inhibition displayed by 1, this structure was compared to previously published structures of DUSP catalytic domains bound with substrate. Of particular interest was the complex between MKP7-CD and JNK134. While most DUSP-kinase complexes are mediated by the KIM in a separate kinase-binding domain, this complex was found to be entirely formed by interactions with the MKP7 catalytic domain. Further, it was proposed that this mechanism of interaction was common among MKPs that specifically inactivate the stress-activated MAPKs, like MKP5. To investigate whether 1 could affect the formation of this complex, models of MKP5-CD were generated in complex with JNK1 and p38α MAPK (FIG. 4A and FIGS. 20A-20B, respectively). Using PyMOL, this structure and previously solved structure of p38α MAPK35 were superimposed on the structure of the JNK1-MKP7-CD complex. In this model, the C-lobes of both kinases overlap significantly with the position of 1 in the allosteric pocket. Specifically, the JNK1 residues 229DHI231 (residues 227-229 in p38α MAPK) are predicted to clash with 1.

Figure 4B:
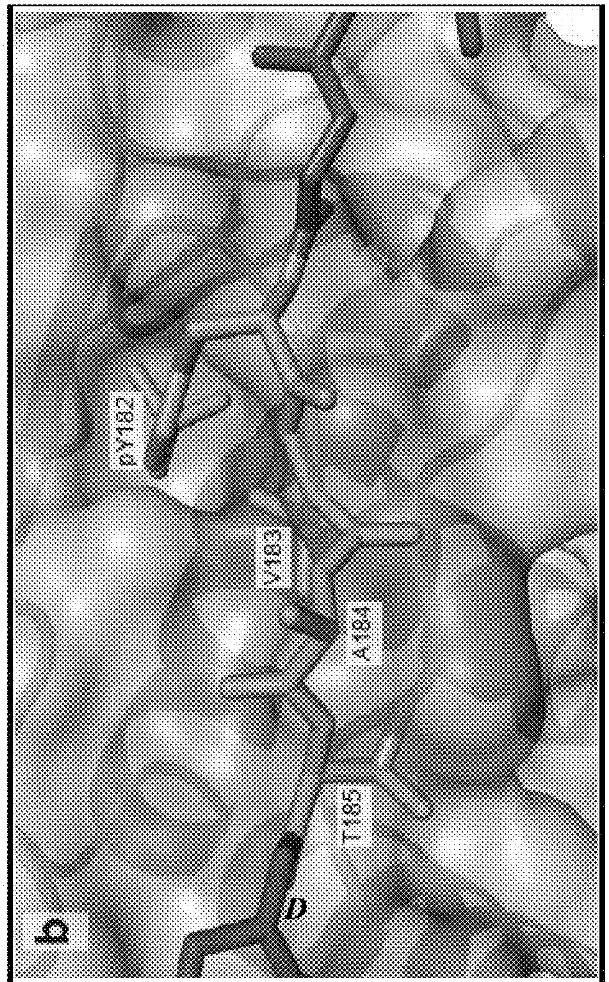

While the above model provided information about potential clashes, the lack of density for the JNK1 activation loop means that it did not address whether conformational changes seen in inhibitor-bound MKP5-CD would affect binding of the MAPK activation loop. To answer this question, a model based on the structure of the DUSP human vaccinia H1-related phosphatase (VHR) bound to a phosphopeptide similar to the p38α MAPK phosphopeptide used in the activity assays (FIG. 4B) was generated. Despite low sequence similarity, both MKP5 and VHR adopt the common PTP fold and it is assumed that they interact with the p38α MAPK activation loop in a similar manner. The model suggests that the α4-α5 and β5-α3 loops, which both shift upon 1 binding, will clash with the substrate activation loop. Residues in the phosphopeptide corresponding to 182YVAT185 (SEQ ID NO: 18) in p38α MAPK are predicted to clash with the reorganized MKP5 loops. The effect of active site collapse described above is seen in this model, as the incoming phosphotyrosine of p38α MAPK collides with residues in the catalytic pocket. This model supports the obtained experimental results that 1 exhibits a mixed mode of catalytic inhibition.

Effect of 1 on p38 MAPK, JNK and ERK1/2 Activation

Figure 5A:
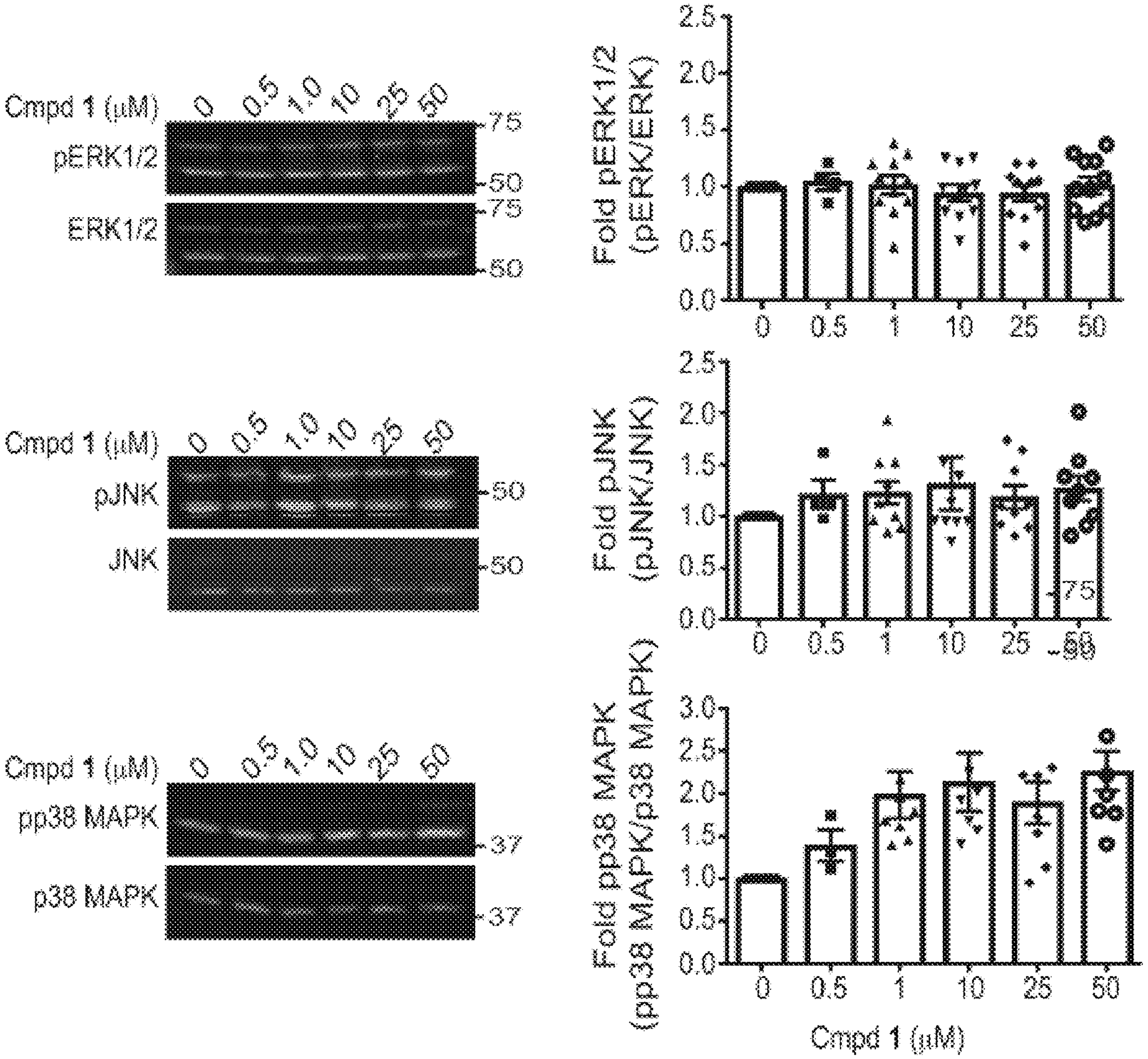
FIGS. 5A-5C show the effect of 1 on MAPK activity and TGF-β1-mediated signaling.

After demonstrating the efficacy of 1 in vitro, it was next sought to determine whether 1 exhibited cell-based activity towards MKP5. MKP5 primarily dephosphorylates p38α MAPK and JNK but demonstrates little to no activity against extracellular signal-regulated kinases 1 and 2 (ERK1/2). Consistent with this, myoblasts isolated from MKP5-deficient mice exhibit approximately 2-3-fold increases in p38α MAPK and JNK phosphorylation, but no change in ERK1/2 activation. It was first sought to measure the activation of these MAPKs upon treatment with 1 in cellular studies. C2C12 mouse myoblasts were treated with 1 and it was found that the activation of p38α MAPK was increased in a dose-dependent manner (FIG. 5A). JNK activation was also increased upon treatment of C2C12 myoblasts but with less effectiveness as compared with p38 MAPK. In contrast, 1 did not alter the activation status of ERK1/2 even at the highest concentration where p38α MAPK and JNK activities were induced by 2.0 and 1.4-fold, respectively (FIG. 5A). These results suggest that 1 selectively enhances p38α MAPK and JNK activities in a cellular context. Importantly, a lack of ERK1/2 activation with 1 implies that the compound does not exert broad non-specific inhibition amongst the MKPs. These data demonstrate that treatment of C2C12 myoblasts with 1 phenocopies myoblasts derived from MKP5-deficient mice, indicating that 1 targets MKP5 selectively in a cellular context.

Figure 5B:
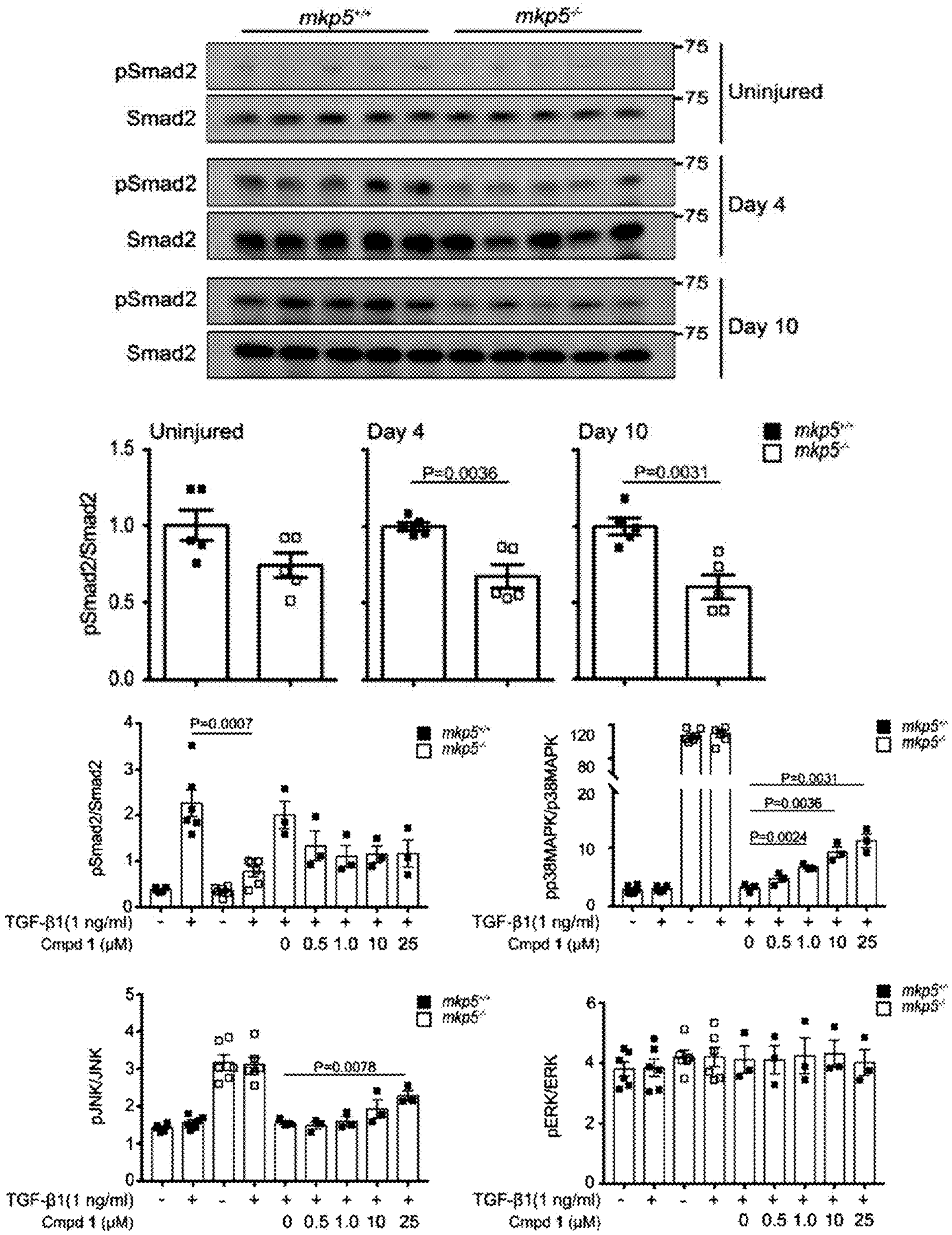
Figure 5C:
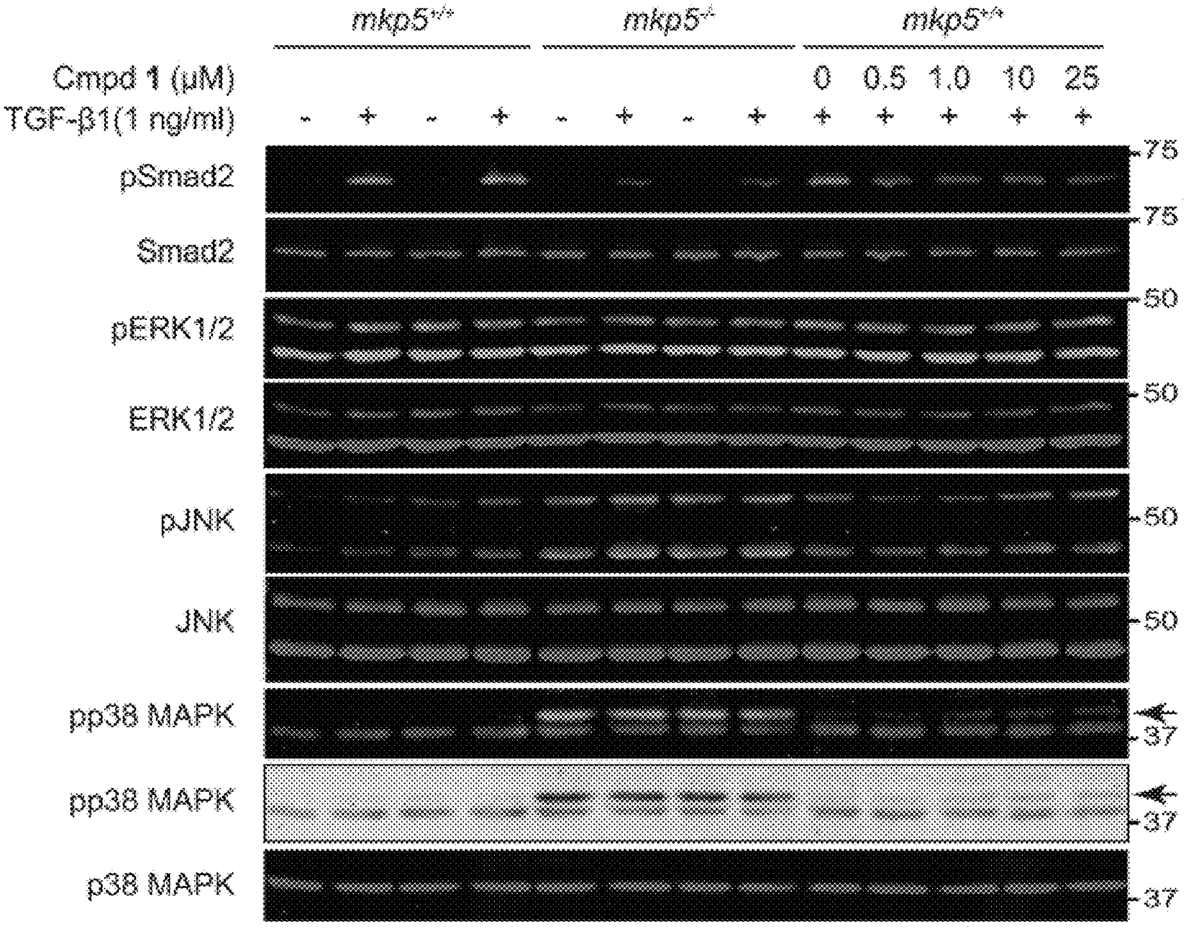

Requirement of MKP5 for TGF-β1 Signaling in Muscle and Effect of 1 on Smad2 Activity In light of previous observations that MKP5 may serve as a target for the treatment of dystrophic muscle disease, it was sought to identify a mechanism through which MKP5 inhibition might ameliorate the disease. Mice lacking MKP5 expression in the mdx mouse are protected from the development of skeletal muscle fibrosis. It is hypothesized that MKP5 might be involved in the progression of fibrosis, which is driven by the TGF-β1 signaling pathway. Disruption of TGF-β1 activity in mdx mice curtails fibrosis and subsequently improves the dystrophic phenotype. In response to injury the expression levels of TGF-β1 increases resulting in activation of the transcription factor Smad2 by phosphorylation leading to nuclear translocation and induction of fibrogenic genes. The effects on Smad2 phosphorylation in mice lacking expression of MKP5 ($mkp5^{-/-}$) in response to injury using cardiotoxin injection into skeletal muscles were determined. Smad2 phosphorylation was significantly reduced in $mkp5^{-/-}$ mice at 4 and 10 days following cardiotoxin-induced muscle injury as compared with wild type mice (FIG. 5B). When mouse embryo fibroblasts (MEFs) isolated from skeletal muscle of $mkp5^{-/-}$ mice were treated with TGF-β1, Smad2 phosphorylation was significantly inhibited as compared with wild type TGF-β1-treated MEFs (FIG. 5C). When MEFs derived from wild type mice were treated with 1, it inhibited TGF-β1-mediated Smad2 phosphorylation (FIG. 5D). Concomitantly, 1 treatment resulted in a dose-dependent increase in the phosphorylation of both p38α MAPK and JNK, but not ERK1/2 in wild type MEFs (FIG. 5C). Collectively, these data demonstrate that MKP5 inhibition by 1 attenuates TGF-β1-signaling and this interpretation is supported by similar observations obtained in MKP5-deficient MEFs.

Selected Comments

The role that MKP5 plays in the progression of dystrophic muscle disease prompted the conduction of a high-throughput screen to identify potential inhibitors of the phosphatase. Recognizing that PTPs and DUSPs present a significant challenge as drug targets, largely due to the high degree of conservation and positive charges in their catalytic site, the possibility of identifying non-catalytic site-directed inhibitors was increased by using a dually-phosphorylated peptide representing the primary substrate of MKP5, p38α MAPK. The high-throughput screen against the catalytic domain of MKP5 identified a unique inhibitor with low micromolar potency. The structure of MKP5 in complex with a small molecule inhibitor was obtained through co-crystallography. These studies revealed a novel allosteric binding site occupied by the inhibitor, the binding of which causes a partial collapse of the catalytic pocket, which may prevent access of the substrate to the catalytic sulfhydryl. Further, modeling of the MKP5-MAPK complex indicates that the inhibitor can interfere with formation of the complex, directly and/or through induced conformational shifts. Treatment of myoblasts with the inhibitor resulted in the selective activation of both p38 MAPK and JNK, but not ERK, features that are recapitulated in MKP5-deficient myoblasts. Finally, a novel relationship between MKP5 and the TGF-β1 pathway was uncovered, which has been implicated in the development of fibrosis in dystrophic muscle disease. It was demonstrated that MKP5 is required for TGF-β1 signaling, which is blocked by the inhibitor. These results reveal an unanticipated approach to targeting MKP5 by small molecules and indicate a potential mechanism of action through which MKP5 antagonism can serve as a therapeutic strategy for the treatment of dystrophic muscle disease.

Figure 6:
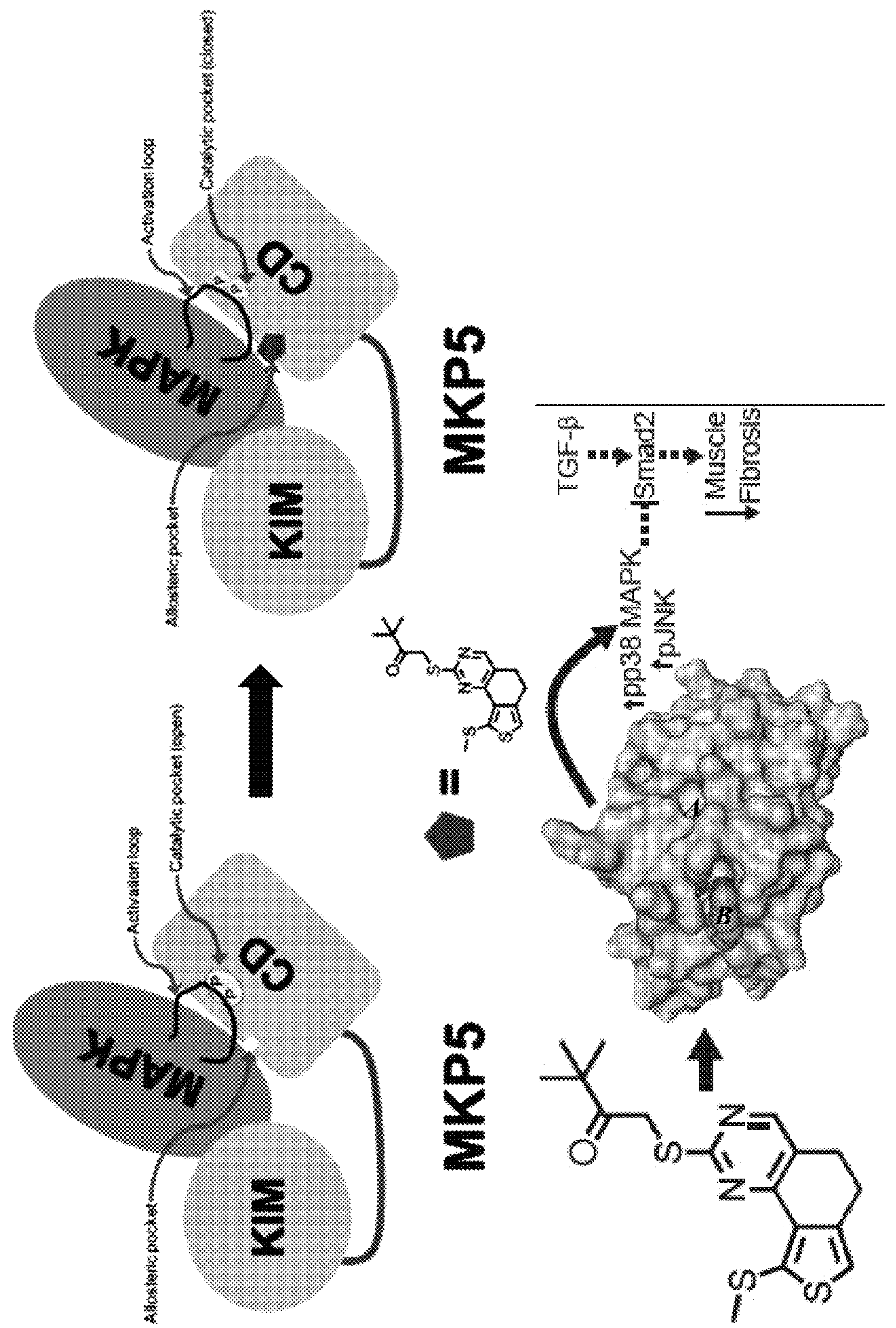
FIG. 6 shows a model for MKP5 inhibition by 1. MKP5-CD in complex with substrate MAPK. The MKP5 catalytic site binds the phosphorylated MAPK activation loop (phosphate; A) while the allosteric pocket interacts with the αG helix in the MAPK. 1 (B) binds at the allosteric site, disrupting both the activation loop and MAPK binding in addition to causing a partial collapse of the active site.
Figure 7:
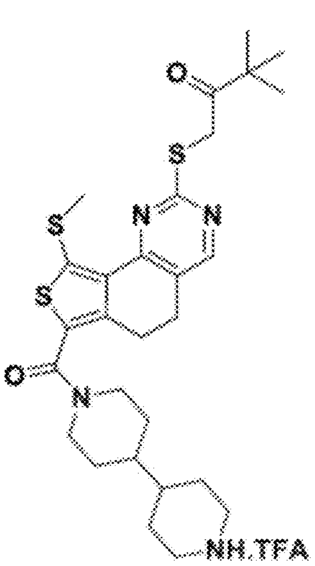
FIGS. 7-13 depict certain compounds of the invention.
Figure 7:
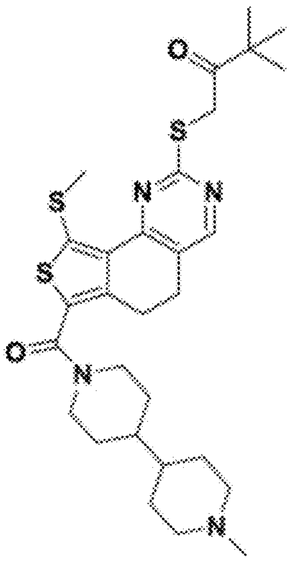
Figure 7:
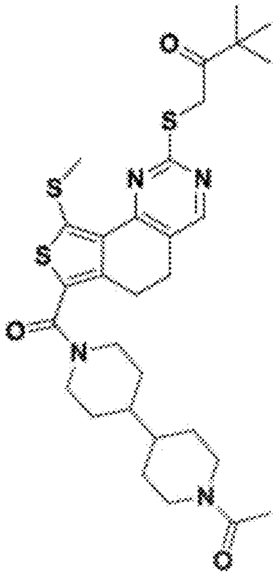
Figure 7:
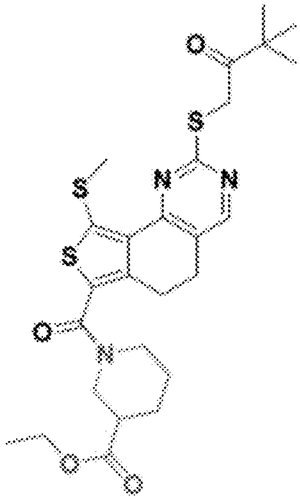
Figure 7:
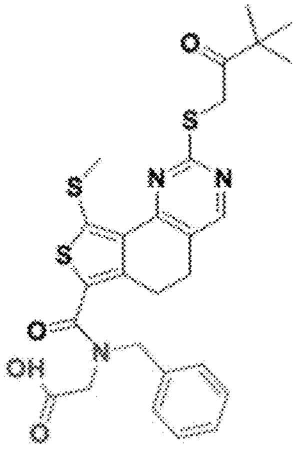
Figure 8:
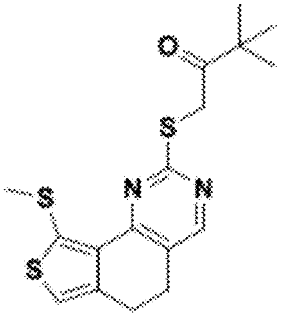
Figure 8:
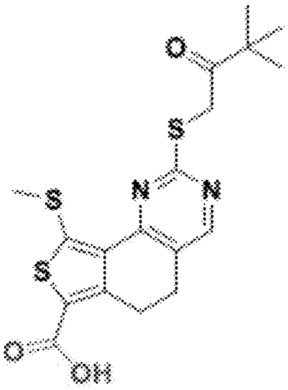
Figure 8:
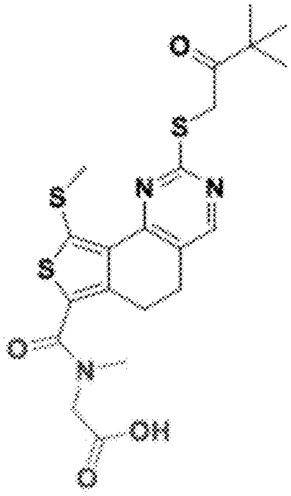
Figure 8:
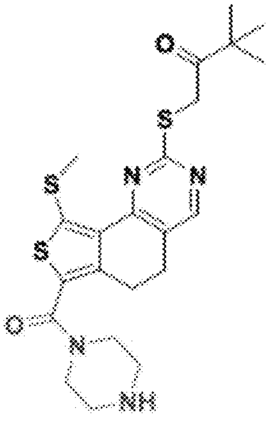
Figure 8:
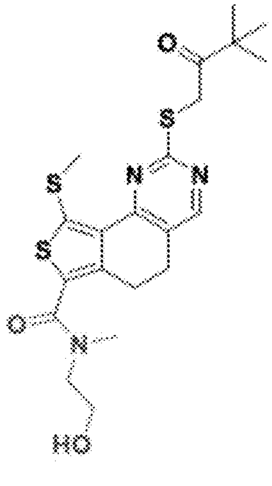
Figure 8:
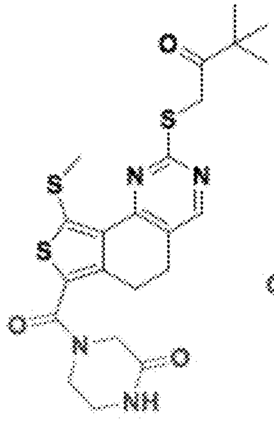
Figure 8:
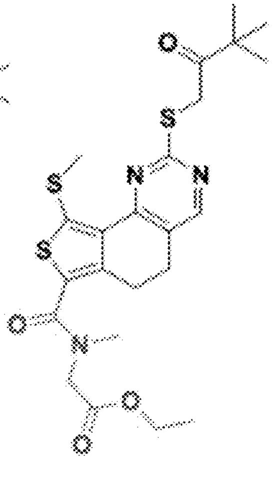
Figure 9:
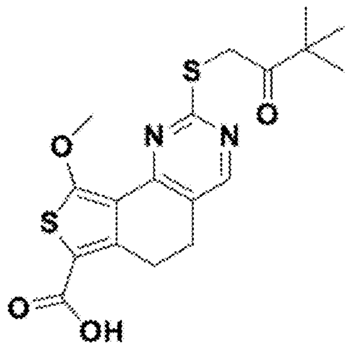
Figure 9:
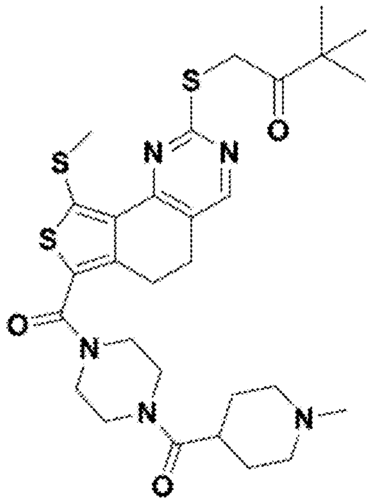
Figure 9:
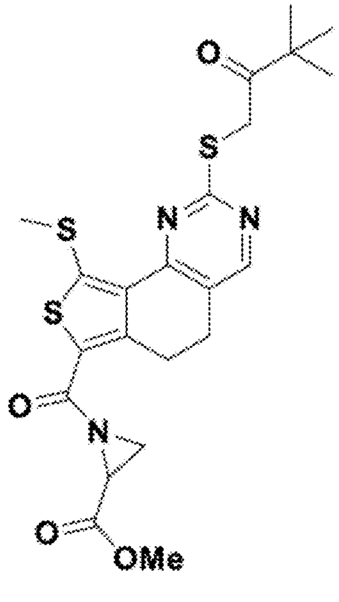
Figure 9:
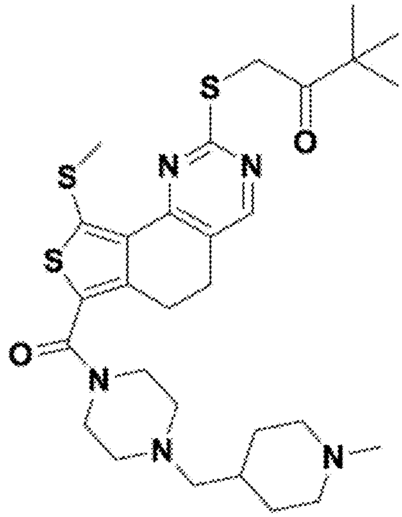
Figure 10:
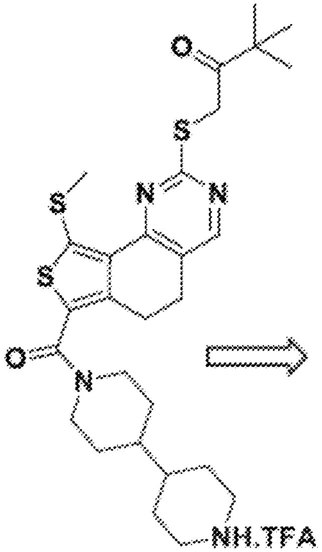
Figure 10:
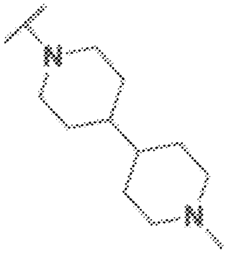
Figure 10:
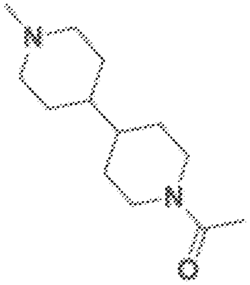
Figure 10:
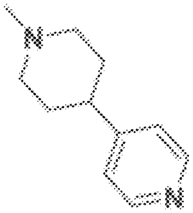
Figure 10:
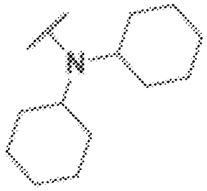
Figure 10:
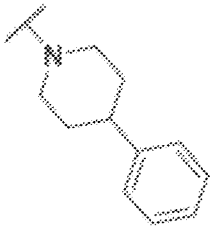
Figure 10:
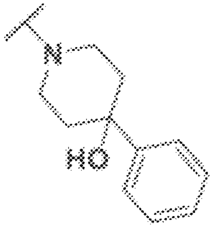
Figure 10:
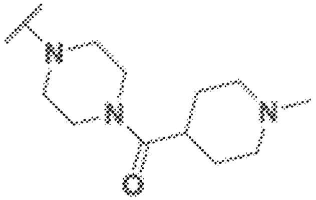
Figure 10:
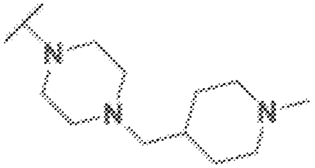
Figure 11:
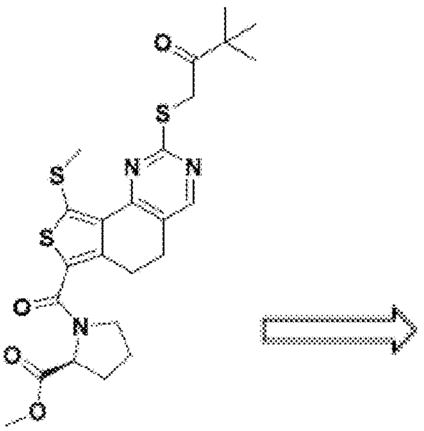
Figure 11:
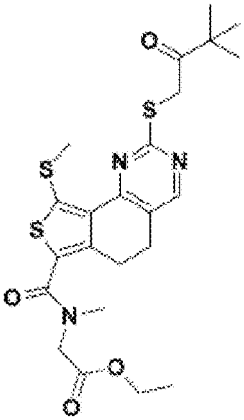
Figure 11:
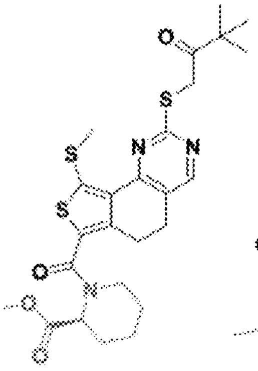
Figure 11:
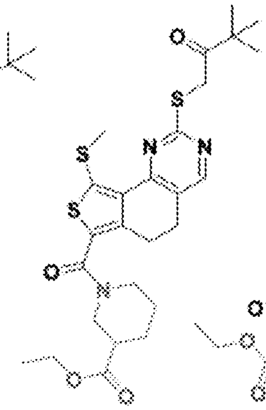
Figure 11:
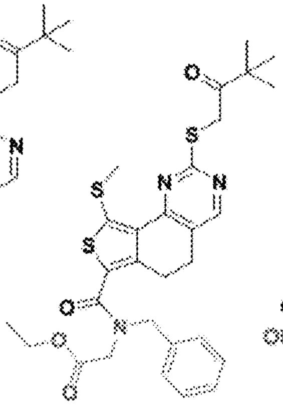
Figure 11:
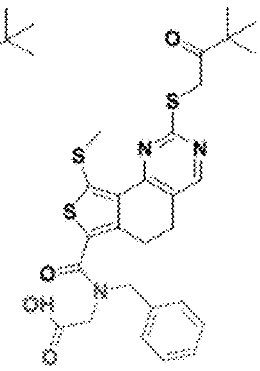
Figure 11:
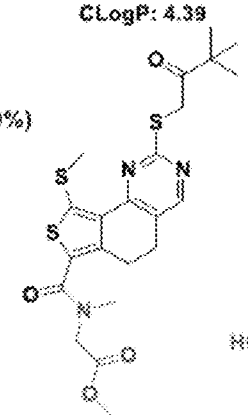
Figure 11:
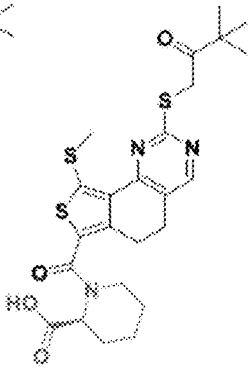
Figure 11:
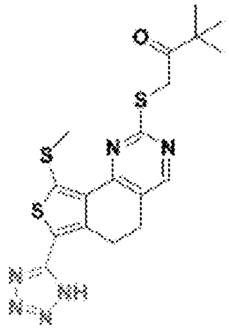
Figure 11:
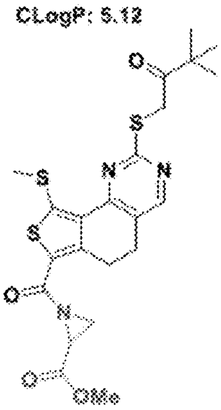
Figure 12:
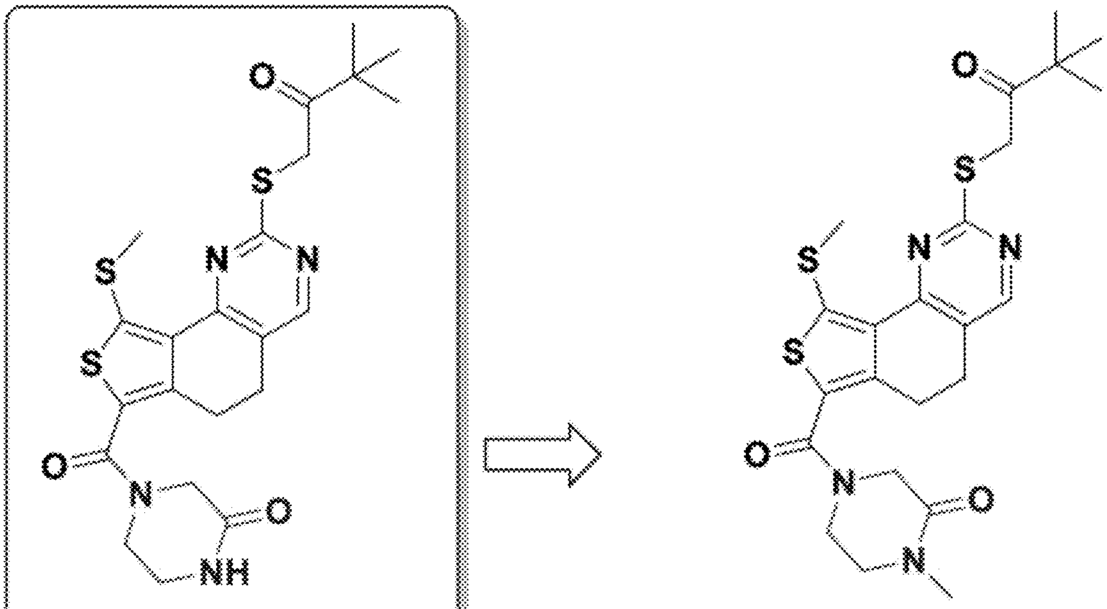
Figure 13:
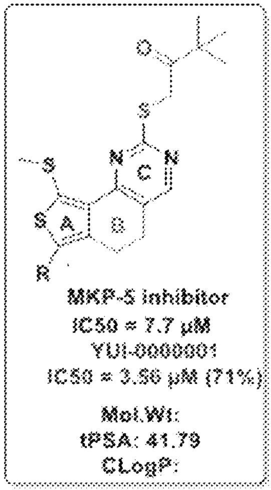
Figure 13:
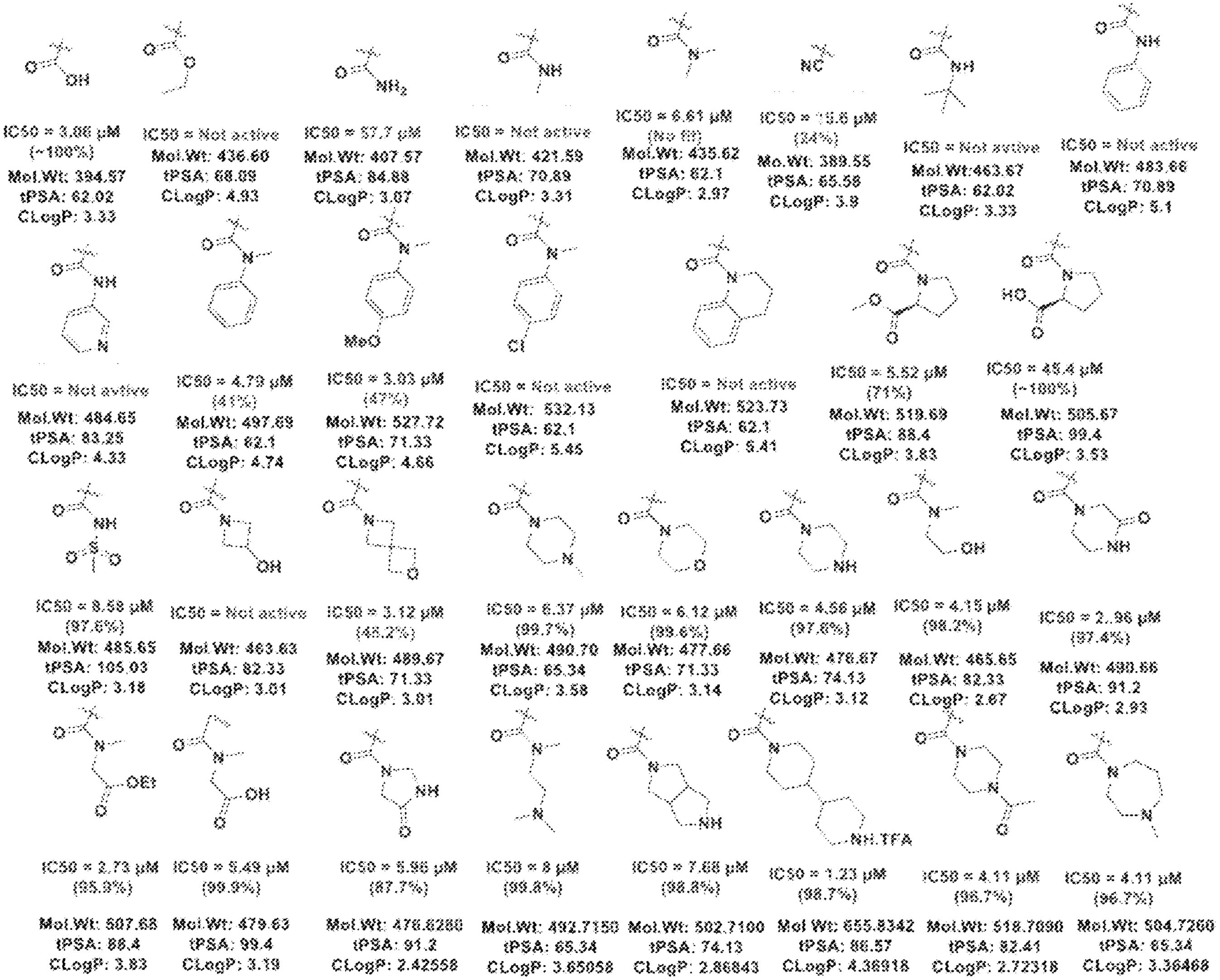

A series of experiments were undertaken to determine the mechanism by which 1 inhibits MKP5. A kinetic characterization of MKP5 activity in the presence of 1 indicated a mixed mode of inhibition, whereby both substrate affinity and maximal reaction velocity were decreased. These data support the structural data, which indicates a three-pronged mechanism of inhibition (FIG. 6). Inhibitor binding causes conformational shifts that lead to partial collapse of the active site. Further, the modeling indicates that 1 will both directly and indirectly limit the formation of the MKP-MAPK complex. It is proposed that formation of the enzyme-substrate-inhibitor complex is hindered, and that conformational shifts and steric interference prevent the phosphotyrosine and phosphothreonine of substrate MAPK from adopting an optimal position in relation to the catalytic residues of MKP5.

The allosteric pocket bound by 1 has not been previously observed, although some residues in the alpha helices α4 and β5 as well as the α4-α5 loop that comprise the allosteric site are involved with JNK binding. The residues Met431, Thr432, and Met452, all of which form hydrophobic interactions with 1 and display slight shifts upon inhibitor binding, were proposed to interact with JNK. The JNK residues Asp229 and, to a lesser extent, Ile231 were shown to be important for formation of the MKP5-JNK complex.

These molecular models predict that those residues would clash directly with 1 bound in the allosteric pocket. In addition, the mutational analysis validated that Tyr435 is critical for both inhibitor binding and catalytic activity. This work serves to support the position that the allosteric pocket plays an important role in MAPK interaction and MKP activity.

Development of PTP inhibitors has long been curtailed by poor selectivity. However, it was shown that 1 inhibits MKP1 with nearly 16-fold lower potency than MKP5. These results indicate that the allosteric pocket of MKP5 contains determinants of specificity and thus selectivity amongst the MKPs can be exploited by targeting this region. In this regard, the cell-based assays demonstrated that 1 preferentially activated p38 MAPK/JNK over that of ERK1/2. These features support the position that 1 selectively targets MKP5 rather than pervasively inhibiting other MKPs and PTPs. Finally, a link between MKP5 and the TGF-β1 pathway was uncovered. The results supported genetically in MKP5-deficient mice and fibroblasts show that MKP5 is required for TGF-β1-induced Smad2 phosphorylation. Inhibition of Smad2 phosphorylation was also observed upon treatment of fibroblasts with 1. These data indicate that a MKP5-regulated MAPK-dependent pathway plays a critical role in the activation of Smad2. This finding is significant in light of the fact that the TGF-β1 pathway is a validated target for anti-fibrotic therapy. Since fibrosis is the end-stage sequelae in dystrophic muscle disease that results in the loss of muscle function, these data provide insight into how MKP5 antagonism offers therapeutic relief to this and other these devastating diseases.

In summary, this work has uncovered a novel allosteric site in MKP5, which represents a new mechanism that can be exploited to specifically inhibit this enzyme and possibly other MKPs. By targeting the MKP5 allosteric site, it is now possible to circumvent the issues that have plagued the development of DUSP inhibitors, paving the way for the development of a drug for the treatment of DMD and potentially other diseases in which tissue fibrosis represents the end-stage sequalae of organ failure. Allosteric modulation of the MKPs is now feasible and will facilitate targeting these enzymes against a variety of human diseases.

Enumerated Embodiments

The following enumerated embodiments are provided, the numbering of which is not to be construed as designating levels of importance.

Embodiment 1 provides a compound of formula (1), or a salt, solvate, enantiomer, diastereomer, or tautomer thereof:

(1)

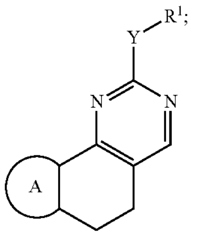

wherein: Y is selected from the group consisting of S and NH; A ring is selected from the group consisting of

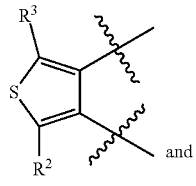 and 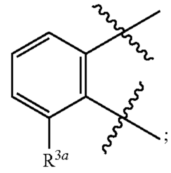;

$R^1$ is —C(R'(R")—C(=O)—R", wherein: R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl; $R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl; $R^2$ is selected from the group consisting of —CN, 1H-tetrazol-5-yl ( 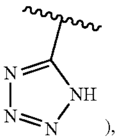 ), C(=O)NH—S(=O)$_2$($C_1$-$C_6$ alkyl or $C_3$-$C_8$ cycloalkyl), and —C(=O)NR$^{2a}$R$^{2b}$, wherein $R^{2a}$ and $R^{2b}$ are independently selected from the group consisting of optionally substituted $C_1$-$C_6$ alkyl, optionally substituted $C_3$-$C_8$ cycloalkyl, optionally substituted phenyl, optionally substituted heteroaryl, —S(=O)$_2$($C_1$-$C_6$ alkyl), and —S(=O)$_2$($C_3$-$C_8$ cycloalkyl), or $R^{2a}$ and $R^{2b}$ combine with the N atom to which they are bound to form optionally substituted 3- to 8-membered heterocyclyl or heteroaryl; $R^3$ is selected from the group consisting of H, $C_1$-$C_6$ alkyl, and $C_1$-$C_6$ thioether; $R^3$ is selected from the group consisting of —COOH, —CN, and —C(=O)NR$^{3b}$R$^{3c}$, wherein $R^{3b}$ and $R^{3c}$ are independently selected from the group consisting of H, optionally substituted $C_1$-$C_6$ alkyl, optionally substituted $C_3$-$C_8$ cycloalkyl, optionally substituted phenyl, and optionally substituted heteroaryl, or $R^{3b}$ and $R^{3c}$ combine with the N atom to which they are bound to form optionally substituted 3- to 8-membered heterocyclyl.

Embodiment 2 provides the compound of Embodiment 1, wherein $R^1$ is —C(R')(R")—C(=O)-(optionally substituted $C_3$-$C_8$ cycloalkyl).

Embodiment 3 provides the compound of Embodiment 1, wherein $R^1$ is —C(R')(R")—C(=O)-(optionally substituted $C_1$-$C_6$ alkyl).

Embodiment 4 provides the compound of any of Embodiments 1 and 3, wherein $R^1$ is —C(R')(R")—C(=O)-(optionally substituted tert-butyl).

Embodiment 5 provides the compound of any of Embodiments 1-4, wherein $R^{2a}$ is methyl.

Embodiment 6 provides the compound of any of Embodiments 1-5, wherein R' and R" are independently selected from the group consisting of H, Me, and Et.

Embodiment 7 provides the compound of an of Embodiments 1 and 3-6 wherein $R^1$ is selected from the group consisting of:

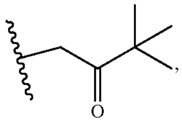
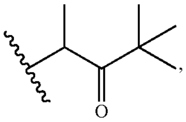
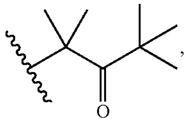
and
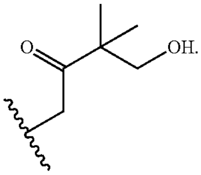
Embodiment 8 provides the compound of any of Embodiments 1 and 3-7, wherein $R^1$ is
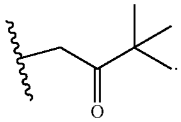 [SMILES: *CC(=O)C(C)(C)C]
Embodiment 9 provides the compound of any of Embodiments 1-8, wherein the A ring is
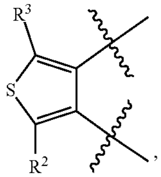
and $R^2$ is selected from the group consisting of: —CN, 1H-tetrazol-5-yl,
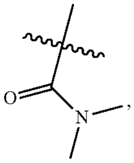
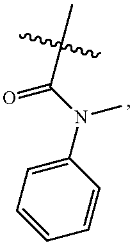
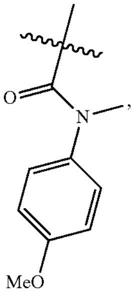
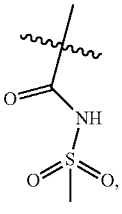
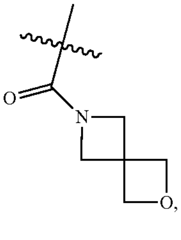
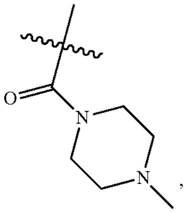
-continued
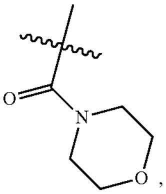
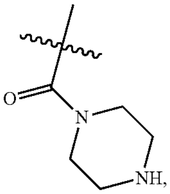
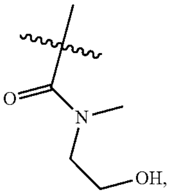
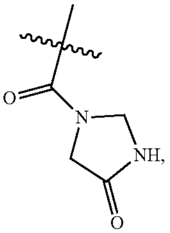
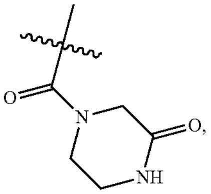
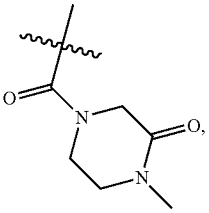
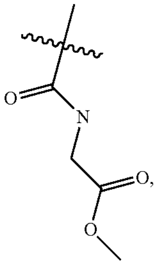
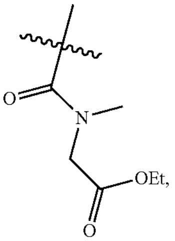
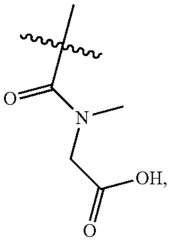
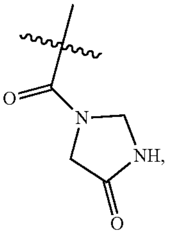
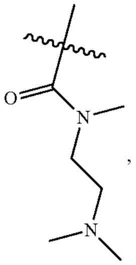
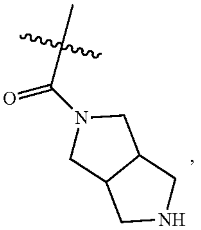
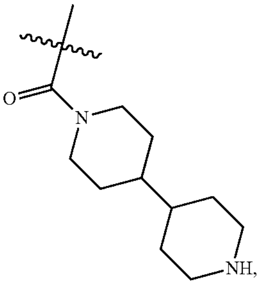
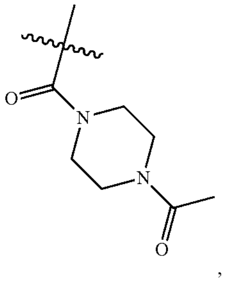

-continued
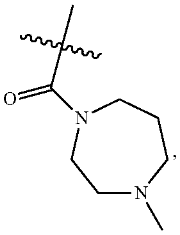,
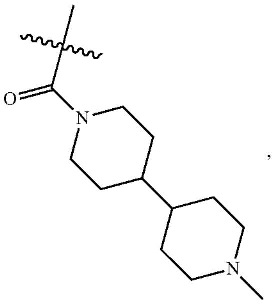,
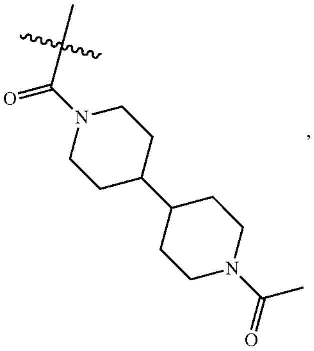,
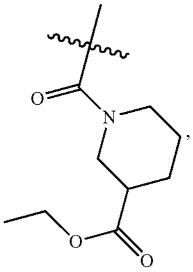,
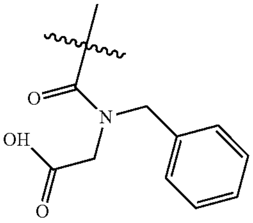,
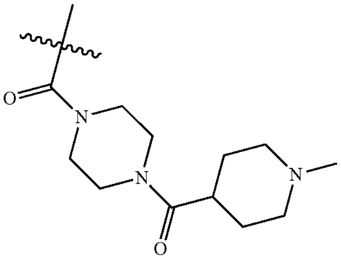,
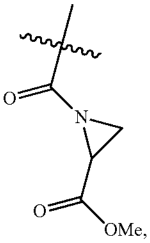,
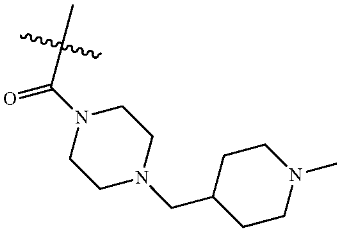,
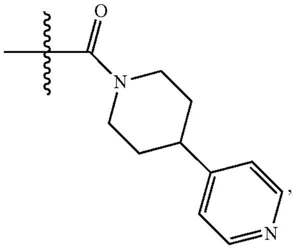,
-continued
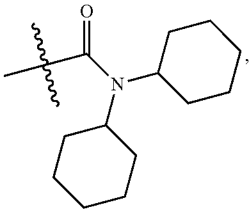,
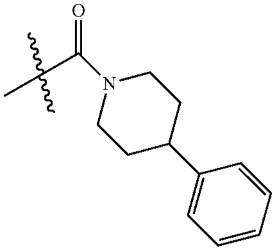,
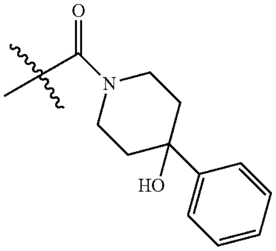,
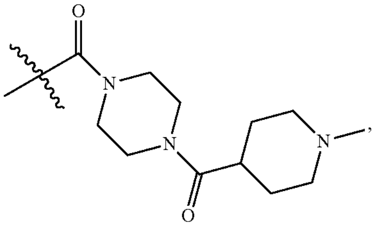,
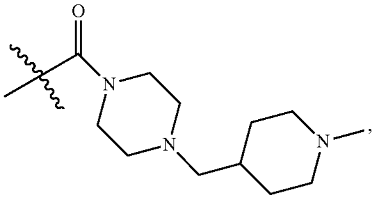,
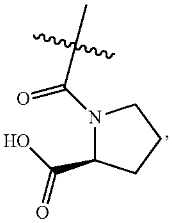,
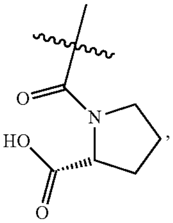,
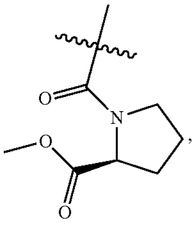,
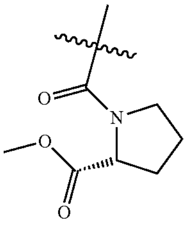, -continued

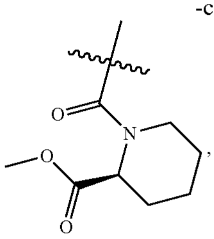

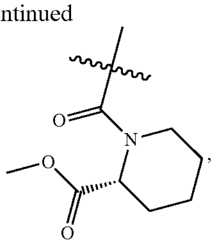

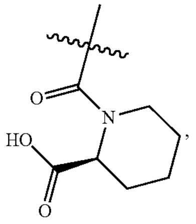

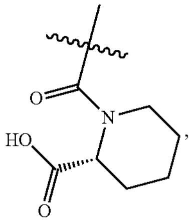

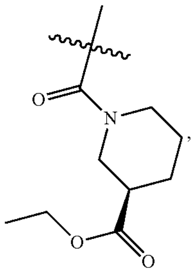

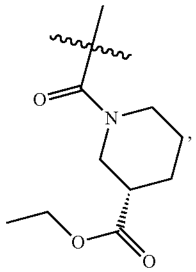

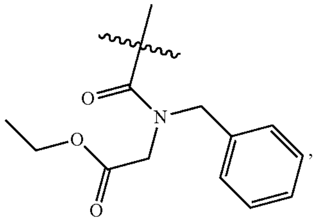

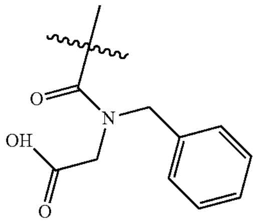

, and

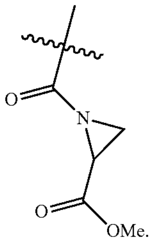

Embodiment 10 provides the compound of any of Embodiments 1-9, wherein the A ring is

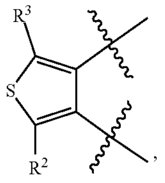

and $R^3$ is $C_1$-$C_6$ thioether.

Embodiment 11 provides the compound of any of Embodiments 1-10, wherein $R^3$ is selected from the group consisting of —SMe, —SEt, —S(nPr), —S(iPr), —S(nBu), —S(secBu), —S(iBu), and S(tBu).

Embodiment 12 provides the compound of any of Embodiments 1-8 and 11, wherein the A ring is

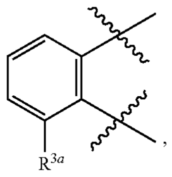

and $R^3$ is selected from the group consisting of COOH,

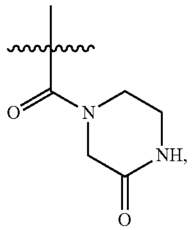

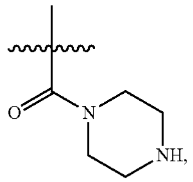

and

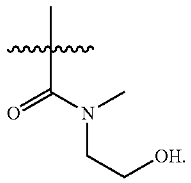

Embodiment 13 provides the compound of any of Embodiments 1-12, which is selected from the group consisting of:

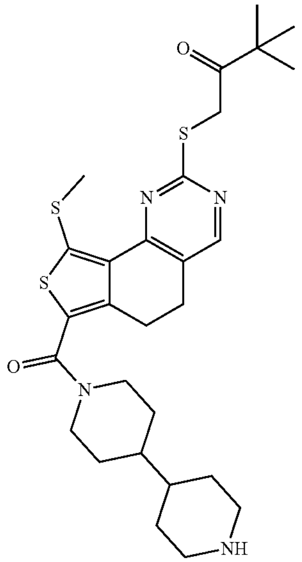

and

-continued

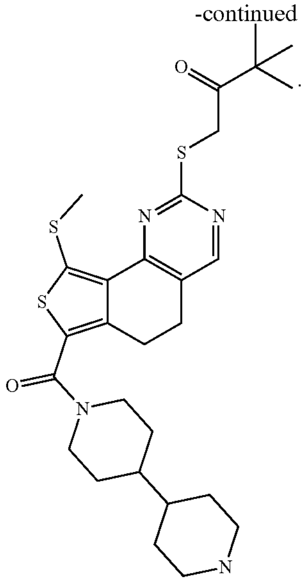

Embodiment 14 provides a pharmaceutical composition comprising the compound of any one of Embodiments 1-13 and at least one pharmaceutically acceptable carrier.

Embodiment 15 provides a method of treating or preventing a MKP5 modulated disease or disorder in a subject, the method comprising administering to the subject a therapeutically effective amount of the compound of any of Embodiments 1-13 and/or the composition of Embodiment 14.

Embodiment 16 provides the method of Embodiment 15, wherein the MKP5 modulated disease or disorder is a fibrotic disease or disorder.

Embodiment 17 provides the method of any of Embodiments 15-16, wherein the MKP5 modulated disease or disorder is selected from the group consisting of dystrophic muscle disease, a cardiac or vascular disease, idiopathic pulmonary fibrosis, or any combinations thereof.

Embodiment 18 provides the method of any of Embodiments 15-17, wherein the subject is a mammal.

Embodiment 19 provides the method of Embodiment 18, wherein the mammal is a human.

Embodiment 20 provides the method of any of Embodiments 15-19, wherein the compound is administered to the subject by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

Embodiment 21 provides the method of any of Embodiments 15-20, further comprising administering to the subject at least one additional agent that treats or prevents the MKP5 modulated disease or disorder in the mammal.

Embodiment 22 provides the method of Embodiment 21, wherein the compound and at least one additional agent are coformulated.

Embodiment 23 provides a method of determining if a test compound is a MKP5 inhibitor, the method comprising: contacting a test compound with (i) a peptide comprising the amino acid sequence pThr-Gly-pTyr and (ii) the catalytic domain of MKP5, or an active fragment thereof, thus forming a composition; measuring MKP5 activity in the composition; and comparing the MKP5 activity in the composition to a control; thereby determining if the test compound is a MKP5 inhibitor.

Embodiment 24 provides the method of Embodiment 23, wherein the peptide comprises the amino acid sequence Asp-Asp-Glu-Nle-pThr-Gly-pTyr-Val-Ala-Thr-Arg (SEQ ID NO: 15).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (1), or a salt, solvate, enantiomer, diastereomer, or tautomer thereof:

(1)

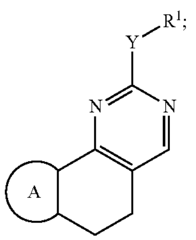

wherein:

Y is selected from the group consisting of S and NH;

A ring is

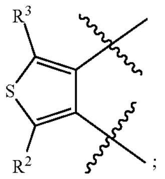

$R^1$ is —C(R')(R")—C(=O)—$R^{1a}$, wherein:

R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl;

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of 1H-tetrazol-5-yl

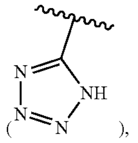

C(═O)NH—S(═O)$_2$($C_1$-$C_6$ alkyl or $C_3$-$C_8$ cycloalkyl), and —C(═O)$NR^{2a}R^{2b}$, wherein $R^{2a}$ and $R^{2b}$ are independently selected from the group consisting of optionally substituted $C_1$-$C_6$ alkyl, optionally substituted $C_3$-$C_8$ cycloalkyl, optionally substituted phenyl, optionally substituted heteroaryl, —S(═O)$_2$($C_1$-$C_6$ alkyl), and —S(═O)$_2$($C_3$-$C_8$ cycloalkyl), or $R^{2a}$ and $R^{2b}$ combine with the N atom to which they are bound to form optionally substituted 3- to 8-membered heterocyclyl or heteroaryl; and $R^3$ is $C_1$-$C_6$ thioether.

2. The compound of claim 1, wherein $R^1$ is

—C(R')(R")—C(═O)-(optionally substituted $C_3$-$C_8$ cycloalkyl) or

—C(R')(R")—C(═O)-(optionally substituted $C_1$-$C_6$ alkyl).

3. The compound of claim 1, wherein $R^1$ is

—C(R')(R")—C(═O)-(optionally substituted tert-butyl).

4. A compound of formula (1), or a salt, solvate, enantiomer, diastereomer, or tautomer thereof:

(I)

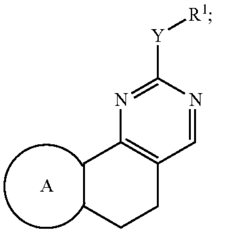

wherein:

Y is selected from the group consisting of S and NH;

A ring is

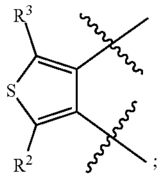

$R^1$ is —C(R')(R")—C(═O)—$R^{1a}$, wherein:

R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl:

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of 1H-tetrazol-5-yl

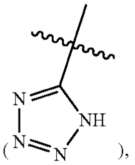

C(═O)NH—S(═O)$_2$($C_1$-$C_6$ alkyl or $C_3$-$C_8$ cycloalkyl), and —C(═O)$NR^{2a}R^{2b}$, wherein $R^{2a}$ is methyl and $R^{2b}$ is selected from the group consisting of optionally substituted $C_1$-$C_6$ alkyl, optionally substituted $C_3$-$C_8$ cycloalkyl, optionally substituted phenyl, optionally substituted heteroaryl, —S(═O)$_2$($C_1$-$C_6$ alkyl), and —S(═O)$_2$($C_3$-$C_8$ cycloalkyl) and $R^3$ is $C_1$-$C_6$ thioether.

5. The compound of claim 1, wherein R' and R" are independently selected from the group consisting of H, Me, and Et.

6. The compound of claim 1, wherein $R^1$ is selected from the group consisting of:

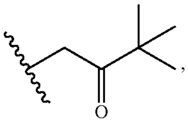

,

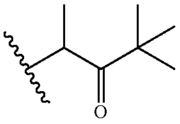

,

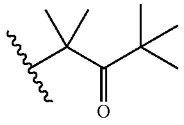

, and

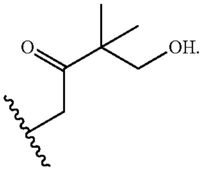

7. The compound of claim 1, wherein $R^1$ is

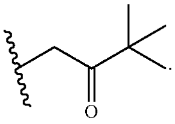 [SMILES: *CC(=O)C(C)(C)C]

8. A compound of formula (1), or a salt, solvate, enantiomer, diastereomer, or tautomer thereof:

(I)

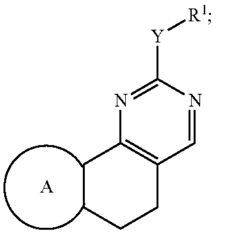

wherein:

Y is selected from the group consisting of S and NH;

A ring is

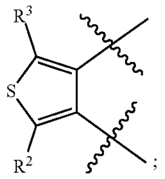

$R^1$ is —C(R')(R")—C(=O)—$R^{1a}$, wherein:

R' and R" are independently selected from the group consisting of H optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl;

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of:

1H-tetrazol-5-yl,

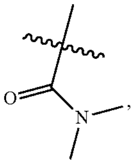
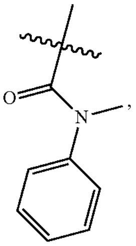
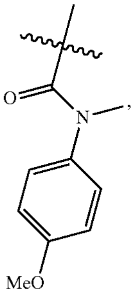
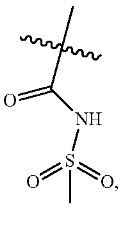
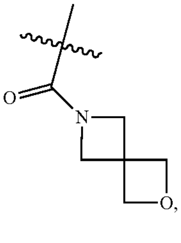
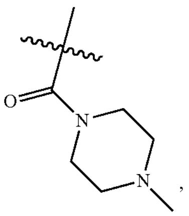

-continued

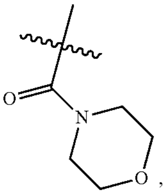
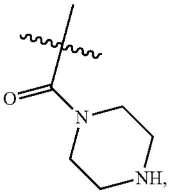
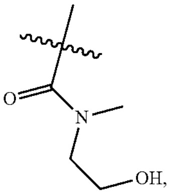
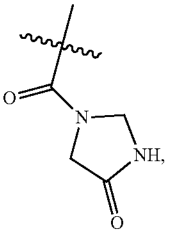
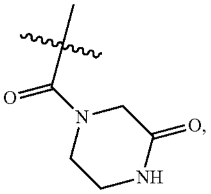
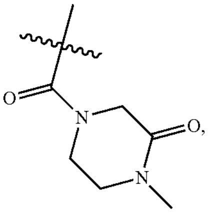
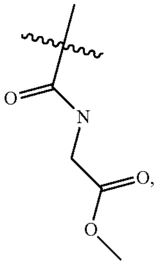
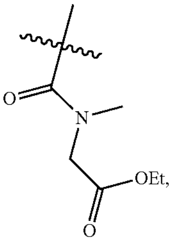
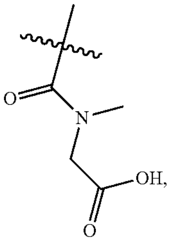
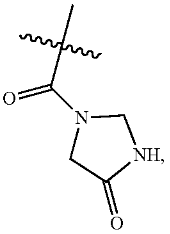
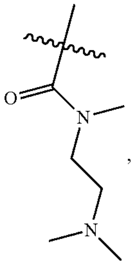
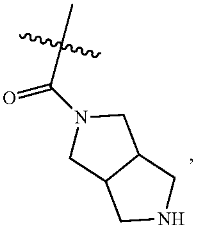
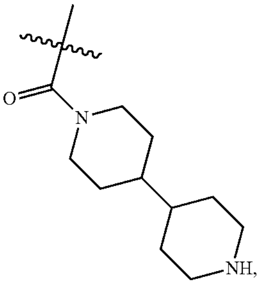
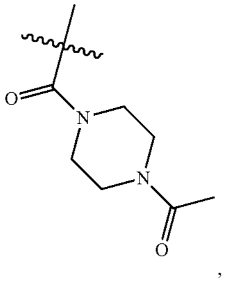

-continued
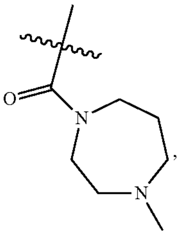,
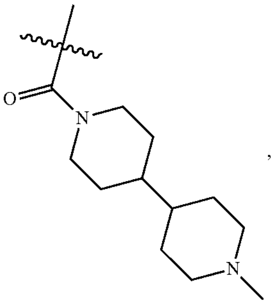,
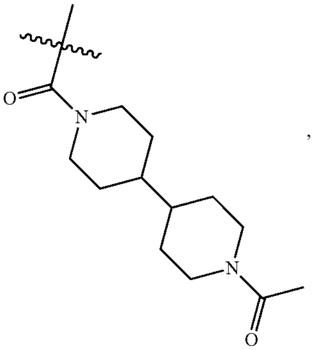,
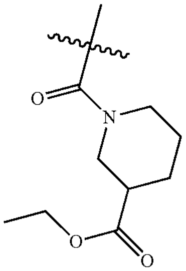,
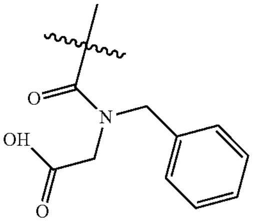,
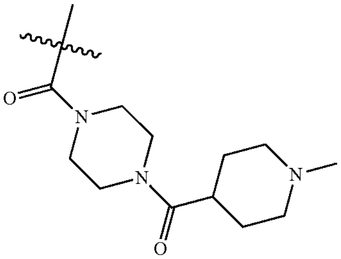,
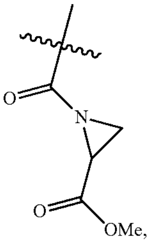,
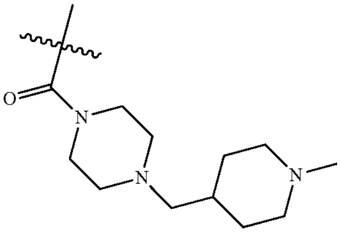,
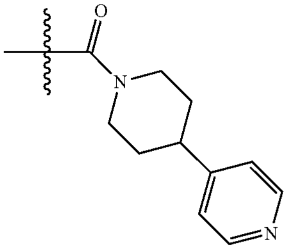,
-continued
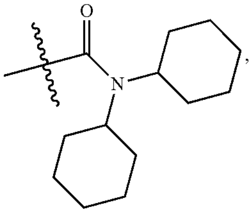,
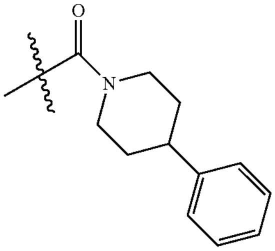,
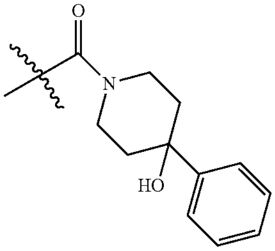,
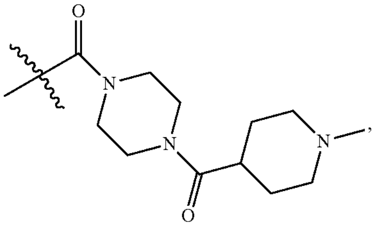,
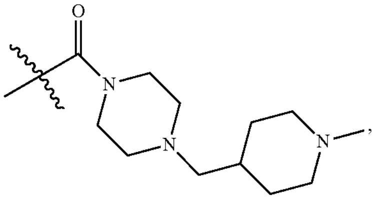,
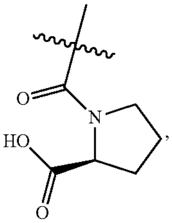,
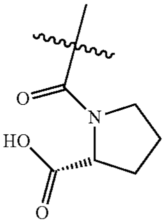,
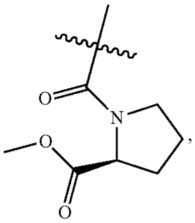,
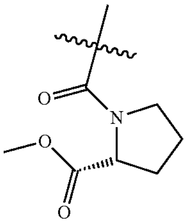, -continued

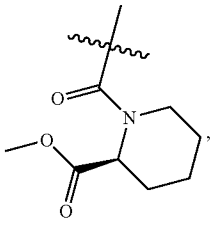
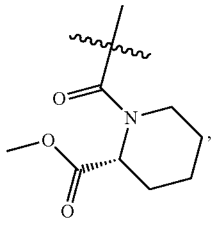
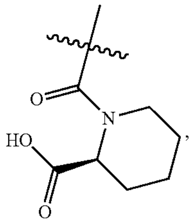
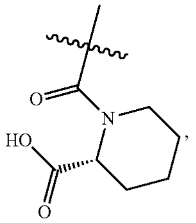
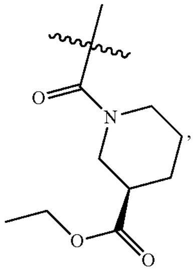
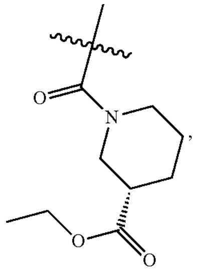
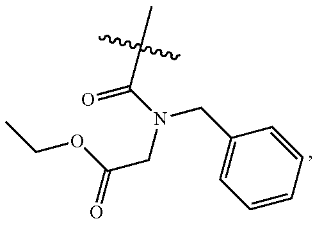
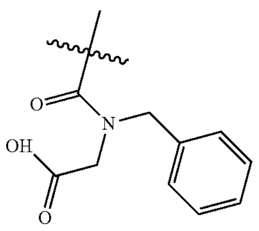
, and
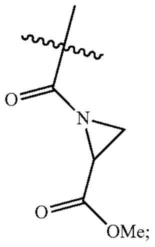

$R^3$ is $C_1$-$C_6$ thioether.

9. The compound of claim 1, wherein $R^3$ is selected from the group consisting of —SMe, —SEt, —S(nPr), —S(iPr), —S(nBu), —S(secBu), —S(iBu), and S(tBu).

10. The compound of claim 1, which is selected from the group consisting of:

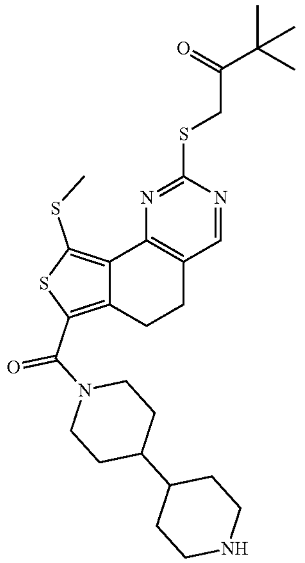
and
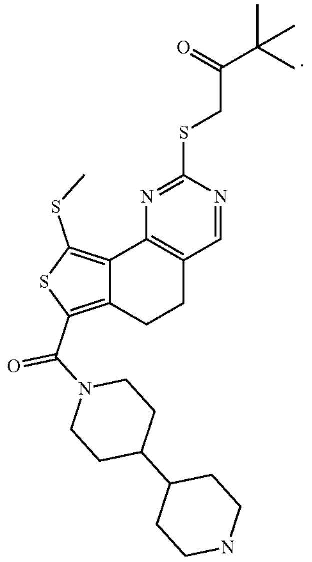

11. A pharmaceutical composition comprising the compound of claim 1 and at least one pharmaceutically acceptable carrier.

12. A method of treating or ameliorating a Mitogen-Activated Protein Kinase Phosphatase-5 (MKP5) modulated disease or disorder in a subject, the method comprising administering to the subject a therapeutically effective amount of a compound of formula (1), or a salt, solvate, enantiomer, diastereomer, or tautomer thereof:

(I)

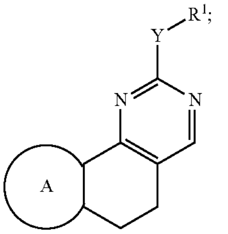

wherein:

Y is selected from the group consisting of S and NH;

A ring is (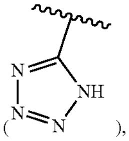), $R^1$ is —C(R')(R")—C(═O)—$R^{1a}$, wherein:

R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl;

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of 1H-tetrazol-5-yl (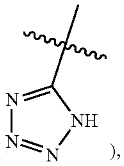),

—C(═O)NH—S(═O)$_2$($C_1$-$C_6$ alkyl or $C_3$-$C_8$ cycloalkyl), and —C(═O)N$R^{2a}R^{2b}$, wherein $R^{2a}$ and $R^{2b}$ are independently selected from the group consisting of optionally substituted $C_1$-$C_6$ alkyl, optionally substituted $C_3$-$C_8$ cycloalkyl, optionally substituted phenyl, optionally substituted heteroaryl, —S(═O)$_2$($C_1$-$C_6$ alkyl), and —S(═O)$_2$ ($C_3$-$C_8$ cycloalkyl), or $R^{2a}$ and $R^{2b}$ combine with the N atom to which they are bound to form optionally substituted 3- to 8-membered heterocyclyl or heteroaryl; and $R^3$ is $C_1$-$C_6$ thioether.

13. The method of claim 12, wherein the MKP5 modulated disease or disorder is a fibrotic disease or disorder.

14. The method of claim 13, wherein the MKP5 modulated disease or disorder is selected from the group consisting of dystrophic muscle disease, a cardiac or vascular disease, idiopathic pulmonary fibrosis, or any combinations thereof.

15. The method of claim 12, wherein the subject is a mammal.

16. The method of claim 15, wherein the mammal is a human.

17. The method of claim 12, wherein the compound is administered to the subject by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

18. The method of claim 12, further comprising administering to the subject at least one additional agent that treats or ameliorates the MKP5 modulated disease or disorder in the mammal.

19. The method of claim 18, wherein the compound and at least one additional agent are coformulated.

20. A method of treating or ameliorating a Mitogen-Activated Protein Kinase Phosphatase-5 (MKP5) modulated disease or disorder in a subject, the method comprising administering to the subject a therapeutically effective amount of a compound of formula (1), or a salt, solvate, enantiomer, diastereomer, or tautomer thereof:

(I)

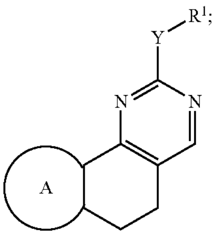

wherein:

Y is selected from the group consisting of S and NH;

A ring is

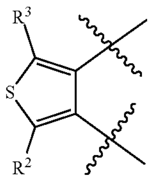;

$R^1$ is —C(R')(R")—C(═O)—$R^{1a}$, wherein:

R' and R" are independently selected from the group consisting of H, optionally substituted $C_1$-$C_6$ alkyl, and optionally substituted $C_3$-$C_8$ cycloalkyl, or R' and R" combine with the carbon atom to which they are bound to form optionally substituted $C_3$-$C_8$ cycloalkyl;

$R^{1a}$ is selected from the group consisting of optionally substituted $C_1$-$C_6$ alkyl, optionally substituted $C_1$-$C_6$ haloalkyl, optionally substituted $C_3$-$C_8$ cycloalkyl, and NRR, wherein each occurrence of R is independently selected from the group consisting of H and optionally substituted $C_1$-$C_6$ alkyl;

$R^2$ is selected from the group consisting of: 1H-tetrazol-5-yl,
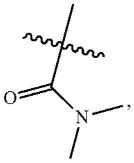,
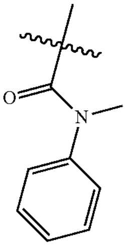,
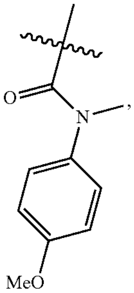,
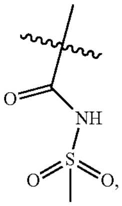,
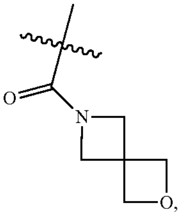,
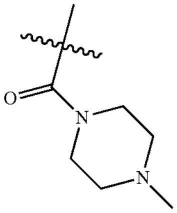,
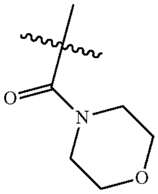,
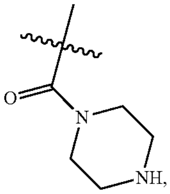,
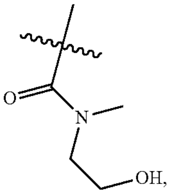,
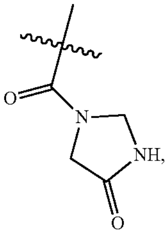,
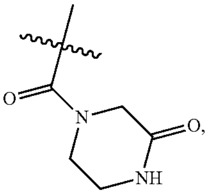,
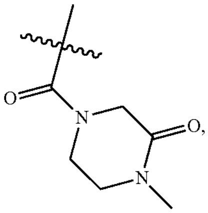,
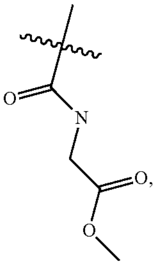,
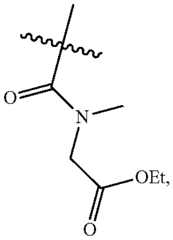,
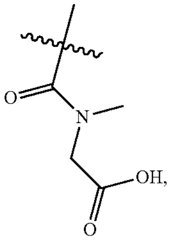,
-continued
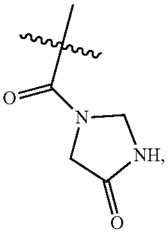,
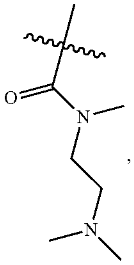,
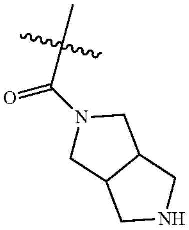,
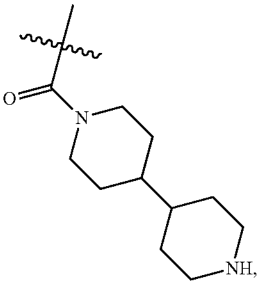
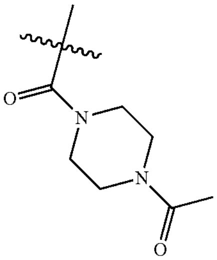,
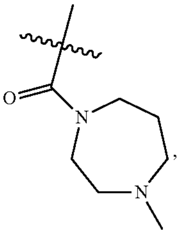,
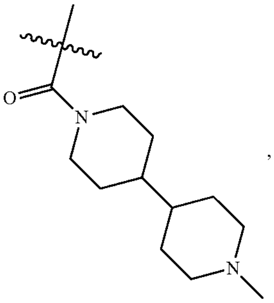,
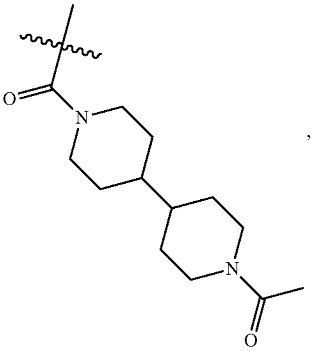,
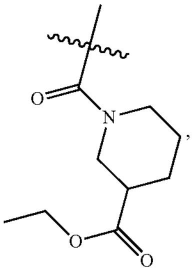,
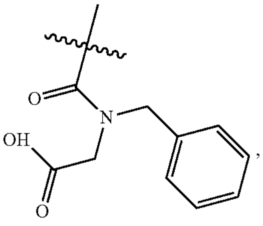,
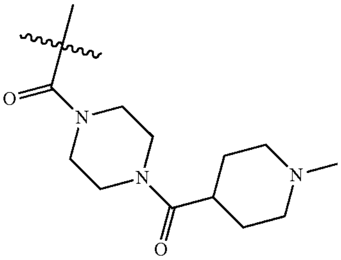,
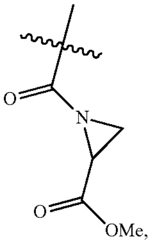, -continued
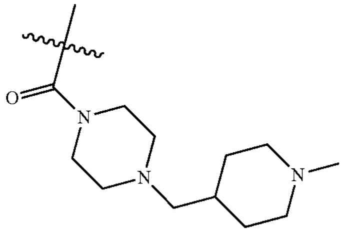,
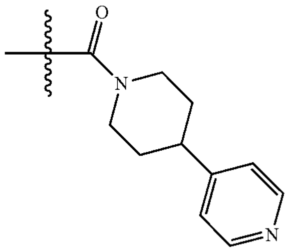,
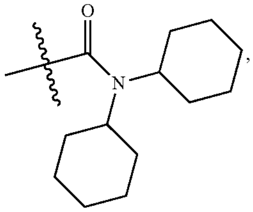,
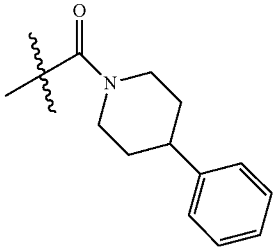,
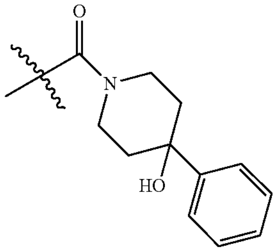,
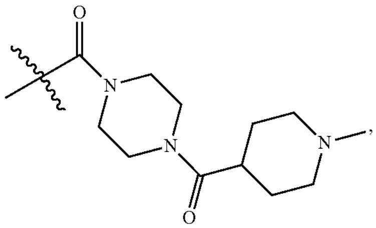,
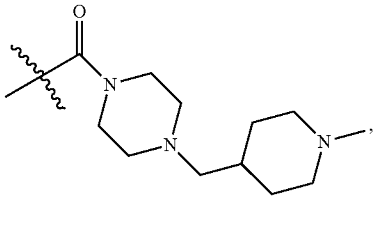,
-continued
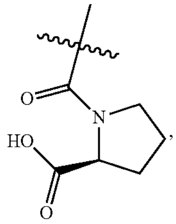, 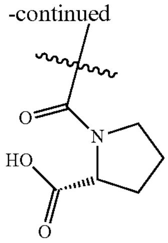,
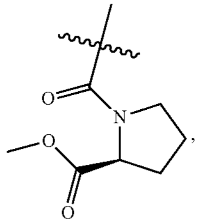, 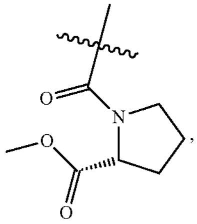,
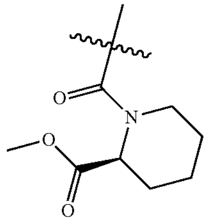, 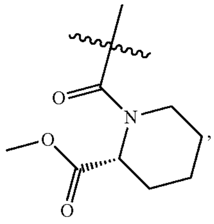,
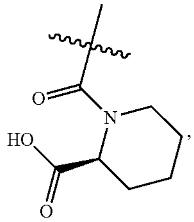, 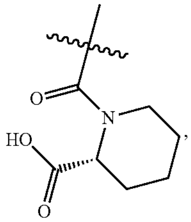,
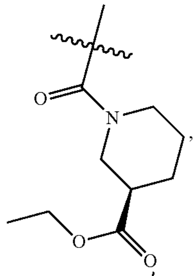, 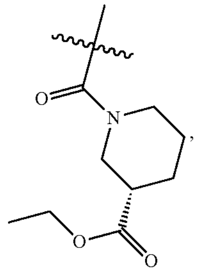,
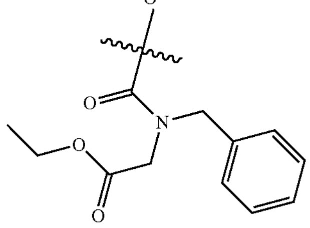,
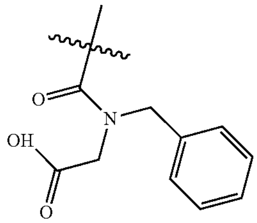, and 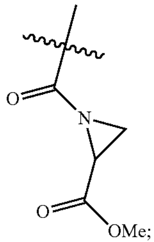;
$R^3$ is $C_1$-$C_6$ thioether.
21. The method of claim 20, wherein the MKP5 modulated disease or disorder is a fibrotic disease or disorder.

22. The method of claim 21, wherein the MKP5 modulated disease or disorder is selected from the group consisting of dystrophic muscle disease, a cardiac or vascular disease, idiopathic pulmonary fibrosis, or any combinations thereof.

23. The method of claim 20, wherein the subject is a mammal.

24. The method of claim 23, wherein the mammal is a human.

25. The method of claim 20, wherein the compound is administered to the subject by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal, and intravenous routes.

26. The method of claim 20, further comprising administering to the subject at least one additional agent that treats or ameliorates the MKP5 modulated disease or disorder in the mammal.

27. The method of claim 26, wherein the compound and at least one additional agent are coformulated.

* * * * *

SEQUENCE LISTING

<160> NUMBER OF SEQ ID NOS: 18

<210> SEQ ID NO 1
<211> LENGTH: 47
<212> TYPE: PRT
<213> ORGANISM: Homo sapiens

<400> SEQUENCE: 1

His Cys Gln Ala Gly Val Ser Arg Ser Ala Thr Ile Val Ile Ala Tyr
1               5                   10                  15

Leu Met Lys His Thr Arg Met Thr Met Thr Asp Ala Tyr Lys Phe Val
            20                  25                  30

Lys Gly Lys Arg Pro Ile Ile Ser Pro Asn Leu Asn Phe Met Gly
        35                  40                  45

<210> SEQ ID NO 2
<211> LENGTH: 47
<212> TYPE: PRT
<213> ORGANISM: Homo sapiens

<400> SEQUENCE: 2

His Cys Leu Ala Gly Ile Ser Arg Ser Ala Thr Ile Ala Ile Ala Tyr

-continued

```
1               5                   10                  15

Ile Met Lys Arg Met Asp Met Ser Leu Asp Glu Ala Tyr Arg Phe Val
            20                  25                  30

Lys Glu Lys Arg Pro Thr Ile Ser Pro Asn Phe Asn Phe Leu Gly
        35                  40                  45


<210> SEQ ID NO 3
<211> LENGTH: 47
<212> TYPE: PRT
<213> ORGANISM: Homo sapiens

<400> SEQUENCE: 3

His Cys Leu Ala Gly Ile Ser Arg Ser Ala Thr Ile Ala Ile Ala Tyr
1               5                   10                  15

Ile Met Lys Thr Met Gly Met Ser Ser Asp Asp Ala Tyr Arg Phe Val
            20                  25                  30

Lys Asp Arg Arg Pro Ser Ile Ser Pro Asn Phe Asn Phe Leu Gly
        35                  40                  45


<210> SEQ ID NO 4
<211> LENGTH: 47
<212> TYPE: PRT
<213> ORGANISM: Homo sapiens

<400> SEQUENCE: 4

His Cys Gln Ala Gly Ile Ser Arg Ser Ala Thr Ile Cys Leu Ala Tyr
1               5                   10                  15

Leu Met Arg Thr Asn Arg Val Lys Leu Asp Glu Ala Phe Glu Phe Val
            20                  25                  30

Lys Gln Arg Arg Ser Ile Ile Ser Pro Asn Phe Ser Phe Met Gly
        35                  40                  45


<210> SEQ ID NO 5
<211> LENGTH: 47
<212> TYPE: PRT
<213> ORGANISM: Homo sapiens

<400> SEQUENCE: 5

His Cys Gln Ala Gly Ile Ser Arg Ser Ala Thr Ile Cys Leu Ala Tyr
1               5                   10                  15

Leu Met Met Lys Lys Arg Val Arg Leu Glu Glu Ala Phe Glu Phe Val
            20                  25                  30

Lys Gln Arg Arg Ser Ile Ile Ser Pro Asn Phe Ser Phe Met Gly
        35                  40                  45


<210> SEQ ID NO 6
<211> LENGTH: 47
<212> TYPE: PRT
<213> ORGANISM: Homo sapiens

<400> SEQUENCE: 6

His Cys Gln Ala Gly Ile Ser Arg Ser Ala Thr Ile Cys Leu Ala Tyr
1               5                   10                  15

Leu Met Gln Ser Arg Arg Val Arg Leu Asp Glu Ala Phe Asp Phe Val
            20                  25                  30

Lys Gln Arg Arg Gly Val Ile Ser Pro Asn Phe Ser Phe Met Gly
        35                  40                  45


<210> SEQ ID NO 7
<211> LENGTH: 47
```

```
<212> TYPE: PRT
<213> ORGANISM: Homo sapiens

<400> SEQUENCE: 7

His Cys Leu Ala Gly Ile Ser Arg Ser Val Thr Val Thr Val Ala Tyr
1               5                   10                  15

Leu Met Gln Lys Met Asn Leu Ser Leu Asn Asp Ala Tyr Asp Phe Val
            20                  25                  30

Lys Arg Lys Lys Ser Asn Ile Ser Pro Asn Phe Asn Phe Met Gly
        35                  40                  45


<210> SEQ ID NO 8
<211> LENGTH: 47
<212> TYPE: PRT
<213> ORGANISM: Homo sapiens

<400> SEQUENCE: 8

His Cys Leu Ala Gly Ile Ser Arg Ser Val Thr Val Thr Val Ala Tyr
1               5                   10                  15

Leu Met Gln Lys Leu Asn Leu Ser Met Asn Asp Ala Tyr Asp Ile Val
            20                  25                  30

Lys Met Lys Lys Ser Asn Ile Ser Pro Asn Phe Asn Phe Met Gly
        35                  40                  45


<210> SEQ ID NO 9
<211> LENGTH: 47
<212> TYPE: PRT
<213> ORGANISM: Homo sapiens

<400> SEQUENCE: 9

His Cys Leu Ala Gly Val Ser Arg Ser Val Thr Val Thr Val Ala Tyr
1               5                   10                  15

Leu Met Gln Lys Leu His Leu Ser Leu Asn Asp Ala Tyr Asp Leu Val
            20                  25                  30

Lys Arg Lys Lys Ser Asn Ile Ser Pro Asn Phe Asn Phe Met Gly
        35                  40                  45


<210> SEQ ID NO 10
<211> LENGTH: 47
<212> TYPE: PRT
<213> ORGANISM: Homo sapiens

<400> SEQUENCE: 10

His Cys Glu Ala Gly Ile Ser Arg Ser Pro Thr Ile Cys Met Ala Tyr
1               5                   10                  15

Leu Met Lys Thr Lys Gln Phe Arg Leu Lys Glu Ala Phe Asp Tyr Ile
            20                  25                  30

Lys Gln Arg Arg Ser Met Val Ser Pro Asn Phe Gly Phe Met Gly
        35                  40                  45


<210> SEQ ID NO 11
<211> LENGTH: 47
<212> TYPE: PRT
<213> ORGANISM: Homo sapiens

<400> SEQUENCE: 11

His Cys Leu Ala Gly Val Ser Arg Ser Val Thr Leu Val Ile Ala Tyr
1               5                   10                  15

Ile Met Thr Val Thr Asp Phe Gly Trp Glu Asp Ala Leu His Thr Val
            20                  25                  30
```

-continued

Arg Ala Gly Arg Ser Cys Ala Asn Pro Asn Val Gly Phe Gln Arg
35 40 45

<210> SEQ ID NO 12
<211> LENGTH: 46
<212> TYPE: PRT
<213> ORGANISM: Homo sapiens

<400> SEQUENCE: 12

His Cys Arg Glu Gly Tyr Ser Arg Ser Pro Thr Leu Val Ile Ala Tyr
1 5 10 15

Leu Met Met Arg Gln Lys Met Asp Val Lys Ser Ala Leu Ser Ile Val
20 25 30

Arg Gln Asn Arg Glu Ile Gly Pro Asn Asp Gly Phe Leu Ala
35 40 45

<210> SEQ ID NO 13
<211> LENGTH: 47
<212> TYPE: PRT
<213> ORGANISM: Homo sapiens
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 13

His Cys Leu Ala Gly Ile Ser Arg Ser Ala Thr Ile Cys Ile Ala Tyr
1 5 10 15

Leu Met Xaa Lys Met Arg Met Ser Leu Asp Asp Ala Tyr Asp Phe Val
20 25 30

Lys Gln Xaa Arg Ser Xaa Ile Ser Pro Asn Phe Asn Phe Met Gly
35 40 45

<210> SEQ ID NO 14
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 14

Asp Asp Glu Xaa Thr Gly Tyr Val Ala Thr Arg
1 5 10

<210> SEQ ID NO 15
<211> LENGTH: 12
<212> TYPE: PRT
<213> ORGANISM: Artificial Sequence -continued
<220> FEATURE:
<223> OTHER INFORMATION: Chemical synthesized
<220> FEATURE:
<221> NAME/KEY: MISC_FEATURE
<222> LOCATION: (5)..(5)
<223> OTHER INFORMATION: Thr is phophorylated.
<220> FEATURE:
<221> NAME/KEY: MISC_FEATURE
<222> LOCATION: (7)..(7)

<400> SEQUENCE: 15

Asp Asp Glu Asn Leu Thr Gly Tyr Val Ala Thr Arg
1 5 10

<210> SEQ ID NO 16
<211> LENGTH: 4
<212> TYPE: PRT
<213> ORGANISM: Artificial Sequence
<220> FEATURE:
<223> OTHER INFORMATION: Chemically synthesized

<400> SEQUENCE: 16

Ile Ser Pro Asn
1

<210> SEQ ID NO 17
<211> LENGTH: 5
<212> TYPE: PRT
<213> ORGANISM: Artificial Sequence
<220> FEATURE:
<223> OTHER INFORMATION: Chemically synthesized

<400> SEQUENCE: 17

Ala Gly Val Ser Arg
1 5

<210> SEQ ID NO 18
<211> LENGTH: 4
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Tyr is phosphorylated.

<400> SEQUENCE: 18

Tyr Val Ala Thr
1